(12) United States Patent  
De Silva et al.

(10) Patent No.: US 10,703,971 B2  
(45) Date of Patent: Jul. 7, 2020

(54) CHEMILUMINESCENT SUBSTRATES

(71) Applicant: Beckman Coulter, Inc., Brea, CA (US)

(72) Inventors: Renuka De Silva, Brea, CA (US); Robert A. Eickholt, Brea, CA (US); Jaya S. Koti, Brea, CA (US); Mark D. Sandison, Brea, CA (US); David L. Schumm, Brea, CA (US); Wenhua Xie, Brea, CA (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 16/313,438

(22) PCT Filed: Jun. 30, 2017

(86) PCT No.: PCT/US2017/040457  
§ 371 (c)(1),  
(2) Date: Dec. 26, 2018

(87) PCT Pub. No.: WO2018/006059  
PCT Pub. Date: Jan. 4, 2018

(65) Prior Publication Data  
US 2019/0161675 A1 May 30, 2019

Related U.S. Application Data

(60) Provisional application No. 62/357,091, filed on Jun. 30, 2016.

(51) Int. Cl.  
*C09K 11/06* (2006.01)  
*G01N 33/533* (2006.01)

(52) U.S. Cl.  
CPC ............ *C09K 11/06* (2013.01); *G01N 33/533* (2013.01); *C09K 2211/104* (2013.01); *C09K 2211/1029* (2013.01); *C09K 2211/1033* (2013.01); *C09K 2211/1037* (2013.01)

(58) Field of Classification Search  
CPC . C09K 11/06; C09K 11/07; C09K 2211/1029; C09K 2211/1033; C09K 2211/1037; C09K 2211/104  
USPC ......................................................... 252/700  
See application file for complete search history.

(56) References Cited

U.S. PATENT DOCUMENTS

| | | | |
|---|---|---|---|
| 5,112,960 A | 5/1992 | Bronstein et al. | |
| 5,772,926 A | 6/1998 | Akhavan-Tafti | |
| 5,965,736 A | 10/1999 | Akhavan-Tafti | |
| 6,045,727 A * | 4/2000 | Akhavan-Tafti | C07F 9/5765 252/700 |
| 6,090,571 A | 7/2000 | Akhavan-Tafti | |
| 6,139,782 A | 10/2000 | Akhavan-Tafti et al. | |
| 6,218,137 B1 | 4/2001 | Akhavan-Tafti et al. | |
| 6,270,695 B1 | 8/2001 | Akhavan-Tafti et al. | |

(Continued)

OTHER PUBLICATIONS

Triton X Surfactants. Downloaded on Oct. 16, 2019 from https://search.cosmobio.co.jp/cosmo_search_p/search_gate2/docs/ICN_/194854.20050301.pdf.*

(Continued)

*Primary Examiner* — Vu A Nguyen  
(74) *Attorney, Agent, or Firm* — McAndrews, Held & Malloy, Ltd.

(57) ABSTRACT

Alkaline phosphatase chemiluminescent substrate formulations are provided exhibiting rapid incubation periods and improved stability for use in immunoassays.

19 Claims, 20 Drawing Sheets

(56) References Cited

U.S. PATENT DOCUMENTS 6,296,787 B1    10/2001    Akhavan-Tafti et al.

OTHER PUBLICATIONS

SciFinder Search (Oct. 15, 2019).*
Li et al., "Effects of NH4CL on the interaction between poly(ethylene oxide) and ionic surfactants in aqueous solutions", Chinese Journal of Polymer Science, vol. 26, No. 1, 2008, pp. 31-37.
Guo et al., "Interaction of PEG with ionic surfactant SDS to form template for mesoporous material", Colloids and Surfaces A: Physicochem. Eng. Aspects, vol. 252, 2005, pp. 71-77.
Nassar et al., "Photophysical probe studies of polymer-detergent interactions", J. Braz. Chem. Soc., vol. 6, No. 2, 1994, pp. 173-178.
Olofsson et al., "Interaction between surfactants and uncharged polymers in aqueous solution studied by microcalorimetry", Pure & Appl. Chem., vol. 66, No. 2, 1994, pp. 527-532.
Access Total BetahCG assay datasheet, 2003, 10 pages total.
Access AccuTnl assay datasheet, 2010, 18 pages total.
Access HYPERsensitive hTSH assay and Fast hTSH assay datasheet, 2010, 15 pages total.
Lumigen APS-5 chemiluminescent reagent product application instructions, downloaded Oct. 14, 2015, 7 pages total.
Stravroudis, "Sorting out surfactants", WAAC Newsletter, vol. 31, No. 1, 2009, pp. 18-21.
Lumi-Phos 530 ELISA AP Substrate datasheet, downloaded Oct. 14, 2015, 2 pages total.
Millan, "Alkaline phosphatases: structure, substrate specificity and functional relatedness to other members of a large superfamily of enzymes", Purinergic Signalling, vol. 2, 2006, pp. 335-341.
Roche, "Alkaline Phosphatase for the diagnostics and life sciences industry", 2010, 12 pages total.
Phosphate, alkaline, from calf intestine datasheet, Roche, 2013, 1 page total.
Phosphate, alkaline, from *Escherichia coli* safety data sheet, Sigma-Aldrich, 2014, 6 pages total.
Shrimp Alkaline Phosphatase, recombinant (rSAP) datasheet, downloaded Jan. 26, 2016, 2 pages total.
International Search Report and Written Opinion for PCT/US2017/040457 dated Sep. 18, 2017.

\* cited by examiner

| Assay | Format | Conjugate pH | Other Info |
|---|---|---|---|
| AccuTnI+3 | Sandwich-Piggyback | ACES pH 6.0 | 4% BSA & 2.5% chemal in PMP REC ALP |
| Old BHCG | Sandwich-1 step | Tris pH 7.1 | |
| NEW BHCG5 | Sandwich-Piggyback | Tris pH 7.1 | REC ALP |
| TSH | Sandwich-1 step | Tris pH 7.4 | |
| TSH2 | Sandwich-1 step | ACES pH 6.0 | REC ALP |
| CK-MB | Sandwich-1 step | Sod Phos pH 5.9 | 0.006% Dextran sulfate in PMP |
| Myoglobin | Sandwich-1 step | Sod Phos pH 6.0 | Antibody not coupled to PMP |
| Digoxin | Competitive-1 step | Tris, pH 8.05 | |
| PTH (IO) | Sandwich-1 step | ACES pH 7.0 | 20% sucrose, 0.2% plurafac |

FIG. 5

| Sample | Assigned Conc. (ng/mL) | Digoxin ||||||||
|---|---|---|---|---|---|---|---|---|---|
| | | LP-530 || SMS-PEG |||| SMS-Triton ||||
| | | L5 || L2 || L5 || L2 || L5 ||
| | | Mean RLU | % CV | Mean RLU | % CV | Mean RLU | % CV | Mean RLU | % CV | Mean RLU | % CV |
| S0 | 0 | 2,228,650 | 3.12 | 1,860,492 | 3.64 | 1,777,889 | 3.69 | 1,542,138 | 1.22 | 1,255,630 | 1.33 |
| S1 | 0.52 | 1,210,291 | 2.21 | 965,358 | 1.70 | 925,528 | 2.69 | 819,110 | 2.16 | 675,864 | 1.79 |
| S2 | 1.05 | 725,599 | 2.68 | 600,232 | 1.78 | 573,813 | 1.09 | 504,611 | 2.16 | 424,819 | 1.93 |
| S3 | 2.02 | 384,812 | 1.92 | 318,731 | 2.73 | 312,184 | 2.64 | 262,327 | 2.20 | 228,649 | 1.64 |
| S4 | 4.27 | 189,173 | 1.41 | 139,936 | 5.94 | 140,731 | 5.10 | 122,056 | 3.23 | 111,344 | 3.64 |
| S5 | 5.9 | 125,117 | 3.51 | 95,454 | 3.37 | 98,392 | 2.43 | 81,422 | 3.08 | 74,845 | 2.59 |
| BioRad Liquichek 1 | | 811,411 | 7.44 | 624,182 | 1.25 | 593,946 | 1.23 | 571,089 | 2.82 | 464,042 | 2.94 |
| BioRad Liquichek 2 | | 454,199 | 3.76 | 301,493 | 2.31 | 288,763 | 2.71 | 303,009 | 6.86 | 254,421 | 6.45 |
| BioRad Liquichek 3 | | 292,939 | 2.21 | 188,833 | 3.56 | 184,179 | 2.84 | 209,387 | 2.82 | 177,585 | 2.47 |
| Serum Pool 1 | | 514,616 | 2.96 | 454,248 | 3.20 | 436,149 | 2.91 | 376,970 | 4.33 | 316,738 | 4.29 |
| Serum Pool 2 | | 198,121 | 1.65 | 165,325 | 2.68 | 162,801 | 3.17 | 141,265 | 4.80 | 122,559 | 4.66 |

FIG. 6A

| Sample | Assigned Conc. (pg/mL) | PTH (IO) | | | | | | | | | | | |
|---|---|---|---|---|---|---|---|---|---|---|---|---|---|
| | | LP-530 | | | SMS-PEG | | | | | SMS-Triton | | | |
| | | L5 | | | L2 | | L5 | | | L2 | | L5 | |
| | | Mean RLU | % CV | | Mean RLU | % CV | Mean RLU | | % CV | Mean RLU | % CV | Mean RLU | % CV |
| S0 | 0 | 10,584 | 1.14 | | 4,518 | 2.36 | 5,796 | | 2.48 | 3,948 | 2.73 | 4,712 | 2.38 |
| S1 | 9.7 | 21,230 | 1.50 | | 13,277 | 2.13 | 17,943 | | 2.97 | 9,968 | 2.18 | 12,013 | 3.35 |
| S2 | 57.5 | 76,431 | 2.98 | | 57,186 | 3.12 | 78,141 | | 2.83 | 40,864 | 2.26 | 49,264 | 2.00 |
| S3 | 289 | 321,458 | 2.99 | | 271,588 | 2.37 | 377,684 | | 0.71 | 180,147 | 2.63 | 217,273 | 4.24 |
| S4 | 1481 | 1,503,816 | 4.99 | | 1,232,218 | 2.93 | 1,724,140 | | 2.61 | 861,223 | 3.22 | 1,039,140 | 2.40 |
| S5 | 3458 | 3,435,685 | 2.52 | | 2,753,315 | 2.34 | 3,924,670 | | 2.50 | 1,958,194 | 3.78 | 2,411,363 | 3.02 |
| BioRad Specialty LTA | | 28,695 | 7.99 | | 26,748 | 1.76 | 31,155 | | 1.86 | 17,197 | 1.48 | 19,829 | 2.22 |
| BioRad Specialty 1 | | 31,271 | 3.17 | | 27,903 | 2.81 | 32,532 | | 2.52 | 17,600 | 6.50 | 20,521 | 7.96 |
| BioRad Specialty 2 | | 206,045 | 5.11 | | 219,594 | 4.96 | 254,507 | | 4.48 | 131,449 | 3.21 | 152,837 | 2.58 |
| BioRad Specialty 3 | | 576,989 | 4.68 | | 606,889 | 2.22 | 718,550 | | 2.12 | 375,589 | 3.31 | 437,282 | 2.20 |
| SerumPool 1 | | 33,086 | 2.30 | | 24,677 | 4.93 | 30,108 | | 6.06 | 17,152 | 4.52 | 21,337 | 3.25 |
| Serum Pool 2 | | 211,252 | 4.01 | | 192,571 | 1.97 | 239,974 | | 1.58 | 129,097 | 1.39 | 160,051 | 1.41 |

FIG. 6B

| Sample | Assigned Conc. (mIU/L) | TSH | | | | | | | | | | | |
|---|---|---|---|---|---|---|---|---|---|---|---|---|---|
| | | LP-530 | | | | SMS-PEG | | | | SMS-Triton | | | |
| | | L5 | | L2 | | L2 | | L5 | | L2 | | L5 | |
| | | Mean RLU | % CV | Mean RLU | % CV | Mean RLU | % CV | Mean RLU | % CV | Mean RLU | % CV | Mean RLU | % CV |
| S0 | 0 | 10,365 | 1.81 | 4,445 | 3.43 | 4,662 | 2.20 | 3,981 | 3.51 | 4,349 | 2.24 |
| S1 | 0.104 | 50,909 | 3.34 | 55,436 | 3.29 | 61,836 | 1.20 | 37,853 | 2.09 | 45,820 | 1.45 |
| S2 | 0.5 | 209,929 | 1.88 | 272,641 | 2.70 | 286,886 | 2.91 | 170,656 | 1.25 | 206,481 | 1.19 |
| S3 | 4 | 1,506,408 | 3.44 | 2,088,507 | 3.54 | 2,210,526 | 3.18 | 1,286,767 | 2.10 | 1,547,491 | 0.89 |
| S4 | 9.8 | 3,602,852 | 1.46 | 4,778,050 | 1.87 | 5,129,173 | 0.91 | 3,038,600 | 2.00 | 3,650,953 | 1.59 |
| S5 | 100 | 21,400,903 | 1.48 | 26,441,609 | 0.40 | 26,786,552 | 1.36 | 19,785,138 | 1.38 | 21,954,945 | 1.55 |
| BioRad QC 1 | | 274,535 | 6.46 | 351,902 | 8.47 | 399,907 | 6.23 | 229,006 | 4.03 | 281,541 | 4.86 |
| BioRad QC 2 | | 1,752,409 | 2.19 | 2,288,521 | 3.30 | 2,613,500 | 2.58 | 1,538,493 | 2.92 | 1,891,374 | 1.91 |
| BioRad QC 3 | | 6,767,267 | 2.66 | 8,812,593 | 3.16 | 9,711,847 | 1.67 | 6,132,723 | 3.06 | 7,309,848 | 2.35 |
| Serum Pool 1 | | 232,309 | 3.56 | 342,523 | 4.87 | 379,159 | 3.97 | 197,435 | 4.04 | 241,403 | 2.52 |
| Serum Pool 2 | | 4,119,141 | 1.71 | 5,797,598 | 3.35 | 6,279,695 | 1.99 | 3,634,123 | 1.98 | 4,385,902 | 1.25 |

FIG. 6C

| Sample | Assigned Conc. (mIU/L) | TSH2 ||||||||
|---|---|---|---|---|---|---|---|---|---|
| | | LP-530 || SMS-PEG |||| SMS-Triton |||
| | | L5 || L2 || L5 || L2 || L5 ||
| | | Mean RLU | % CV | Mean RLU | % CV | Mean RLU | % CV | Mean RLU | % CV | Mean RLU | % CV |
| S0 | 0 | 8,578 | 1.71 | 3,249 | 3.10 | 2,909 | 3.2 | 3,584 | 1.78 | 3,172 | 2 |
| S1 | 0.05 | 84,429 | 2.22 | 74,925 | 4.33 | 59,273 | 2.4 | 51,546 | 0.74 | 44,285 | 0.6 |
| S2 | 0.3 | 451,620 | 0.88 | 401,261 | 4.24 | 322,641 | 3.5 | 285,822 | 2.51 | 244,598 | 2.2 |
| S3 | 3 | 4,069,764 | 1.05 | 3,786,580 | 2.62 | 3,114,349 | 2.6 | 2,719,723 | 3.44 | 2,332,441 | 2.3 |
| S4 | 15 | 16,366,901 | 2.51 | 16,363,712 | 2.90 | 13,603,846 | 1.1 | 11,937,677 | 3.46 | 10,579,646 | 1.8 |
| S5 | 50 | 34,028,794 | 4.93 | 34,529,440 | 1.08 | 29,000,305 | 0.3 | 29,603,190 | 1.57 | 26,955,063 | 0.6 |
| BioRad QC 1 | | 1,188,027 | 1.67 | 996,777 | 1.97 | 846,130 | 2 | 752,195 | 1.52 | 658,325 | 1.8 |
| BioRad QC 2 | | 7,112,755 | 3.34 | 6,834,600 | 5.26 | 5,792,688 | 3 | 5,289,908 | 2.42 | 4,670,096 | 1.4 |
| BioRad QC 3 | | 22,880,749 | 2.24 | 23,479,184 | 2.37 | 19,549,719 | 1.4 | 18,573,231 | 3.84 | 17,203,790 | 1.4 |
| Serum Pool 1 | | 930,753 | 2.03 | 995,467 | 3.57 | 873,369 | 9.5 | 623,833 | 5.16 | 580,736 | 1.9 |
| Serum Pool 2 | | 14,094,641 | 1.83 | 14,479,773 | 3.64 | 11,996,209 | 2.4 | 10,861,394 | 1.89 | 9,551,410 | 1.3 |

FIG. 6D

| Sample | Assigned Conc. ng/ml | AccuTnI+3 ||||||||||||
|---|---|---|---|---|---|---|---|---|---|---|---|---|---|
| | | LP-530 || SMS-PEG |||| SMS-Triton ||||
| | | L5 | | L2 || L5 || L2 || L5 ||
| | | Mean RLU | % CV | Mean RLU | % CV | Mean RLU | % CV | Mean RLU | % CV | Mean RLU | % CV |
| S0 | 0 | 10,460 | 2.42 | 2,643 | 5.07 | 2,918 | 3.82 | 2,274 | 5.72 | 2,194 | 3.56 |
| S1 | 0.228 | 73,555 | 3.22 | 25,906 | 1.39 | 23,774 | 1.36 | 19,293 | 1.72 | 18,098 | 1.04 |
| S2 | 0.937 | 274,265 | 1.02 | 98,822 | 2.00 | 88,998 | 1.15 | 72,924 | 1.17 | 68,566 | 1.42 |
| S3 | 3.77 | 1,085,007 | 0.60 | 403,930 | 2.73 | 360,812 | 1.49 | 298,775 | 1.01 | 279,867 | 1.24 |
| S4 | 20.4 | 5,369,419 | .067 | 1,958,916 | 1.31 | 1,788,966 | 1.51 | 1,528,124 | 2.07 | 1,433,081 | 1.90 |
| S5 | 76 | 16,122,355 | 0.91 | 6,733,092 | 2.60 | 6,399,896 | 0.93 | 5,153,890 | 2.02 | 4,905,487 | 1.80 |
| BioRad Card-01 | | 100,190 | 2.24 | 41,285 | 3.75 | 34,645 | 3.36 | 30,003 | 1.20 | 24,846 | 1.96 |
| BioRad Card-02 | | 538,877 | 2.37 | 228,442 | 1.90 | 191,105 | 1.90 | 171,390 | 3.19 | 140,323 | 3.25 |
| BioRad Card-03 | | 2,207,905 | 1.74 | 929,151, | 3.78 | 777,297 | 2.83 | 723,278 | 3.22 | 590,197 | 2.92 |
| Pool-Low | | 45,943 | 4.14 | 22,203 | 3.23 | 19,390 | 4.08 | 17,386 | 2.41 | 14,649 | 2.78 |
| Pool High | | 531,555 | 2.42 | 289,135 | 1.74 | 239,917 | 1.57 | 221,521 | 2.06 | 181,955 | 2.53 |
| Negative Serum-ALL | | 10,924 | 7.22 | 3,293 | 14.49 | 3,410 | 10.62 | 2,860 | 12.21 | 2,575 | 10.16 |

FIG. 6E

BNP

| Sample | Assigned Conc. (pg/mL) | LP-530 | | | | SMS-PEG | | | | SMS-Triton | | | |
|---|---|---|---|---|---|---|---|---|---|---|---|---|---|
| | | L5 Mean RLU | % CV | L2 Mean RLU | % CV | L2 Mean RLU | % CV | L5 Mean RLU | % CV | L2 Mean RLU | % CV | L5 Mean RLU | % CV |
| S0 | 0 | 10,480 | 1.57 | 3,704 | 2.21 | 4,355 | 2.44 | 3,248 | 1.89 | 3,898 | 2.42 |
| S1 | 28.5 | 79,172 | 1.96 | 61,573 | 1.08 | 75,436 | 0.17 | 50,572 | 2.07 | 60,364 | 2.02 |
| S2 | 113.6 | 281,627 | 2.46 | 237,091 | 2.63 | 289,386 | 1.70 | 196,774 | 3.12 | 233,341 | 2.86 |
| S3 | 501 | 1,503,268 | 1.34 | 1,308,204 | 0.61 | 1,626,445 | 0.28 | 1,017,657 | 2.41 | 1,191,215 | 2.13 |
| S4 | 2442 | 9,106,724 | 1.44 | 8,490,458 | 0.95 | 10,396,829 | 1.07 | 6,462,696 | 1.52 | 7,416,289 | 1.70 |
| S5 | 4929 | 17,238,997 | 2.03 | 17,150,937 | 4.59 | 20,036,722 | 2.99 | 13,346,271 | 1.37 | 15,521,725 | 0.82 |
| BioRad QC 1 | | 232,020 | 3.19 | 178,354 | 0.74 | 218,710 | 1.34 | 152,408 | 4.83 | 181,545 | 4.21 |
| BioRad QC 2 | | 1,200,981 | 1.17 | 924,925 | 2.53 | 1,146,622 | 1.14 | 811,004 | 1.93 | 948,586 | 1.73 |
| BioRad QC 3 | | 7,575,614 | 3.59 | 6,823,392 | 1.41 | 8,601,741 | 1.44 | 5,588,089 | 2.03 | 6,363,334 | 1.37 |
| Serum Pool 1 | | 57,599 | 1.30 | 24,433 | 2.84 | 26,739 | 1.70 | 20,203 | 3.44 | 23,699 | 3.50 |
| Serum Pool 2 | | 617,273 | 2.22 | 334,891 | 2.55 | 334,802 | 1.59 | 251,997 | 2.21 | 284,123 | 2.70 |

FIG. 6F

| Sample | Assigned Conc. (µg/L) | CK-MB ||||||||||||
|---|---|---|---|---|---|---|---|---|---|---|---|---|
| | | LP-530 |||| SMS-PEG |||| SMS-Triton ||||
| | | L5 ||| | L2 ||| L5 ||| L2 ||| L5 |||
| | | Mean RLU | % CV | Mean RLU | % CV | Mean RLU | % CV | Mean RLU | % CV | Mean RLU | % CV |
| S0 | 0 | 12,043 | 1.12 | 3,341 | 3.69 | 3,780 | 2.38 | 3,228 | 2.90 | 3,688 | 2.66 |
| S1 | 2.9 | 136,353 | 0.99 | 93,972 | 1.88 | 101,270 | 1.68 | 65,715 | 1.83 | 74,741 | 1.38 |
| S2 | 9.8 | 434,703 | 2.31 | 317,287 | 2.96 | 337,607 | 3.44 | 209,574 | 4.41 | 236,856 | 4.60 |
| S3 | 29.5 | 1,290,773 | 0.59 | 933,036 | 2.16 | 999,806 | 1.25 | 620,773 | 2.03 | 697,684 | 2.13 |
| S4 | 99 | 4,467,294 | 2.15 | 3,203,902 | 0.53 | 3,565,864 | 1.03 | 2,162,677 | 1.85 | 2,338,262 | 2.19 |
| S5 | 308 | 13,863,659 | 1.39 | 9,489,680 | 1.72 | 11,239,762 | 0.91 | 6,624,206 | 2.40 | 6,896,454 | 2.19 |
| BioRad Cardiac 1 | | 142,558 | 1.82 | 99,218 | 5.08 | 113,011 | 4.42 | 73,269 | 4.06 | 85,939 | 3.99 |
| BioRad Cardiac 2 | | 607,655 | 1.25 | 458,131 | 1.62 | 526,924 | 0.84 | 337,186 | 3.03 | 392,268 | 2.78 |
| BioRad Cardiac 3 | | 3,055,131 | 1.25 | 2,276,919 | 1.28 | 2,685,597 | 2.01 | 1,643,394 | 1.57 | 1,832,616 | 1.56 |
| Serum Pool 1 | | 175,023 | 1.95 | 129,727 | 1.12 | 141,843 | 1.05 | 90,491 | 2.43 | 102,658 | 1.82 |
| Serum Pool 2 | | 953,481 | 1.78 | 730,515 | 2.11 | 791,321 | 1.47 | 486,151 | 3.55 | 542,913 | 3.21 |

FIG. 6G

| Sample | Assigned Conc. (μg/L) | Myoglobin | | | | | | | | | | | |
|---|---|---|---|---|---|---|---|---|---|---|---|---|---|
| | | LP-530 | | | | SMS-PEG | | | | SMS-Triton | | | |
| | | L5 | | L2 | | L5 | | L2 | | L5 | | | |
| | | Mean RLU | % CV | Mean RLU | % CV | Mean RLU | % CV | Mean RLU | % CV | Mean RLU | % CV | Mean RLU | % CV |
| S0 | 0 | 16,717 | 0.99 | 5,846 | 1.96 | 6,216 | 1.51 | 5,022 | 1.89 | 5,178 | 2.32 | | |
| S1 | 49.7 | 198,553 | 1.10 | 222,627 | 0.81 | 186,346 | 1.70 | 159,231 | 4.03 | 139,554 | 3.93 | | |
| S2 | 186 | 774,339 | 2.72 | 914,979 | 3.41 | 755,886 | 3.14 | 674,003 | 2.39 | 583,744 | 3.36 | | |
| S3 | 801 | 3,486,261 | 1.45 | 4,029,171 | 2.07 | 3,328,205 | 1.68 | 2,898,698 | 0.75 | 2,522,353 | 1.13 | | |
| S4 | 2067 | 8,472,899 | 2.26 | 9,750,443 | 1.48 | 8,116,555 | 2.26 | 6,736,742 | 1.36 | 5,989,315 | 2.32 | | |
| S5 | 4024 | 13,927,231 | 0.13 | 15,546,032 | 1.17 | 12,860,716 | 1.43 | 11,458,383 | 1.68 | 10,302,843 | 1.55 | | |
| BioRad Cardiac 1 | | 130,097 | 1.30 | 133,393 | 3.18 | 111,793 | 2.63 | 101,407 | 5.96 | 88,448 | 6.20 | | |
| BioRad Cardiac 2 | | 360,919 | 1.99 | 400,725 | 2.35 | 335,830 | 2.63 | 293,781 | 1.68 | 257,845 | 1.90 | | |
| BioRad Cardiac 3 | | 850,373 | 2.54 | 968,163 | 4.55 | 806,724 | 4.27 | 704,609 | 3.35 | 622,327 | 2.85 | | |
| Serum Pool 1 | | 132,116 | 1.96 | 134,352 | 2.61 | 115,440 | 2.80 | 88,671 | 2.92 | 85,439 | 2.70 | | |
| Serum Pool 2 | | 460,096 | 2.13 | 516,783 | 3.49 | 434,533 | 2.96 | 360,241 | 2.66 | 325,185 | 2.48 | | |

FIG. 6H

| Sample | Assigned Conc. (mIU/ml) | LP-530 | | SMS-PEG | | | | SMS-Triton | | | |
|---|---|---|---|---|---|---|---|---|---|---|---|
| | | L5 Mean RLU | %CV | L2 Mean RLU | %CV | L5 Mean RLU | %CV | L2 Mean RLU | %CV | L5 Mean RLU | %CV |
| S0 | 0 | 13,476 | 7.14 | 4,586 | 7.34 | 4,890 | 2.14 | 5,428 | 0.73 | 5,006 | 0.96 |
| S1 | 5 | 28,870 | 0.91 | 16,776 | 2.06 | 16,330 | 2.061 | 17,238 | 7.89 | 16,148 | 6.69 |
| S2 | 26.2 | 98,270 | 0.72 | 70,358 | 2.07 | 64,794 | 1.27 | 65,718 | 3.66 | 59,358 | 3.81 |
| S3 | 147 | 510,260 | 1.80 | 424,176 | 7.80 | 377,782 | 6.374 | 341,376 | 0.37 | 290,672 | 0.49 |
| S4 | 495 | 1,626,792 | 0.20 | 1,251,374 | 0.42 | 1,137,778 | 2.338 | 1,113,174 | 1.89 | 882,510 | 2.03 |
| S5 | 1000 | 3,340,748 | 2.39 | 2,762,594 | 6.14 | 2,602,746 | 6.083 | 2,203,734 | 2.68 | 1,754,734 | 1.53 |
| BioRad-01 | | 28,885 | 4.50 | 15,363 | 2.19 | 14,640 | 1.622 | 14,781 | 6.14 | 13,925 | 4.83 |
| BioRad-02 | | 93,649 | 2.09 | 63,827 | 2.54 | 56,275 | 1.794 | 57,623 | 4.04 | 52,214 | 3.71 |
| BioRad-03 | | 877,765 | 7.15 | 715,919 | 6.40 | 645,727 | 6.301 | 599,509 | 2.64 | 497,783 | 2.66 |
| Negative Patient | | 15,523 | 3.48 | 6,125 | 3.62 | 6,354 | 4.131 | 5,779 | 4.62 | 5,260 | 3.42 |

FIG. 6I

| Sample | Assigned Conc. (mIU/ml) | Total BHCG (New) | | | | | | | | |
|---|---|---|---|---|---|---|---|---|---|---|
| | | LP-530 | | SMS-PEG | | | | SMS-Triton | | |
| | | L5 | | L2 | | L5 | | L2 | | L5 | |
| | | Mean RLU | % CV | Mean RLU | % CV | Mean RLU | % CV | Mean RLU | % CV | Mean RLU | % CV |
| S0 | 0 | 11,004 | 1.59 | 2,544 | 2.22 | 3,144 | 2.70 | 2,392 | 3.07 | 2,796 | 2.63 |
| S1 | 6 | 57,048 | 0.25 | 16,204 | 1.57 | 16,028 | 0.18 | 14,754 | 1.09 | 13,112 | 0.82 |
| S2 | 35.7 | 268,828 | 1.81 | 80,536 | 1.00 | 73,972 | 1.02 | 74,440 | 0.04 | 60,814 | 0.57 |
| S3 | 192 | 1,380,960 | 0.33 | 448,594 | 0.09 | 398,472 | 0.70 | 396,886 | 0.32 | 305,908 | 1.43 |
| S4 | 608 | 4,342,698 | 0.76 | 1,401,896 | 1.49 | 1,244,124 | 1.87 | 1,199,134 | 1.39 | 894,462 | 1.03 |
| S5 | 1341 | 7,976,348 | 0.14 | 2,776,214 | 2.31 | 2,555,860 | 3.20 | 2,402,560 | 1.49 | 1,814,310 | 1.30 |
| BioRad-01 | | 45,193 | 2.01 | 12,580 | 2.12 | 12,137 | 1.41 | 11,503 | 0.66 | 10,480 | 1.64 |
| BioRad-02 | | 189,485 | 1.54 | 57,963 | 2.82 | 51,755 | 4.09 | 50,477 | 1.79 | 42,410 | 2.47 |
| BioRad-03 | | 2,138,746 | 2.20 | 689,205 | 3.45 | 600,122 | 3.23 | 549,013 | 4.25 | 420,735 | 3.98 |
| Negative Patient | | 11,702 | 0.84 | 2,843 | 7.90 | 3,398 | 5.19 | 2,543 | 2.33 | 2,945 | 1.08 |

FIG. 6J

| Name | pKa @ 25°C | Useable Range | Temperature Coefficient |
|---|---|---|---|
| Tris | 8.06 | 7.0-9.0 | -0.028 |
| TAPS | 8.40 | 7.7-9.1 | 0.018 |
| 221-Amine | 9.69 | 9.0-10.5 | -0.032 |
| AMPSO | 9.00 | 8.5-9.7 | -0.029 |
| CHES | 9.50 | 8.6-10.0 | -0.011 |
| DEA | 8.88 | 7.8-9.9 | -0.025 |
| AMPD | 8.80 | 8.3-9.7 | -0.029 |

FIG. 7

| ASSAY NAME | Time to Result with LP-530 in Mins | Time to Result with Test Substrate in Mins | % Time saved |
|---|---|---|---|
| TSH-fast | 20.6 | 15.3 | 26% |
| TSH-Hypersensitive | 44.6 | 39.3 | 12% |
| FT4 | 27.8 | 22.5 | 19% |
| Ferritin | 30.2 | 24.9 | 18% |
| AccuTnI | 12.8 | 7.5 | 41% |
| VitB12 | 35.6 | 30.3 | 15% |
| PSA | 20.6 | 15.3 | 26% |
| FOL | 35.6 | 30.3 | 15% |
| FT3 | 26 | 20.7 | 20% |
| TBhCG2 | 15.8 | 10.5 | 34% |
| CK-MB | 15.8 | 10.5 | 34% |
| BNP2 | 15.8 | 10.5 | 34% |
| AFP | 15.8 | 10.5 | 34% |
| CEA2 | 24.2 | 18.9 | 22% |
| Dil-hCG2 | 17 | 11.7 | 31% |
| hFSH | 54.2 | 48.9 | 10% |
| PTH-IO | 13.4 | 9.7 | 40% |
| PTH routine | 29 | 24.7 | 18% |
| hLH | 54.2 | 48.9 | 10% |
| Testo | 15.8 | 10.5 | 34% |
| Cortisol | 20.6 | 15.3 | 26% |
| E2 | 35.6 | 30.3 | 15% |
| InhibinA | 49.7 | 44.4 | 11% |

FIG. 13

CHEMILUMINESCENT SUBSTRATES

CROSS-REFERENCE TO RELATED APPLICATION(S)

This application is a U.S. National Stage application of PCT/US2017/040457, filed Jun. 30, 2017, which claims benefit of U.S. Provisional Patent Application No. 62/357,091, filed Jun. 30, 2016, and which applications are hereby incorporated by reference in their entireties. To the extent appropriate, a claim of priority is made to each of the above disclosed applications.

BACKGROUND OF THE INVENTION

Field of the Invention

Alkaline phosphatase chemiluminescent substrate formulations are provided exhibiting rapid incubation periods and improved stability for use in immunoassays.

Description of the Related Art

Alkaline phosphatases are hydrolytic enzymes which can be used as markers or labels in enzyme-linked immunoassays. Chemiluminescent detection of these enzymes offers a safe, convenient and sensitive means to provide a quantitative measure of the amount of enzyme in a sample or of the amount of an enzyme-labeled analyte.

Alkaline phosphatase chemiluminescent substrates are used as detection systems in immunoassays. In some formats, the analyte may be labeled with a phosphatase enzyme or can be specifically detected through phosphatase-labeled specific "binding partners". The phosphatase can be incorporated directly as the label on the analyte binding compound. Alternately, the analyte binding compound can be bound to at least one phosphatase-labeled specific binding substance for the analyte binding compound. Alternately, the analyte binding compound can be labeled with at least one second specific binding substance which is then bound to a phosphatase-labeled binding partner for the second specific binding substance. Depending on a variety of factors including performance and stability, some substrates are more useful on automated immunoassay systems.

Compounds (or analytes) that produce chemiluminescence when contacted with an alkaline phosphatase enzyme are disclosed in U.S. Pat. Nos. 6,045,727; 6,090,571; 6,139,782; 6,218,137; 6,270,695; and 6,296,787, each of which is incorporated herein by reference.

LUMI-PHOS 530® (Lumigen, Southfield, Mich.) is a commercial alkaline phosphatase chemiluminescent substrate formulation used in automated immunoassay systems including DxI and Access Systems (Beckman Coulter, Brea Calif.). LUMI-PHOS 530® has desirable sensitivity, open bottle stability, background chemiluminescence, and calibration curve drift, but requires 5-6 minutes incubation time for signal generation on those automated systems. A faster turnaround time (TAT) on those automated systems is desirable.

Lumigen APS-5 (Lumigen, Southfield, Mich.) is another commercial alkaline phosphatase substrate formulation. Lumigen APS-5 is an acridan based chemiluminescent substrate composition used for ELISA detection of alkaline phosphatase (AP) conjugate molecules. Lumigen APS-5 provides less temperature sensitive light output and more rapid peak intensity than LUMI-PHOS 530®. Light emission is maximal at 450 nm. Lumigen APS-5 exhibits rapid incubation periods and good sensitivity, but is not amendable for use on automated immunoassay systems because of somewhat limited open bottle stability, background chemiluminescence, and calibration curve drift. Thus APS-5 suffers from loss of signal intensity during storage and increased thermal sensitivity compared to LUMI-PHOS 530®. As shown in FIG. 1, APS-5 exhibits ca. 35% signal loss over 12 months when stored at 4° C.

It would be desirable to have an alkaline phosphate substrate with the fast turnaround times exhibited by APS-5 while at the same time exhibiting a longer shelf-life and improved stability of LUMI-PHOS 530® to improve the performance and efficiency of automated immunoassay systems.

SUMMARY

Alkaline phosphatase chemiluminescent substrate formulations ("substrate formulations") are provided for use in immunoassay systems, particularly in automated immunoassay systems. These aqueous substrate formulations produce chemiluminescence in the presence of a phosphatase enzyme. In some embodiments, improved substrate formulations are provided that exhibit rapid signal generation. The present substrate formulations provide one or more of improved signal generation time (or turnaround time), improved stability (e.g. reduced thermal sensitivity), enhanced alkaline phosphatase specificity, and/or enhanced assay sensitivity compared to current commercial substrate formulations.

In some embodiments, the substrate formulation comprises:
a) a chemiluminescent compound of formula I or a salt thereof:

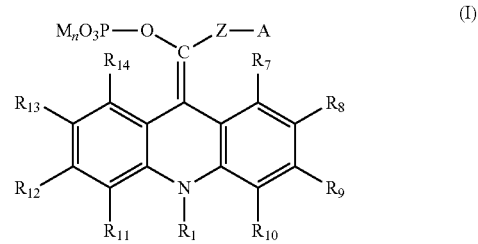

wherein
A is $C_{1-6}$ haloalkyl, naphthyl, phenyl, substituted phenyl, or heteroaryl, wherein substituted phenyl comprises from 1 to 3 halo, $C_{1-6}$ alkyl, $C_{1-6}$ alkoxy, $C_{1-6}$ haloalkyl, $C(O)R_{15}$, CN or $NO_2$ substituents; $R_1$ is selected from the group consisting of $C_{5-14}$ aryl, $C_{1-6}$ alkyl, $C_{1-6}$ haloalkyl, and $C_{5-14}$ aralkyl groups; $R_7$-$R_{14}$ are independently H, $C_{1-6}$ alkoxy, halo, or $C_{1-6}$ alkyl, or $R_7$-$R_8$ or $R_8$-$R_9$ or $R_9$-$R_{10}$ $R_{11}$-$R_{12}$ or $R_{12}$-$R_{13}$ or $R_{13}$-$R_{14}$, can be joined together as a carbocyclic or heterocyclic ring system comprising at least one 5 or 6-membered ring; $R_{15}$ is $C_{1-6}$ alkyl; each M is independently selected from H, or an alkali metal, alkaline earth metal, transition metal, ammonium, phosphonium, salt formed from organic amine, or amino acid; Z is O or S; and n is 0, 1, or 2;
b) a cationic aromatic compound in an amount effective to increase the chemiluminescence compared to that generated in the absence of the cationic aromatic compound;
c) a background reducing agent; and d) an ether-linked non-ionic surfactant or a hydrophilic polymer.

In some embodiments, the substrate formulation comprises (a) 0.01 mM-50 mM compound I, (b) 0.01-200 uM cationic aromatic compound, (c) 1 uM-10 mM background reducing agent, and (d) 0.05-20 g/L ether-linked nonionic surfactant or hydrophilic polymer.

In some embodiments, the substrate formulation comprises compound I wherein Z is S; Ar is phenyl or substituted phenyl, wherein substituted phenyl comprises from 1 to 3 halo, $C_{1-6}$ alkyl, $C_{1-6}$ alkoxy, and $C_{1-6}$ haloalkyl substituents; $R_1$ is methyl, ethyl, propyl, isopropyl, n-butyl, sec-butyl or t-butyl; $R_7$-$R_{14}$ are independently H, $C_{1-6}$ alkoxy, halo; each M is Na or H; and n is 0, 1, or 2.

In specific embodiments, the substrate formulation comprises a compound I selected from the group consisting of

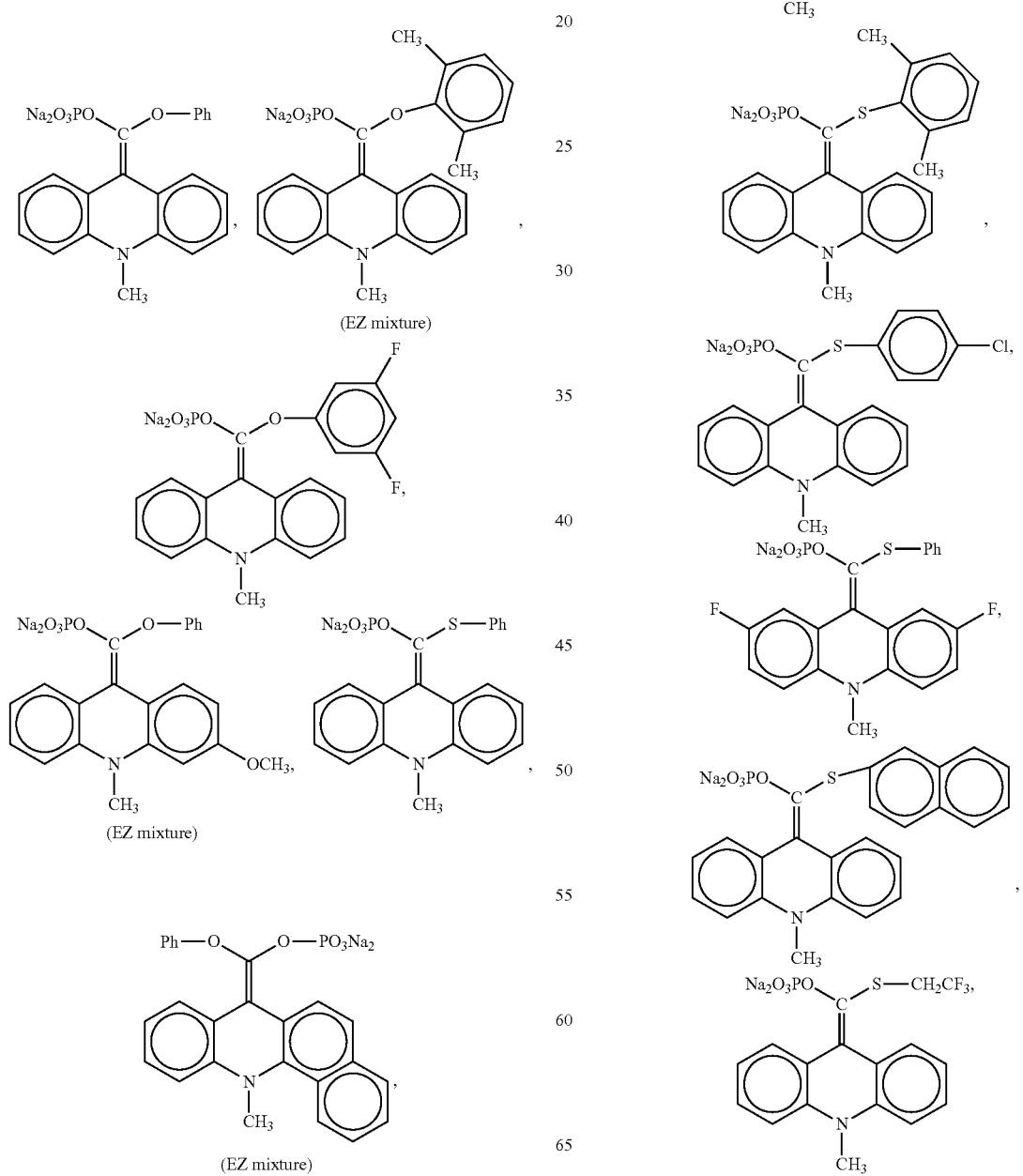

-continued

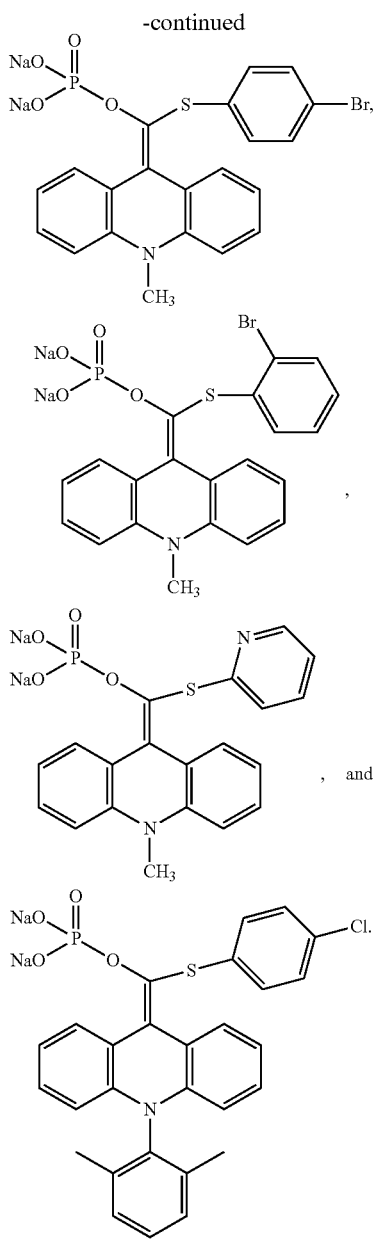

In some embodiments, a substrate formulation comprises a cationic aromatic compound (CAC) II:

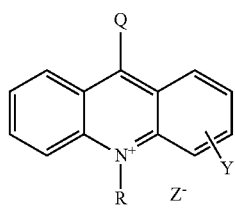

(II)

wherein Q is selected from the group consisting of halogen, cyano, —COOR', —COSR', —CONR¹R$_2$, —CON(R)SO$_2$R", naphthyl, anthryl, N—C$_{1-4}$ alkyl acridinyl, halo substituted N—C$_{1-4}$ alkyl acridinyl; R is C$_{1-4}$ alkyl; R', R" are independently selected from C$_{1-6}$ alkyl, aryl, alkyl substituted aryl; R¹, R² are independently selected from H, C$_{1-6}$ alkyl, aryl, and alkylaryl; Z⁻ is a halide or nitrate; and Y is selected from H, halo, C$_{1-4}$ alkyl.

In some embodiments, the substrate formulation comprises a cationic aromatic compound II, wherein Q is N-methyl acridinyl, halo substituted N-methyl acridinyl, naphthyl, or anthryl; R is C$_{1-4}$ alkyl; Z– is selected from the group consisting of Cl⁻, Br⁻, I⁻, NO$_3$⁻, and Y is H or halo.

In specific embodiments, the substrate formulation comprises a cationic aromatic compound II selected from the group consisting of

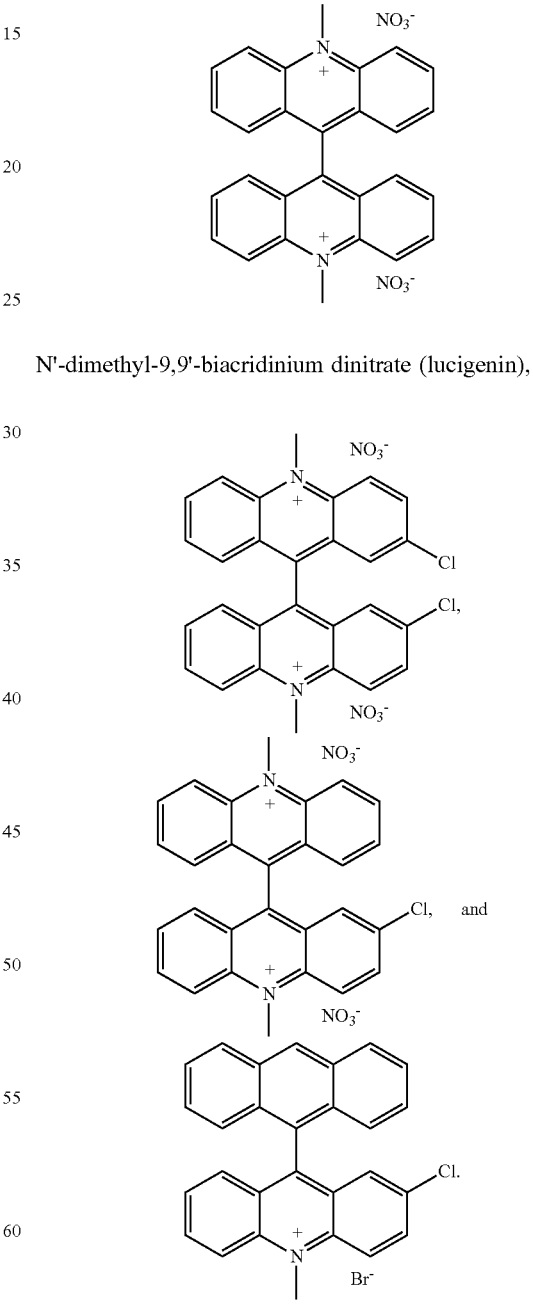

N'-dimethyl-9,9'-biacridinium dinitrate (lucigenin),

In some embodiments, the substrate formulation comprises a cationic aromatic compound II that is N,N'-dimethylbiacridinium dinitrate (lucigenin).

In some embodiments, the substrate formulation comprises a background reducing agent selected from the group consisting of lithium sulfite, sodium sulfite, potassium sulfite, lithium bisulfite, sodium bisulfite, potassium bisulfite, lithium metabisulfite, sodium metabisulfite, potassium metabisulfite, dibutylhydroxytoluene (BHT; 2,6-bis(1,10dimethylethyl)-4-methylphenol), butylated hydroxyl anisole (BHA), 3-t-butyl-4-hydroxyanisole, 3-tert-butyl-4-hydroxyanisole, and an aromatic boronic acid of formula Ar—B(OH)$_2$, wherein Ar is phenyl, substituted phenyl, a fused aromatic ring system that may or may or include heteroatom(s), a substituted fused aromatic ring system that may or may include heteroatom(s), wherein the substituted aryl group may have from 1-3 substituents independently selected from C$_{1-6}$ alkyl, halo, alkoxycarbonyl, or hydroxyl groups. In specific embodiments, the background reducing agent is selected from the group consisting of phenyl boronic acid, 4-tolyl boronic acid, 4-chloroboronic acid, 4-iodoboronic acid and 3-methoxycarbonylphenyl boronic acid, and sodium sulfite.

In some embodiments, a substrate formulation comprises an ether-linked nonionic surfactant according to formula (III):

(III)

wherein R is selected from C$_{6-22}$alkyl, cycloalkyl, C$_{6-22}$alkyl substituted cycloalkyl, and mono- or di-C$_{6-22}$alkyl-substituted phenyl; n is a number from 2-200; X is selected from O or S; and Y is selected from H or C$_{1-4}$ alkyl.

In some embodiments, the substrate formulation comprises an ether-linked nonionic surfactant according to formula (III), wherein R is a C$_{8-20}$alkyl, C$_{8-20}$ substituted cycloalkyl or mono- or di-C$_{8-20}$alkyl-substituted phenyl, n is a number from 8 to 150, X is O, and Y is H.

In some embodiments, the ether-linked nonionic surfactant is selected from a polyoxyethylene glycol alkyl ether (BRIJ), a polyoxyethylene glycol octylphenol ether (TRITON), or a polyoxyethylene nonylphenyl ether (IGEPAL). In specific embodiments, the substrate formulation comprises an ether-linked nonionic surfactant is selected from the group consisting of IGEPAL CO-990, IGEPAL DM-970, TRITON X-405, TRITON X-405 reduced, BRIJ 78, and BRIJ 700.

In some embodiments, the substrate formulation comprises a hydrophilic polymer according to formula (IV):

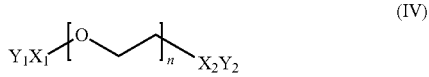

(IV)

wherein X$_1$ and X$_2$ are independently selected from O, S, N or NH, or are absent; Y$_1$ and Y$_2$ are independently selected from H, H$_2$ or C$_{1-4}$ alkyl; and n is a number from 20 to 12,000. In some from 120 to 5,000, or from 250 to 2,500. In some aspects, n is a number>20.

In some embodiments, the substrate formulation comprises a hydrophilic polymer according to formula (IV), wherein X$_1$ and X$_2$ are O; Y$_1$ and Y$_2$ are H; and n is a number>20.

In some embodiments, the substrate formulation comprises a hydrophilic polymer selected from a poly(ethylene glycol) of an average Mw selected from within the range of 1,000 to 511,000; 6,000 to 218,000, or 12,000 to 108,000. In some specific embodiments, the hydrophilic polymer is selected from the group consisting of poly(ethylene glycol) (Mw=14,000), poly(ethylene glycol) (Mw=35,000), and poly(ethylene glycol) (Mw=100,000).

In some embodiments, the substrate formulation further comprises an anionic surfactant selected from the group consisting of C$_{10-22}$ alkyl sulfate and C$_{10-22}$ alkyl sulfonate. In specific embodiments, the substrate formulation comprises an anionic surfactant selected from the group consisting of sodium dodecyl sulfate (SDS), sodium tridecyl sulfate (STS), and sodium tetradecyl sulfate. When present, the substrate formulation contains 0.01-10 g/L, preferably 0.1 to 5 g/L of anionic surfactant.

In some embodiments, the substrate formulation further comprises an amine buffer at a pH from 7-12, preferably 8-11. In specific embodiments, the amine buffer is selected from Tris (tromethamine); AMPD(2-amino-2-methyl-1,3-propanediol); DEA (diethanolamine); AMPSO(N-(1,1-Dimethyl-2-hydroxyethyl)-3-amino-2-hydroxypropanesulfonic acid); 221-Amine (2-amino-2-methylpropan-1-ol); CHES (2-(N-cyclohexylamino)ethanesulfonic acid); glycine; or TAPS (N-Tris(hydroxymethyl)methyl-3-aminopropanesulfonic acid) buffer at pH 7-12. In specific embodiments, the substrate formulation comprises an amine buffer selected from Tris (tromethamine), or AMPD(2-amino-2-methyl-1,3-propanediol).

In some specific embodiments, the substrate formulation comprises 0.01 mM-50 mM compound I, 0.01-200 uM cationic aromatic compound, 1 uM-10 mM background reducing agent, 0.05-20 g/L ether-linked non-ionic surfactant or hydrophilic polymer, 0.01-10 g/L anionic surfactant, and an amine buffer at pH 7-12.

In some specific embodiments, the substrate formulation comprises 0.05 mM-10 mM compound I, 0.05-50 µM cationic aromatic compound, 10 uM-1000 uM background reducing agent, 0.1 to 10 g/L ether-linked non-ionic surfactant or hydrophilic polymer, 0.1 to 5 g/L anionic surfactant, and an amine buffer at pH 8-11.

In some specific embodiments, the substrate formulation, compound I is CPA (((4-chlorophenyl)thio)(10-methylacridin-9(1 OH)-ylidene)methyl phosphate, disodium salt); the CAC is lucigenin; the background reducing agent is sodium sulfite; the non-ionic surfactant is selected from IGEPAL (CO-990, DM-970), TRITON (X-405, X-405 reduced), and BRIJ (78, 700); the anionic surfactant is SDS or STS; and the amine buffer is TRIS or AMPD.

In some specific embodiments, the substrate formulation comprises CPA; lucigenin; sodium sulfite; a hydrophilic polymer selected from poly(ethylene glycol) (Mw=14,000), poly(ethylene glycol) (Mw=35,000), and poly(ethylene glycol) (Mw=100,000); an anionic surfactant which is SDS or STS; and an amine buffer which is TRIS or AMPD.

In some embodiments, the substrate formulation comprises 0.01 mM-50 mM compound I, 0.01-200 uM cationic aromatic compound, 1 uM-10 mM background reducing agent, 0.05-20 g/L ether-linked non-ionic surfactant or hydrophilic polymer, 0.01-10 g/L anionic surfactant, and an amine buffer at pH 7-12, wherein the composition exhibits one or more of:

a) maximum intensity (Imax) in ≤5 minutes, ≤4 minutes, ≤2 minutes, ≤1 minute, ≤45 seconds, ≤30 seconds, ≤20 seconds, ≤10 seconds, ≤5 seconds, ≤4 seconds, ≤3 seconds, or ≤2 seconds after exposure to an alkaline phosphatase enzyme;

b) ≤10% loss of original RLU after exposure to an alkaline phosphatase enzyme after storage at 4° C. for 300 days;

c) ≥90%, or >95% retained activity (RLU), compared to original RLU, when stored at 4° C. for 300 days or more;

d) ≥90% retained activity when stored at 4° C. for 400 days or more; and e) a signal change in (%) per day after 15 days when stored at 30° C. of <–0.50%/day.

In some embodiments, a method is provided for detecting an analyte in a sample by a chemiluminescent assay procedure which comprises:

(a) contacting a sample with the substrate formulation of the present invention, and (b) measuring chemiluminescence, wherein the presence of chemiluminescence correlates with the presence of analyte.

In some embodiments of the method of the present invention, the analyte is a phosphatase enzyme, or an inhibitor of a phosphatase enzyme. In some embodiments, the method further comprises reacting the analyte in the sample with an analyte binding compound which specifically binds with the analyte wherein the analyte-binding compound is labeled with alkaline phosphatase. In some embodiments, the analyte-binding compound is selected from the group consisting of antibodies, antigens, haptens and nucleic acids. In some embodiments, the method further comprises reacting the analyte in the sample with an analyte binding compound which specifically binds with the analyte and at least one phosphatase-labeled specific binding substance for the analyte binding compound.

In some embodiments of the method, the turnaround time (TAT) from when compound I is contacted with phosphatase enzyme to when chemiluminescence occurs is less than 2 minutes in an automated immunoassay or Performance Test B.

BRIEF DESCRIPTION OF THE DRAWINGS

FIG. 5 shows commercial assays and assay formats employed in Substrate Assay Screening with substrate formulations SMS-PEG and SMS-TRITON containing 0.15 g/L CPA compared to commercial LUMI-PHOS® 530 AP substrate, as described in Example 6.

FIG. 6A shows Digoxin Screening RLU data at L2 (27 sec) and L5 (6.3 min) for both SMS-PEG and SMS-TRITON substrate formulations compared to RLU for LUMI-PHOS® 530 at L5 (6.3 min).

FIG. 6B shows PTH (IO) RLU data at L2 (27 sec) and L5 (6.3 min) for both SMS-PEG and SMS-TRITON substrate formulations compared to RLU for LUMI-PHOS® 530 at L5 (6.3 min).

FIG. 6C shows TSH (Current) screening RLU data at L2 (27 sec) and L5 (6.3 min) for both SMS-PEG and SMS-TRITON substrate formulations compared to RLU for LUMI-PHOS® 530 at L5 (6.3 min).

FIG. 6D shows TSH2 RLU data at L2 (27 sec) and L5 (6.3 min) for both SMS-PEG and SMS-TRITON substrate formulations compared to RLU for LUMI-PHOS® 530 at L5 (6.3 min).

FIG. 6E shows AccuTnI+3 screening RLU data at L2 (27 sec) and L5 (6.3 min) for both SMS-PEG and SMS-TRITON substrate formulations compared to RLU for LUMI-PHOS® 530 at L5 (6.3 min).

FIG. 6F shows BNP screening RLU data at L2 (27 sec) and L5 (6.3 min) for both SMS-PEG and SMS-TRITON substrate formulations compared to RLU for LUMI-PHOS® 530 at L5 (6.3 min).

FIG. 6G shows CK-MB screening RLU data at L2 (27 sec) and L5 (6.3 min) for both SMS-PEG and SMS-TRITON substrate formulations compared to RLU for LUMI-PHOS® 530 at L5 (6.3 min).

FIG. 6H shows Myoglobin screening RLU data at L2 (27 sec) and L5 (6.3 min) for both SMS-PEG and SMS-TRITON substrate formulations compared to RLU for LUMI-PHOS® 530 at L5 (6.3 min).

FIG. 6I shows Total BHCG (old) screening RLU data at L2 (27 sec) and L5 (6.3 min) for both SMS-PEG and SMS-TRITON substrate formulations compared to RLU for LUMI-PHOS® 530 at L5 (6.3 min).

FIG. 6J shows total BHCG (New) screening RLU data at L2 (27 sec) and L5 (6.3 min) for both SMS-PEG and SMS-TRITON substrate formulations compared to RLU for LUMI-PHOS® 530 at L5 (6.3 min).

FIG. 7 shows characteristics of amine buffers investigated for use in substrate formulations of the present invention.

FIG. 13 shows time to result in 23 automated immunoassays for the substrate formulation of Example 23 compared to the commercial LUMI-PHOS® 530. The substrate formulation of Example 23 saved from 10% to 40% time in the automated immunoassays compared to LUMI-PHOS® 530.

DETAILED DESCRIPTION

Figure 1:
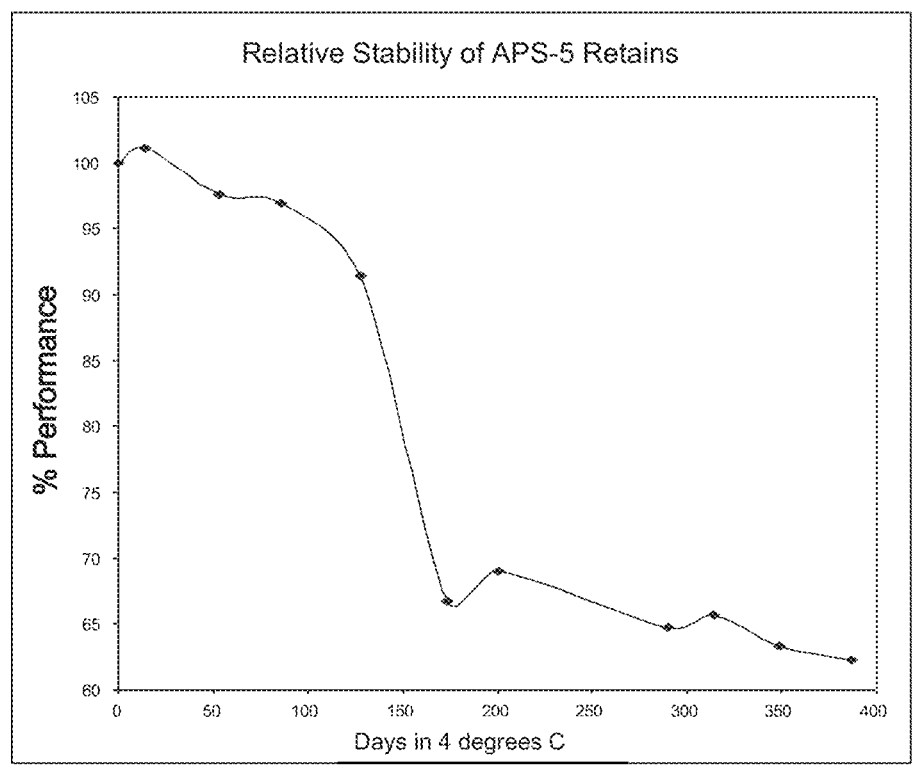
FIG. 1 shows relative stability of APS-5 substrate formulation retains in terms of percent of original performance intensity over time when stored at 4° C. for about 400 days.

The disclosure provides improved substrate formulations that react with an alkaline phosphatase to rapidly produce a chemiluminescent signal, and that exhibit sustained signal stability during storage. In some embodiments, the substrate formulations exhibiting faster turnaround time (TAT), and one or more of reduced thermal sensitivity, enhanced ALP assay specificity, reduction in fliers, and increased assay sensitivity as compared to commercially available substrates containing compounds such as LUMI-PHOS 530®. Such substrate formulations are desirable for use in both manual and automated immunoassays and other assays that use alkaline phosphatase substrates, such as nucleic acid probe assays, cell receptor assays, etc.

Definitions

The terms "a" and "an" refer to "one or more" of the enumerated components. For example, "a" cationic aromatic compound refers to one or a mixture comprising two or more cationic aromatic compounds. Any concentration range, percentage range, or ratio range recited herein are to be understood to include concentrations, percentages, or ratios of any integer within that range and fractions thereof, such as one tenth and one hundredth of an integer, unless otherwise indicated. Also, any number range recited herein relating to any physical feature are to be understood to include any integer within the recited range, unless otherwise indicated.

The term "chemiluminescent compound" refers to a compound that produces chemiluminescence in the presence of a phosphatase enzyme and oxygen under appropriate conditions as provided herein. The chemiluminescent compound in the substrate formulations of the present invention are of formula I described herein.

The term "analyte" means a substance whose presence can be detected or quantified in a sample. Analytes which can be assayed by the present methods include phosphatase enzymes, in which case it would be unnecessary to add additional phosphatase enzyme. The analyte can be an inhibitor of a phosphatase enzyme. The analyte can be any of various classes of organic and biological molecules which can be detected in ligand-binder assays as are generally known in the art and include immunoassays, nucleic acid probe assays, cell receptor assays and the like.

The term "background reducing agent" refers to a compound whose presence reduces chemiluminescence produced in the absence of a phosphatase enzyme.

The term "cationic aromatic compound" (CAC) refers to a compound comprising a heteroaromatic ring compound comprising one or more isolated or fused aromatic rings and containing at least one atom other than carbon (heteroatom), preferably one or more nitrogen atoms in which the positive charge is substantially localized on one or more of the heteroatoms. CAC compounds have oxidation/reduction potentials suitable for causing an increase in chemiluminescence in phosphatase reactions as provided herein.

The term "ether-linked nonionic surfactant" refers to a nonionic organic compound containing hydrophobic and hydrophilic groups connected by or comprising an ether linkage. The ether-linked nonionic surfactant does not contain a sulfate, sulfonate, phosphate or carboxylate ester group. In some embodiments, the ether-linked nonionic surfactant is a compound according to formula (III):

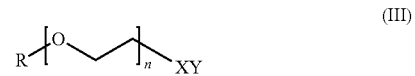

(III)

wherein R is selected from $C_{6-22}$alkyl, cycloalkyl, $C_{6-22}$alkyl-substituted cycloalkyl, and mono- or di-$C_{6-22}$alkyl-substituted phenyl; n is a number from 2-200; X is selected from O or S; and Y is selected from H or $C_{1-4}$ alkyl.

In some embodiments, the ether-linked nonionic surfactant is selected from a polyoxyethylene glycol alkyl ether (BRIJ), a polyoxyethylene glycol octylphenol ether (TRITON), or polyoxyethylene nonylphenyl ether (IGEPAL). Further examples of ether-linked nonionic surfactants are provided herein.

The term "ester-linked nonionic surfactant" refers to a nonionic organic compound containing hydrophobic and hydrophilic groups connected by or comprising an ester linkage. Examples of ester-linked nonionic surfactants include polyoxyethylene glycol sorbitan esters (Polysorbates, TWEENs), sorbitan alkyl esters (Spans). Further examples of ether-linked nonionic surfactants are further provided herein.

The term "flier", "fliers", "flyer", or "flyers" refers to a false-positive immunoassay result. A reduction in flyers is desirable to avoid unnecessary procedures, and repeated testing.

The term "hydrophilic polymer" refers to a polymer having repeating $C_{2-3}$ alkyl ether functionalities without a hydrophobic aryl or >$C_4$ alkyl group. The hydrophilic polymer does not contain a sulfate, sulfonate, phosphate or carboxylate ester group. In some embodiments, the hydrophilic polymer is selected from a poly(ethylene glycol) (PEG), or a poly(propylene glycol) (PPG). In a preferred embodiment, the hydrophilic polymer is a poly(ethylene glycol) having an average Mw selected in the range of 1,000 to 511,000. In some embodiments, the hydrophilic polymer is nonionic. Further examples of hydrophilic polymers are provided herein.

The term "homogenous assay" refers to solution phase, homogeneous methods that utilize an analyte-specific binding reaction to modulate or create a detectable signal without requiring a separation step between analyte-specific and analyte non-specific reactants. In some embodiments, the compositions and methods provided herein are amenable for use in homogenous solution phase assays. In some embodiments, the compositions and methods provided herein are amenable for use in solution phase immunoassays.

The term "heterogenous assay" refers to heterogeneous formats that rely on physical separation of analyte-bound and free (not bound to analyte) detectably labeled specific binding partners. Separation typically requires that critical reactants be immobilized onto some type of solid substrate so that some type of physical process can be employed, e.g. filtration, settling, agglomeration or magnetic separation, and typically also require wash steps to remove the free detectably labeled specific binding partners.

In some embodiments, the compositions and methods provided herein are amenable for use in heterogenous assays. In some embodiments, the compositions and methods provided herein are amenable for use in heterogenous immunoassays.

Where compounds of formula I are sufficiently acidic, "salts thereof" are base salts. In some embodiments, compound I comprises M selected from an alkali metal, alkaline earth metal, transition metal, ammonium, organic amine salt, amino acid salt or a phosphonium salt. Examples of compound I include but are not limited to, an alkali metal salt for example where M is selected from sodium, potassium, or lithium, an alkaline earth metal salt, for example, where M is calcium or magnesium, a transition metal salt such as where M is zinc, an ammonium salt such as where M is an ammonium ion $NH_4$, or a primary, secondary, tertiary or quaternary ammonium salt, for example, derived from an organic amine selected from for example triethylamine, ethanolamine, diethanolamine, triethanolamine, morpholine, N-methylpiperidine, N-ethylpiperidine, dibenzylamine, an amino acid salt such as a glycine, or lysine salt, or a phosphonium salt.

Examples of phosphonium salts include but are not limited to water soluble polymeric phosphonium salts, including water soluble polyvinyl phosphonium salt polymers, as disclosed in U.S. Pat. No. 5,393,469, which is incorporated herein by reference. Examples of ammonium salts also include poly(vinyl quaternary ammonium salts), as described in U.S. Pat. No. 4,978,614, which is incorporated herein by reference. In some embodiments, compound I comprises an M selected from H, Na, K, Li, Ca, Mg, Zn, $NH_4$, $HNEt_3$, $HO(CH_2)_2NH_4$, $[HO(CH_2)_2]_2NH_2$, $[HO(CH_2)_2]_3NH$, morpholinium, N-methylpiperidinium, N-ethylpiperidinium, dibenzylammonium, glycine, or lysine salts. In some embodiments, compound I comprises wherein each M is independently selected from the group consisting of H, Na, K, and Li. In some embodiments, each M is independently selected from H and Na.

The phrase "optionally substituted" is used interchangeably with the phrase "substituted or unsubstituted." Unless otherwise indicated, an optionally substituted group may have a substituent at each substitutable position of the group, and each substitution is independent of any other. Also, combinations of substituents or variables are permissible only if such combinations result in stable compounds. In addition, unless otherwise indicated, functional group radicals are independently selected. Where "optionally substituted" modifies a series of groups separated by commas (e.g., "optionally substituted A, B or C"; or "A, B or C optionally substituted with"), it is intended that each of the groups (e.g., A, B and C) is optionally substituted.

The term "PMP" refers to an assay support comprising a microparticle. In a specific embodiment, the microparticle comprises a paramagnetic or superparamagnetic material such as, for example, ferromagnetic iron oxide $Fe_3O_4$ or $Fe_2O_3$. The terms "paramagnetic" and "superparamagnetic" refer to materials that experience a force in a magnetic field gradient, but do not become permanently magnetized. In a specific embodiment, the support comprises iron in the form of maghemite, or $Fe_2O_3$. In various embodiments, the mean diameter of the microparticle is in the range of 100 nm to 22,900 nm. In a specific embodiment, the mean diameter of the microparticle is in the range of about 750 nm to about 3,000 nm. In another specific embodiment, the mean diameter of the microparticle is in the range of about 950 nm to about 1,150 nm.

The term "RLU" refers to relative light units in terms of chemiluminescence signal (S) in the presence of AP. In some aspects, RLU may be corrected for background chemiluminescence (B) in the absence of AP, e.g., S—B.

The term "TAT" refers to turnaround time from the time the alkaline phosphatase substrate is activated by (contacted with) alkaline phosphatase to the time to generation of luminescence signal plateau in Performance Test B or an automated AP immunoassay. Typically, for substrate formulations of the present invention the TAT time is at least 2 times faster compared to LUMI-PHOS 530®; preferably at least 5 times faster. Alternatively, the TAT time is less than 2 minutes, preferably less than 1 minute, more preferably less than 30 s, most preferably less than 10 s. Reduction in turnaround time (TAT) is desirable because it can lead to increased patient satisfaction, increased patient flow, less wasted time, and decreased patient harm.

The term "improved stability" refers to an AP substrate formulation that exhibits greater stability than standard APS-5 substrate formulation, or less than about 35% signal loss when stored at 4° C. over 12 months and tested by Stability Test A.

The term "reduced thermal sensitivity" when referring to substrate formulations of the disclosure means decreased loss of compound I as measured by Fluorescence Change % per Day after storage for 15 Days at 30° C. compared to day 0, when compared to APS-5 substrate. In some embodiments, substrate formulations of the disclosure exhibit less than 0.25% loss in fluorescence per day, less than 0.20% loss in fluorescence per day, or preferably less than 0.10% loss in fluorescence per day after storage for 15 Days at 30° C., compared to APS-5 that exhibits 0.265% loss per day, as shown in Example 9, Table 24.

The term "enhanced assay specificity" in reference to the substrate formulations provided herein refers to fewer false positives, or a reduced number of fliers, for a particular analyte in an alkaline phosphatase assay than those obtained using APS-5 in the same AP assay.

The term "enhanced assay sensitivity" when referring to substrate formulations of the disclosure means higher S0/blank ratios compared to those of LUMI-PHOS® 530. As shown in Example 6K, the S0/blank ratios with substrate test formulations were higher than those with LUMI-PHOS® 530 in the same assay.

The term "higher signal to noise" when referring to substrate formulations of the disclosure refers to higher calibrator signal to noise ratios in an AP assay than LP-530 substrate in the same assay. In one aspect, the calibrator signal to noise ratio may be calculated as an S/S0 value, where "S" is chemiluminescence assay signal with a calibrator containing analyte, and "S0" is chemiluminescence assay signal using the same assay format with a calibrator in absence of analyte. As shown in each of examples 6B-6J, Tables 7-15, substrate formulations of the disclosure exhibit higher calibrator signal to noise ratios than LP-530 substrate.

Chemical Definitions

The term "aliphatic" or "aliphatic group" as used herein means a straight-chain or branched $C_{1-12}$ hydrocarbon chain that is completely saturated or that contains one or more units of unsaturation, or a monocyclic $C_{3-8}$ hydrocarbon or bicyclic $C_{8-12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched alkyl, alkenyl, alkynyl groups and hybrids thereof such as (cycloalkyl)alkyl, (cycloalkenyl)alkyl or (cycloalkyl)alkenyl.

The terms "alkyl," "alkoxy," "hydroxyalkyl," "alkoxyalkyl" and "alkoxycarbonyl," used alone or as part of a larger moiety include both straight and branched chains containing one to twenty-two carbon atoms ($C_{1-22}$), unless otherwise specified. The terms "alkenyl" and "alkynyl" used alone or as part of a larger moiety shall include both straight and branched chains containing two to twelve carbon atoms.

The term "aryl" used alone or in combination with other terms, refers to monocyclic, bicyclic or tricyclic carbocyclic ring systems having a total of five to fourteen ring members, wherein at least one ring in the system is aromatic and wherein each ring in the system contains 3 to 8 ring members. The term "aryl" may be used interchangeably with the term "aryl ring". The term "aralkyl" refers to an alkyl group substituted by an aryl. The term "aralkoxy" refers to an alkoxy group substituted by an aryl. In some embodiments, aryl is phenyl or naphthyl and may be optionally substituted as shown herein.

The terms "haloalkyl," "haloalkenyl" and "haloalkoxy" means alkyl, alkenyl or alkoxy, as the case may be, substituted with one or more halogen atoms.

The term "halogen" or "halide" or "halo" means F, Cl, Br or I.

The term "heteroatom" means nitrogen, oxygen, or sulfur and includes any oxidized form of nitrogen and sulfur, and the quaternized form of any basic nitrogen.

The term "heterocyclic ring system" as used herein means monocyclic, or bicyclic or tricyclic fused ring system, having 5, 6, 7, 8, 9, 10, 11, 12, 13 or 14 ring members in which one or more ring members is a heteroatom, wherein each ring in the system contains 3, 4, 5, 6, 7 or 8 ring members. In some embodiments, the heterocyclic ring system comprises a "heteroaryl," used alone or in combination with other terms, refers to monocyclic, bicyclic and tricyclic ring systems having a total of 5, 6, 7, 8, 9, 10, 11, 12, 13 or 14 ring members, and wherein: 1) at least one ring in the system is aromatic; 2) at least one ring in the system contains one or more heteroatoms; and 3) each ring in the system contains 3, 4, 5, 6 or 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, benzoacridinyl, and benzoisoxazolyl. The term "heteroaralkyl" refers to an alkyl group substituted by a heteroaryl. The term "heteroarylalkoxy" refers to an alkoxy group substituted by a heteroaryl.

In some aspects, the "heterocyclic ring system" refers to an optionally substituted heterocyclic system containing at least one five or six-membered ring which comprises at least one heteroatom selected from N, O and S atoms. In some aspects, the heterocyclic ring system comprises at least one five or six-membered heterocyclic ring containing only one N atom as the heteroatom. In a preferred embodiment the heterocyclic ring system comprises an acridan ring system. In one aspect, the heterocyclic ring system comprises an N—$C_{1-4}$alkylacridan ring system or a substituted N—$C_{1-4}$alkylacridan ring system. The substituted heterocyclic ring system comprises 1-4 substituents selected from $C_{1-4}$ alkyl, halo, $C_{1-4}$alkoxy, or one or two fused benzo substituents. In a specific aspect, the heterocyclic ring system comprises an N-methylacridan ring system.

An "aryl" (including aralkyl, aralkoxy, aryloxyalkyl and the like) or "heteroaryl" (including heteroaralkyl, heteroarylalkoxy and the like) group may contain one or more substituents. Suitable substituents on an unsaturated carbon atom of an aryl, heteroaryl, aralkyl or heteroaralkylgroup are selected from halogen; haloalkyl; —$CF_3$; —R; —OR; —SR; 1,2-methylenedioxy; 1,2-ethylenedioxy; protected OH (such as acyloxy); phenyl (Ph); Ph substituted with R; —O(Ph); —O—(Ph) substituted with R; —$CH_2$(Ph); —$CH_2$(Ph) substituted with R; —$CH_2CH_2$(Ph); —$CH_2CH_2$(Ph) substituted with R; —$NO_2$; —CN; —$N(R)_2$; —NRC(O)R; —NRC(O)N$(R)_2$; —$NRCO_2$R; —NRNRC(O)R; —NR—NRC(O)N$(R)_2$; —$NRNRCO_2$R; —C(O)C(O)R; —C(O)$CH_2$C(O)R; —$CO_2$R; —C(O)R; —C(O)N$(R)_2$; —OC(O)N$(R)_2$; —$S(O)_2$R; —$SO_2$N$(R)_2$; —S(O)R; —$NRSO_2$N$(R)_2$; —$NRSO_2$R; —C(=S)N$(R)_2$; —C(=NH)—N$(R)_2$; —$(CH_2)_y$NHC(O)R; —$(CH_2)_y$R; —$(CH_2)_y$NHC(O)NHR; —$(CH_2)_y$NHC(O)OR; —$(CH_2)_y$NHS(O)R; —$(CH_2)_y$NHSO_2R; or —$(CH_2)_y$NHC(O)CH((V)z-R)(R) wherein each R is independently selected from hydrogen, optionally substituted aliphatic (preferably $C_{1-6}$), an unsubstituted heteroaryl or heterocyclic ring (preferably $C_{5-6}$), phenyl (Ph), —O(Ph), or —$CH_2$(Ph)—$CH_2$(Ph), wherein y is 0-6; z is 0-1; and V is a linker group. When R is aliphatic, it may be substituted with one or more substituents selected from —$NH_2$, —NH($C_{1-4}$ aliphatic), —N($C_{1-4}$ aliphatic)$_2$, —S(O)($C_{1-4}$ aliphatic), —$SO_2$($C_{1-4}$ aliphatic), halogen, ($C_{1-4}$ aliphatic), —OH, —O—($C_{1-4}$ aliphatic), —$NO_2$, —CN, —$CO_2$H, —$CO_2$($C_{1-4}$ aliphatic), —O(halo $C_{1-4}$ aliphatic) or -halo($C_{1-4}$ aliphatic); wherein each $C_{1-4}$ aliphatic is unsubstituted.

An aliphatic group or a non-aromatic heterocyclic ring may contain one or more substituents. Suitable substituents on a saturated carbon of an aliphatic group or of a non-aromatic heterocyclic ring are selected from those listed above for the unsaturated carbon of an aryl or heteroaryl group and the following: =O, =S, =NNHR, =NN$(R)_2$, =N—, =NNHC(O)R, =NNHCO$_2$(alkyl), =NNHSO$_2$(alkyl), or =NR, where each R is independently selected from hydrogen or an optionally substituted aliphatic (preferably $C_{1-6}$). When R is aliphatic, it may be substituted with one or more substituents selected from —$NH_2$, —NH($C_{1-4}$ aliphatic), —N($C_{1-4}$ aliphatic)$_2$, halogen, —OH, —O—($C_{1-4}$ aliphatic), —$NO_2$, —CN, —$CO_2$H, —$CO_2$($C_{1-4}$ aliphatic), —O(halo $C_{1-4}$ aliphatic), or -halo($C_{1-4}$ aliphatic); wherein each $C_{1-4}$ aliphatic is unsubstituted.

Substituents on a nitrogen of a non-aromatic heterocyclic ring are selected from —R, —N$(R)_2$, —C(O)R, —C(O)OR, —C(O)C(O)R, —C(O)$CH_2$C(O)R, —$SO_2$R, —$SO_2$N$(R)_2$, —C(=S)N$(R)_2$, —C(=NH)—N$(R)_2$ or —$NRSO_2$R; wherein each R is independently selected from hydrogen, an optionally substituted aliphatic (preferably $C_{1-6}$), optionally substituted phenyl (Ph), optionally substituted —O(Ph), optionally substituted —$CH_2$(Ph), optionally substituted —CH$_2$CH$_2$(Ph), or an unsubstituted heteroaryl or heterocyclic ring (preferably 5-6 membered). When R is a C$_{1-6}$ aliphatic group or a phenyl ring, it may be substituted with one or more substituents selected from —NH$_2$, —NH(C$_{1-4}$ aliphatic), —N(C$_{1-4}$ aliphatic)$_2$, halogen, (C$_{1-4}$ aliphatic), —OH, —O—(C$_{1-4}$ aliphatic), —NO$_2$, —CN, —CO$_2$H, —CO$_2$(C$_{1-4}$ aliphatic), O(halo C$_{1-4}$ aliphatic) or -halo(C$_{1-4}$ aliphatic); wherein each C$_{1-4}$ aliphatic is unsubstituted.

The term "221-Amine" refers to 2-amino-2-methylpropan-1-ol (2-amino-2-methylpropanol), or a salt or hydrate thereof.

The term "AMPD" refers to 2-amino-2-methyl-1,3-propanediol, or a salt or hydrate thereof.

The term "AMPSO" refers to N-(1,1-Dimethyl-2-hydroxyethyl)-3-amino-2-hydroxypropanesulfonic acid, or a salt or hydrate thereof.

The term "CHES" refers to 2-(N-cyclohexylamino)ethanesulfonic acid (N-cyclohexyl taurine), or a salt or hydrate thereof.

The term "BHT" refers to dibutylhydroxytoluene (2,6-di-t-butyl-p-cresol).

The term "BHA" refers to butylated hydroxyanisole, generally a mixture of 2- and 3-tert-butyl-4-methoxyphenols.

The term "BRIJ™ 78" refers to polyoxyethylene (20) stearyl ether.

The term "BRIJ™ 700" refers to polyoxyethylene (100) stearyl ether.

The term "DEA" refers to diethanolamine; 2,2'-dihydroxydiethylamine or a salt or hydrate thereof.

The term "IGEPAL® CO-990" refers to polyoxyethylene (100) nonylphenyl ether, branched.

The term "IGEPAL® DM-970" refers to polyoxyethylene (150) dinonylphenyl ether.

The term "PEG" refers to polyethylene glycol, or poly(ethylene glycol). The number after "PEG" refers to the average molecular weight, where Mw refers to weight average molecular weight, and Mn refers to number average molecular weight.

The term "PLURONIC® F68" refers to polyoxyethylene-polyoxypropylene block copolymer.

The term "PLURONIC® F108" refers to poly(ethylene glycol)-block-poly(propylene glycol)-block poly(ethylene glycol), avg. Mn~14,600.

The term "PLURONIC® P103" refers to ethylene oxide/propylene oxide block copolymer, of avg. Mw 4950.

The term "PLURONIC® P104" refers to ethylene oxide/propylene oxide block copolymer, of avg. Mw 5900.

The term "STS" refers to Sodium tridecyl sulfate (C$_{13}$H$_{27}$OSO$_3$Na).

The term "TAPS" refers to N-Tris(hydroxymethyl)methyl-3-aminopropanesulfonic acid (3-[[1,3-dihydroxy-2-(hydroxymethyl)propan-2-yl]amino]propane-1-sulfonic acid), or a salt or hydrate thereof.

The term "4-TBA" refers to 4-tolyl boronic acid, or a salt or hydrate thereof.

The term "TRIS" or "Tris" refers to tromethamine (aka Tris(hydroxymethyl) aminomethane; 2-amino-2-(hydroxymethyl)-1,3-propanediol) or a salt or hydrate thereof.

The term "TRITON™ X-405" refers to octylphenol ethoxylate.

The term "TRITON™ X-405, reduced" refers to polyoxyethylene (40) isooctylcyclohexyl ether.

The term TWEEN®20 refers to polyoxyethylene (20) sorbitan monolaurate, also known as polysorbate 20.

Alkaline Phosphatase Chemiluminescent Substrate Formulations

The substrate formulations of the present invention comprise a chemiluminsent compound of the formula I, a cationic aromatic compound (CAC), an ether-based nonionic surfactant or hydrophilic polymer, and a background reducing agent. The substrate formulations optionally contain anionic surfactants, buffers and enhancer compounds.

The substrate formulations of the present invention are capable of rapidly generating luminescence signal when placed in contact with alkaline phosphatase that exhibits faster TAT time than Lumigen LUMI-PHOS 530® as measured using the assay conditions of Performance Test B. The TAT time is measured from the time alkaline phosphatase substrate is activated by (contacted with) alkaline phosphatase to the time to generation of signal plateau using Performance Test B. Typically fast substrate TAT is at least 2 times faster compared to LUMI-PHOS 530®; preferably at least 3 times, 4 times or 5 times faster. Alternatively, this time as described above is less than 2 minutes, preferably less than 1 minute, more preferably less than 30 s, most preferably less than 10 s.

The substrate formulations provided herein have been shown to generate rapid chemiluminescent signal in the presence of alkaline phosphatase and exhibit improved stability compared to prior art commercial alkaline phosphatase substrate formulations. In some embodiments, stable substrate formulations are provided that exhibit time for signal generation of less than one minute for use with alkaline phosphatase assays. In some embodiments, stable substrate formulations are provided that when stored sealed at 4° C. in the dark exhibit <15%, <10%, <5%, or ≤3% change in signal over 12 months for use with alkaline phosphatase assays.

Chemiluminescent Compound

Chemiluminescent compounds useful in the present formulations are capable of generating chemiluminescence when contacted with an alkaline phosphatase. Such compounds can be synthesized as described in U.S. Pat. Nos. 6,045,727, 6,090,571, 6,139,782, 6,218,137, 6,270,695 and 6,296,787, each of which is incorporated by reference herein.

In the present substrate formulations, the chemiluminescent compound or salt thereof has the formula (I):

$$M_nO_3P-O\underset{R_{14}}{\overset{}{\diagdown}}\underset{}{\overset{}{C}}\underset{R_7}{\overset{}{\diagdown}}Z-A \qquad (I)$$

(structure: acridine core with substituents $R_{13}, R_{12}, R_{11}, R_1, R_{10}, R_9, R_8$ and exocyclic =C(O-PO$_3$M$_n$)(Z-A) group with $R_{14}, R_7$)

wherein A is C$_{1-6}$ haloalkyl, naphthyl, phenyl, substituted phenyl, or heteroaryl, wherein substituted phenyl comprises from 1 to 3 halo, C$_{1-6}$ alkyl, C$_{1-6}$ alkoxy, C$_{1-6}$ haloalkyl, C(O)R$_{15}$, CN or NO$_2$ substituents; R$_1$ is selected from the group consisting of C$_{5-14}$aryl, C$_{1-6}$ alkyl, C$_{1-6}$ haloalkyl, and C$_{5-14}$ aralkyl groups; R$_7$-R$_{14}$ are independently H, C$_{1-6}$ alkoxy, halo, or C$_{1-4}$alkyl, or R$_7$-R$_8$ or R$_8$-R$_9$ or R$_9$-R$_{10}$ $R_{11}$-$R_{12}$ or $R_{12}$-$R_{13}$ or $R_{13}$-$R_{14}$, can be joined together as a carbocyclic or heterocyclic ring system comprising at least one 5 or 6-membered ring; $R_{15}$ is $C_{1-6}$ alkyl; each M is independently selected from H, alkali metal, alkaline earth metal, transition metal, ammonium, organic amine, or amino acid; Z is O or S; and n is 0, 1, or 2. In some embodiments, each M is independently selected from H, Li, Na, or K.

In specific embodiments of compound I, $R_1$ is methyl, Z is O or S, A is phenyl, naphthyl, substituted phenyl, substituted naphthyl, wherein the substituents are selected from 1-3 halo, $C_{1-4}$alkyl, $C_{1-4}$alkoxy; $R_7$-$R_{14}$ are independently H, $C_{1-4}$alkoxy, halo, each M is Na and n is 2.

The compound I is used at a concentration effective to generate chemiluminescence signal, preferably between 0.01 and 50 mM, more preferably between 0.05 and 10 mM and most preferably between 0.1 and 5 mM in the substrate formulation.

In specific embodiments, compound I is selected from:

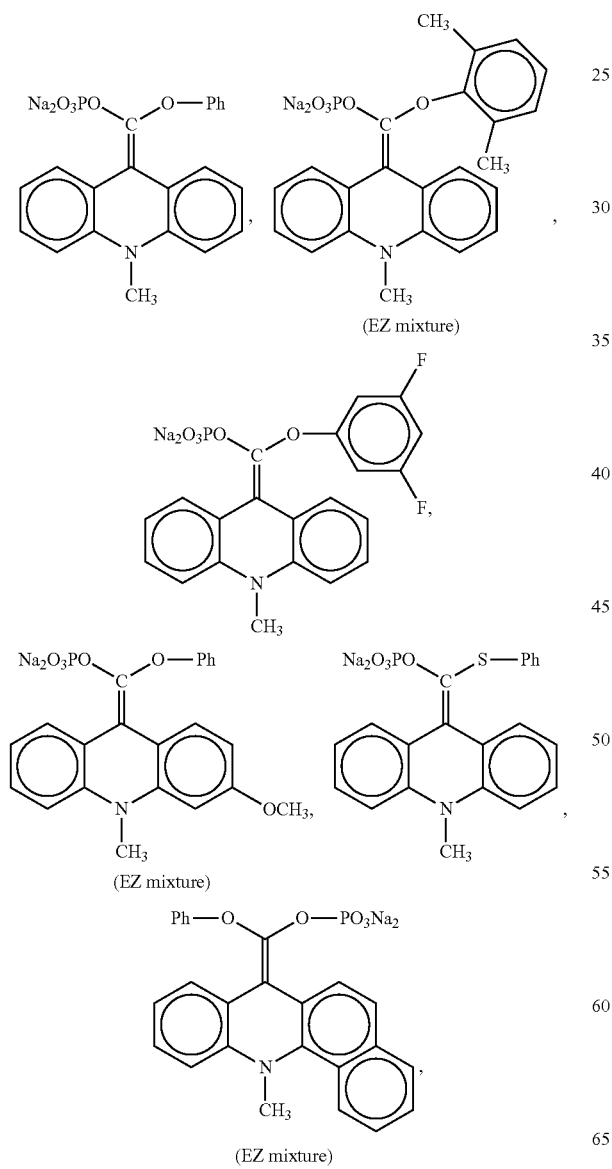

-continued

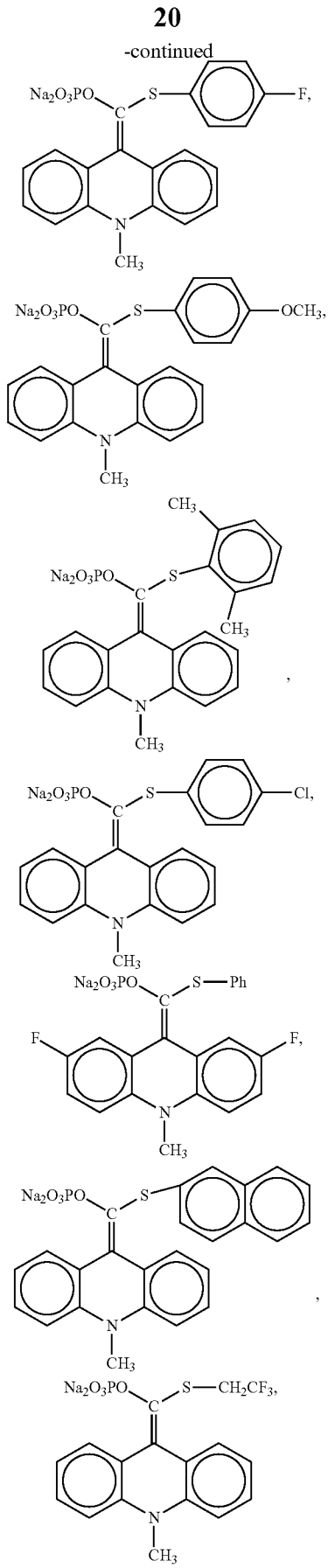

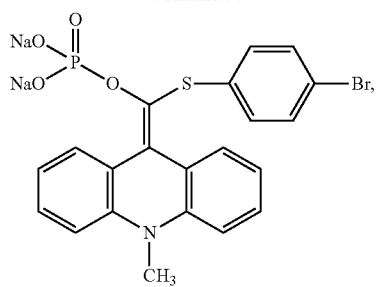

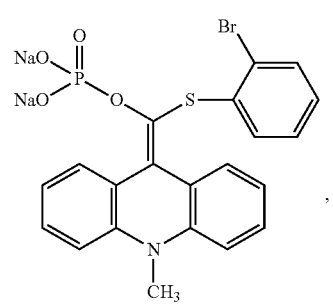

, and

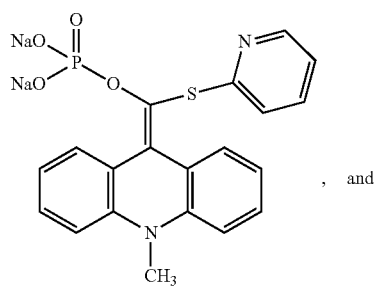

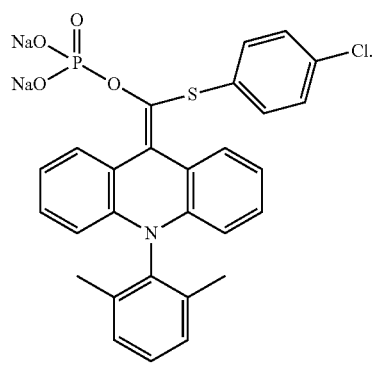

The preparation of compounds of formula I is described in U.S. Pat. No. 6,090,571, examples 1-13, which is incorporated herein by reference.

In a preferred embodiment, compound I is CPA, which forms a fluorescent agent when exposed to alkaline phosphatase as shown below in Scheme 1.

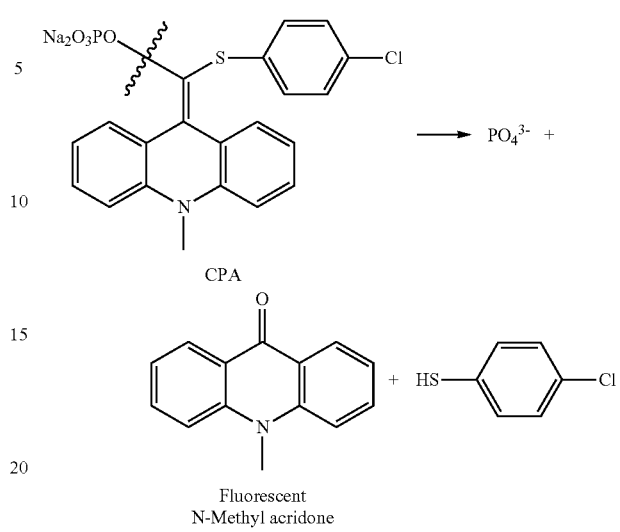

Scheme 1.

Measuring the increase of fluorescence from N-Methyl acridone has been established as a useful tool, in addition to functional RLU testing, for stability study of the substrate formulations of the present invention.

Chemiluminescent compounds of the present invention typically produce light over a 100-200 nm wide band of emission, which exhibits a maximum intensity at wavelengths in the near ultraviolet to the visible region of the electromagnetic spectrum. Typical wavelengths of maximum intensity lambda$_{max}$ are in the range of 350-500 nm. It is contemplated that phosphate compounds of formula I bearing a covalently linked fluorophore not in conjugation with the double bond of the vinyl phosphate moiety could, upon formation of the excited product VI*, undergo intramolecular energy transfer resulting in emission at longer wavelengths from the excited state of the fluorophore.

More than one chemiluminescent compound I can be used concurrently in a method for producing light by the action of a phosphatase enzyme. It may be advantageous in some instances to simultaneously react two or more compounds of formula I with the phosphatase enzyme. When the two or more compounds have differing luminescent or physical properties, the combination of the two may be desirable to produce a light emitting reaction with characteristics not readily achievable through the use of any one compound. Examples of luminescent and physical properties which can differ between compounds I include emission spectrum, duration of light emission, enzyme turnover, rate of rise of emission to maximum, hydrophobicity/hydrophilicity and solubility. While particular luminescent properties can differ among the compounds of formula I in the present methods, the variation in properties does not detract from the basic utility of the compounds; selection of particular compounds with desirable properties can be made by virtue of the teachings and methods described herein.

Cationic Aromatic Compounds

Adding a cationic aromatic compound (CAC) to the above reaction system greatly increases the quantity and/or intensity of light produced. Further, adding the CAC to the compound of formula I in the absence of the phosphatase enzyme does not lead to a corresponding increase in spontaneous (background) chemiluminescence since it is believed that the CAC exerts its effect on a dephosphorylated intermediate derived from compound I and not on compound I itself. Greatly increased sensitivity of detection of the phosphatase enzyme results by virtue of the increased signal/background. It is significant that light emission continues to arise from the excited state of VI and not from the CAC.

A variety of CACs have been found to function to increase the quantity and/or intensity of light produced. CACs are aromatic compounds bearing at least one positive charge either on the aromatic ring or ring system or residing on a substituent on one of the rings, provided that the substituent is in conjugation with the unsaturated ring atoms.

The CACs of the present invention are those compounds having oxidation/reduction potentials suitable for causing an increase in chemiluminescence in reactions of the invention. The suitability of compounds as CACs can be readily determined by means of the methods set forth—in the specific examples below. Without being bound by any particular mechanistic interpretation, it appears that an intermediate product of dephosphorylation of I undergoes a redox reaction which can be reversible or irreversible. Molecular oxygen reacts with one or more of the reacting species in the reaction selected from the CAC, a reduced form of the CAC or the dephosphorylated intermediate of compound I or an oxidized or reduced form thereof to ultimately form an oxygenated reaction product derived from compound I. The oxygenated reaction product undergoes a chemiluminescent reaction, which is likely an O—O bond breaking reaction.

The CACs of the present invention can be a heteroaromatic ring compound comprising one or more isolated or fused aromatic rings containing at least one atom other than carbon (heteroatom), preferably one or more nitrogen atoms in which the positive charge is substantially localized on one or more of the heteroatoms. Examples of this class of CAC are cyanine dyes, thiacyanine dyes, carbocyanine dyes, thiacarbocyanine dyes, selenacarbocyanine dyes, azo dyes and acridinium derivatives of the formula II:

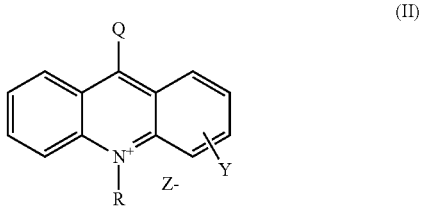

(II)

wherein Q is an electron withdrawing group, Z– is a non-interfering anionic counter ion and R is an alkyl or aralkyl group each of which can optionally contain non-interfering substituents, and Y is an optional substituent. Acridinium derivatives in which some of the ring hydrogens are replaced by other substituting groups are also within the scope of functional CACs. The electron withdrawing group Q can be selected from a halogen, cyano, carbonyl group such as an ester group —COOR', a thioester group —COSR', an amide group —CONR$^1$ R$^2$, a sulfonimide group —CON(R)SO$_2$R', or aryl, N—C$_{1-4}$ alkyl acridinyl, or substituted N—C$_{1-4}$ alkyl acridinyl substituent. Y is selected from H, halo, C$_{1-4}$ alkyl. In some embodiments the aryl substituent is selected from phenyl, naphthyl, or anthryl. Similarly the CAC can be a derivative of a phenanthridinium or phenanthrolinium compound, where R', R" are independently selected from C$_{1-6}$ alkyl, aryl, alkyl substituted aryl. R$^1$, R$^2$ are independently selected from H, C$_{1-6}$ alkyl, aryl, and alkylaryl. In some aspects, Z– is a halide or nitrate.

In some embodiments, the CAC is a compound of formula II, wherein Q is N—C$_{1-4}$ alkyl acridinium, halo substituted N—C$_{1-4}$ alkyl acridinyl, naphthyl, anthryl; R is C$_{1-4}$ alkyl; Z$^-$ is selected from the group consisting of F$^-$, Cl$^-$, Br$^-$, I$^-$, NO$_3^-$, and Y is H or halo.

In some embodiments, the CAC is a compound of formula II, wherein Q is N-methyl acridinyl, naphthyl, or anthryl; R is C$_{1-4}$ alkyl; and Y is H or Cl, Z– is selected from the group consisting of Cl$^-$, Br$^-$, I$^-$, NO$_3^-$.

In some embodiments, the CAC is a compound of formula II, wherein Q is N-methyl acridinyl; R is methyl, ethyl, n-propyl, i-propyl, n-butyl, sec-butyl, iso-butyl or t-butyl; and Y is H or Cl, Z– is selected from the group consisting of Cl$^-$, Br$^-$, I$^-$, NO$_3^-$.

In some embodiments, the CAC is a compound of formula II, wherein Q is N-methyl acridinyl; R is methyl; and Y is H; and Z– is NO$_3^-$.

In some embodiments, the CAC of the present invention can be an aromatic ring compound comprising one or more isolated or fused carbocyclic aromatic rings bearing at least one cationic substituent containing at least one heteroatom, provided that the cationic site is in conjugation with the aromatic ring. In the latter class of CAC it is preferred that the heteroatom be a nitrogen or sulfur atom. Examples include Methylene Blue (3,7-Bis(dimethylamino)phenothiazin-5-ium chloride) and Nile Blue (5-Amino-9-(diethylamino)benzo(a)phenoxazin-7-ium chloride).

In some embodiments, the CACs of the present invention can bear more than one positive charge; e.g. dicationic compounds are within the scope of the invention.

Exemplary compounds of this type include N,N'-dimethylbiacridinium dinitrate, commonly known as lucigenin (10,10'-dimethyl-9,9'-biacridinium nitrate) and 1,1'-dimethyl-4,4'-bipyridinium dichloride, commonly known as methyl viologen dichloride, or paraquat dichloride.

Additional compounds which are useful as the CAC component of the present invention include, by way of illustration, Alcian Yellow, Basic Blue 41, Basic Blue 66, Basic Red 29, 3-Benzyl-5-(2-hydroxyethyl)-4-methylthiazolium chloride, [2-[2-[2-Chloro-3-[(1,3-dihydro-1,3,3-trimethyl-2H-indol-2-ylidene)ethylidene]-1-cyclohexen-1-yl]ethenyl]1,3,3-trimethylindolium perchlorate, {IR-786 perchlorate}, trans-4-[4-(Dibutylamino)styryl]-1-methylpyridinium iodide, 5,5'-Dichloro-11-diphenylamino-3,3'-diethyl-10,12-ethylene thiatricarbocyanine perchlorate, {IR-140}, 3,3'-Diethyl-9-methylthiacarbocyanine iodide, 1,1'-Diethyl-2,2'quinotricarbocyanine iodide, 3,3'-Diethylselenacarbocyanine iodide, 3,3'-Diethylthiacyanine iodide, 3,3'-Diethylthiadicarbocyanine iodide, 2-[4-(Dimethylamino)styryl]-3-ethylbenzothiazolium iodide, 3,6-Dimethyl-2-(4-dimethylaminophenyl)-benzothiazolium bromide, 3,4-Dimethyl-5-(2-hydroxyethyl)thiazolium iodide, 4-[2-[3-[(2,6-Diphenyl-4H-thiopyran-4-ylidene)ethylidene]-2-phenyl-1-cyclo-hexen-1-yl]ethenyl]-2,6-diphenylthiopyrylium tetrafluoroborate {IR-1040}, 5-[3-Ethoxy-4-(3-ethyl-5-methyl-2(3H)-benzothiazolyl-idene)-2-butenylidene]-3-ethyl-2-[(3-ethyl-4,5-diphenyl-2(3H)-thiazolylidene)methyl]-4,5-dihydro-4-oxothiazolium iodide, 3-Ethyl-2-(2-hydroxy-1-propenyl)benzothiazolium chloride, 3-Ethyl-2-methylbenzothiazolium iodide, 3-Ethyl-2-methylbenzoxazolium iodide, 1-Ethyl-3-methyl-1H-imidazolium chloride, Methylene Blue, Nile Blue A, and Triphosphopyridine nucleotide, sodium salt hydrate.

CACs can be used in the substrate formulations at concentrations between 0.01 and 200 μM, preferably between 0.05 and 50 μM, more preferably between 0.1 and 25 μM.

In a preferred embodiment, the CAC is an acridinium compound bearing either one cationic charge or two cationic charges. In one embodiment, the CAC is selected from:

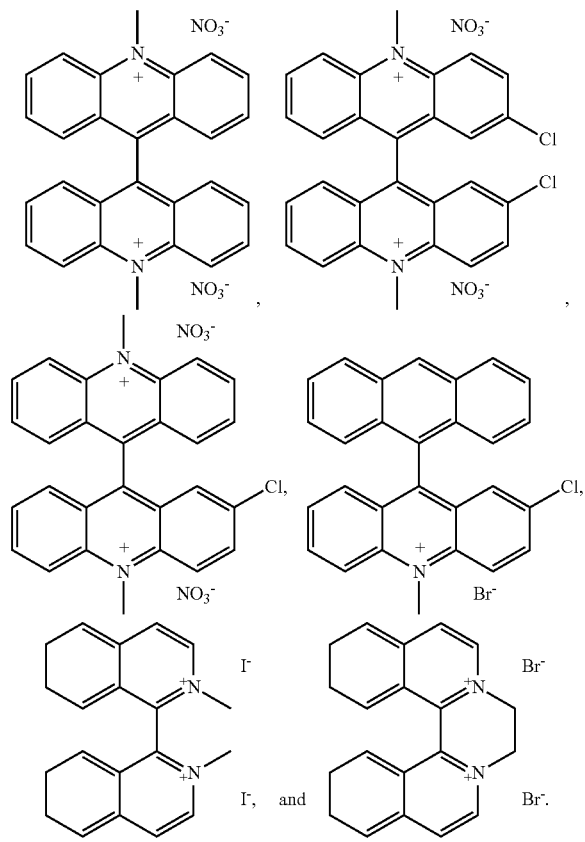

In one aspect, the CAC is N,N'-dimethyl-9,9'-biacridinium dinitrate), commonly known as lucigenin.

Background Reducing Agents

One of the challenges for substrate formulations is to have low background chemiluminescence. The background chemiluminescence in the prior art APS-5 based formulations is generally thought to be caused by the presence of oxidative species in the solution which can lead to elevated background over time.

Background reducing agents (BRAs) are compounds which reduce chemiluminescence produced by the composition in the absence of a phosphatase enzyme. These agents can also function by preventing the accumulation of background chemiluminescence over a period of time. These agents can also function by improving the ratio of specific signal produced by reaction of the composition with a phosphatase enzyme to background chemiluminescence.

In some embodiments, the background reducing agent is a sulfite salt (such as sodium, potassium or lithium salts of sulfites, bisulfites and metabisulfites), organic antioxidants dibutylhydroxytoluene (BHT; 2,6-bis(1,10dimethylethyl)-4-methylphenol), butylated hydroxyl anisole (BHA), 3-t-butyl-4-hydroxyanisole, or 3-tert-butyl-4-hydroxyanisole. In some specific embodiments, the background reducing agents include salts of sulfites, bisulfites and metabisulfites, including sodium sulfite, sodium bisulfite, sodium metabisulfite. In some aspects, the background reducing agent is dibutylhydroxytoluene (BHT; 2,6-bis(1,10dimethylethyl)-4-methylphenol), butylated hydroxyl anisole (BHA), 3-t-butyl-4-hydroxyanisole, or 3-tert-butyl-4-hydroxyanisole.

In some embodiments, the background reducing agent can be an aromatic boronic acid of formula $Ar—B(OH)_2$, wherein Ar is phenyl, substituted phenyl, a fused aromatic ring system that may or may or include heteroatom(s), a substituted fused aromatic ring system that may or may include heteroatom(s), wherein the substituted aryl group may have from 1-3 substituents independently selected from $C_{1-6}$ alkyl, halo, alkoxycarbonyl, or hydroxyl groups. Examples of aromatic boronic acids include phenyl boronic acid, 4-tolyl boronic acid, 4-chloroboronic acid, 4-iodoboronic acid and 3-methoxycarbonylphenyl boronic acid.

In some aspects, the background reducing agent is phenyl boronic acid (PBA), 4-tolyl boronic acid (4-TBA), 4-chlorophenyl boronic acid (4-CPBA), 4-iodophenyl boronic acid (4-IPBA), or 3-methoxycarbonylphenyl boronic acid (3-MCPBA).

In some embodiments, one or more background reducing agents is present in the formulation of compound I.

Background reducing agents can be used at concentrations from 1 uM to 10 mM, preferably from 10-1000 uM. In some embodiments, the background reducing agent is present in the formulation at a concentration selected from within 0.1 mg/mL to 25 mg/mL, 1 mg/mL to 20 mg/mL, or 5 to 15 mg/L.

In addition to the use in substrate formulations of the present invention, it was also found that aryl boronic acids in place of, or in addition to, sodium sulfite significantly reduce the background chemiluminescence of APS-5 based formulations (such as those described in U.S. Pat. Nos. 6,045,727, 6,090,571, 6,139,782, 6,218,137, 6,270,695 and 6,296,787). In some embodiments, the BRA is selected from phenyl boronic acid, 4-tolyl boronic acid, 4-chloroboronic acid, 4-iodoboronic acid and 3-methoxycarbonylphenyl boronic acid. To different extents signal chemiluminescence was also noticed to be lower but at less significant levels. This is especially true at low concentrations of boronic acid. One possible advantage of using boronic acid lies in the fact that it functions only as a reducing agent, with no potential risk of being an oxidizing agent. It was also noticed that addition of organic boronic acid led to significantly improved stability of the formulation, as shown in the examples. When used in combination with sulfite, bisulfite and metabisulfite salts, the aromatic boronic acids provide additional benefits include improved S/N ratios and stability.

Nonionic Surfactants

In some embodiments, improved, substrate formulations are provided comprising an compound I, a cationic aromatic compound, and an ether-linked nonionic surfactant, or hydrophilic polymer.

Substrate formulations comprising non-ionic surfactant provide increased light emission which rapidly reaches and maintains peak light intensity.

In one embodiment, substrate formulations comprising an ether-linked non-ionic surfactant led to significantly improved stability of the substrate formulations. In some aspects, the substrate formulations provided herein do not contain an ester-linked non-ionic surfactant. In one aspect, the substrate formulations provided herein do not contain TWEEN®20.

In another embodiment, the substrate formulation comprise a hydrophilic polymer, for example, a poly(ethylene glycol) (PEG), exhibited improved stability and other performance benefits compared to commercial standard substrate compositions.

In some embodiments, a substrate formulation comprises an ether-linked non-ionic surfactant or a hydrophilic polymer in place of TWEEN® 20.

In some embodiments, a substrate formulation comprises an ether-linked nonionic surfactant. In some embodiments, the ether-linked non-ionic surfactant is selected from Igepal, TRITON, or BRIJ surfactants. In some embodiments, a substrate formulation comprises one or more ether-linked non-ionic surfactants selected from Igepal CO-990, Igepal DM-970, TRITON X-405, TRITON X-405 reduced, BRIJ 78, and BRIJ 700. In some embodiments, a substrate formulation formulation is provided an ether-linked nonionic surfactant selected from Igepal CO-990, Igepal DM-970, TRITON X-405, TRITON X-405 reduced, BRIJ 78, and BRIJ 700. In some embodiments, a substrate formulation comprises one or more of an IGEPAL, TRITON and BRIJ-type ether-linked nonionic surfactants, wherein the formulation does not contain an ester-linked non-ionic surfactant.

In some embodiments, a substrate formulation comprises an a hydrophilic polymer selected from a poly(ethylene glycol), poly(propylene glycol), a combination thereof, or a derivative thereof, that does not have a hydrophobic moiety typical of a traditional surfactant structure. In some embodiments, a substrate formulation comprises a hydrophilic polymer that is a poly(ethylene glycol) having having an average Mw selected in the range of 1,000 to 511,000. Substrate formulations containing poly(ethylene glycol) (Mw=14,000) at 2.5 g/L showed a signal of 94% relative to the reference, and very little signal change after 13 months at 4° C. Similar compositions containing poly(ethylene glycol) with a molecular weight of 35,000 and 100,000 at 1.0 g/L showed similar behaviors.

In some embodiments, a substrate formulation comprises a hydrophilic polymer according to formula (IV)

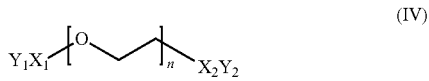

(IV)

wherein $X_1$ and $X_2$ are independently selected from O, S, N or NH, or is absent, wherein $Y_1$ and $Y_2$ is either H, $H_2$ or a small alkyl group(s) with a total number of carbon<4, wherein n is a number from 20 to 12,000, or from 120 to 5,000, or from 250 to 2,500, or n is a number>20. In some embodiments, the hydrophilic polymer is a poly(ethylene glycol) of an average molecular weight Mw selected from within the range of 1,000 to 511,000; 6,000 to 218,000, or 12,000 to 108,000.

In some embodiments, a substrate formulation comprises a hydrophilic polymer selected from the group consisting of poly(ethylene glycol) (Mw=14,000), poly(ethylene glycol) (Mw=35,000), and poly(ethylene glycol) (Mw=100,000).

In some embodiments, a substrate formulation comprises a hydrophilic polymer, wherein the formulation does not contain an ester-linked non-ionic surfactant. In some embodiments, a substrate formulation comprises a hydrophilic polymer, wherein the formulation does not contain TWEEN® 20.

Compositions containing the preferred nonionic surfactants and poly(ethylene glycol) hydrophilic polymers produce intense chemiluminescence signal and also exhibit desired stability over time during storage.

In some embodiments, substrate formulations are provided that do not contain a poloxomer and/or polysorbate surfactant. In some embodiments, substrate formulations are provided that contain a poloxomer and/or polysorbate surfactant. In a particular aspect, a substrate formulation is provided that does not contain a polysorbate.

In some embodiments, nonionic surfactant and hydrophilic polymer concentrations are used in the present compositions at a concentration of from 0.05 to 20 g/L, preferably from 0.1 to 10 g/L and more preferably from 0.2 to 5 g/L.

Anionic Surfactants

The substrate formulations of the present invention can optionally contain an anionic surfactant. Anionic surfactants serve to substantially increase the speed with which maximum chemiluminescence intensity is reached. Anionic surfactants useful in the present formulations include alkyl sulfates and alkylsulfonates having an alkyl group of at least ten carbons.

In some embodiments, the anionic surfactant is selected from alkylsulfates containing at least 10 carbon atoms and alkylsulfonates containing at least 10 carbon atoms. In some embodiments, the anionic surfactant is selected from alkylsulfates containing from 10-22 carbon atoms and alkylsulfonates containing from 10-22 carbon atoms. In some embodiments, the anionic surfactant is selected from a $C_{12}$-$C_{14}$ alkylsulfate. In specific embodiments, one or more of sodium tetradecyl sulfate, sodium dodecyl sulfate (SDS), and sodium tridecyl sulfate (STS) are used as the anionic surfactant. SDS and STS are two preferred compounds for this purpose. In a preferred aspect, the anionic surfactant is STS.

Anionic surfactants are preferably used in substrate formulations in an amount from 0.01 to 10 g/L, preferably from 0.1 to 5 g/L, more preferably 0.3 to 3 g/L.

Buffers

The substrate formulations of the present invention are typically aqueous. An alkaline phosphatase enzyme normally requires non-phosphate basic buffers. The preferred buffers in present invention are amine-based buffers that have pH values from pH 7-12, 8-11, or 9-10. In one aspect, the buffer is an amine buffer at pH greater than 8.0. In some embodiments, substrate formulations comprising 2-Amino-2-methyl-1,3-propanediol (AMPD) amine buffer offered considerable improvement in stability in substrate formulations compared to commercial standards.

The performance of the substrate formulations of the present invention can be affected by the buffer system. Changing pH and molarity have been found to have a direct impact on signal, background and stability. Optimal pH and molarity are different from buffer system to buffer system, even with buffers that are chemically similar.

Buffers that are compatible (performance) over a wide range allows for the greatest opportunity for optimization, particularly with respect to stability.

Optimized TRIS and AMPD systems were found to yield improved results compared to the current commercial standard in many assays, providing improved stability of the substrate formulation at both 2-8° C. and 30° C.

In one embodiment, an substrate formulation comprises an amine buffer selected from TRIS, AMPD, DEA, AMPSO, 221-Amine, CHES, Glycine or TAPS, or a combination of two or more amine buffers thereof.

In another embodiment, a substrate formulation comprises an amine buffer selected from AMPD, DEA, AMPSO, 221-Amine, CHES or TAPS, or a combination of two or more amine buffers thereof.

In one aspect, a substrate formulation comprises an amine buffer, wherein the formulation does not contain TRIS.

In embodiments containing an amine buffer, the molarity of the amine buffer is between 0.025M and 0.65M, between 0.05M and 0.5M, or between 0.1 and 0.3 M. In one aspect, the molarity of the amine buffer is selected from 0.1M and 0.2M.

Enhancer Compounds

Optionally, at least one enhancer compound can also be employed in the substrate formulations of the present invention, in order to increase the amount of light emitted. Enhancers which are effective in the present method can function by increasing the fraction of excited state product molecules which emit light, by increasing the fraction of product molecules which are formed in the excited state, by increasing the rate of reaction or turnover of the enzyme, by increasing the rate of a subsequent chemical reaction step, by improving the stability of the enzyme, by promoting the association of the enzyme with the compound I, by inhibiting or preventing competitive non-luminescent side reactions or by any combination of these mechanisms. Enhancers will be used in an amount effective to enhance the chemiluminescence, preferably between 0.001 and 5 mg/mL in the final reaction solution, more preferably between 0.01 and 2.5 mg/mL.

Enhancer compounds that are effective in the practice of the present method are typically surfactant compounds, i.e. compounds which display surface active properties, e.g., surface tension depression, surface wetting or detergency. Surfactants comprise a hydrophilic region containing polar and/or ionic groups and a hydrophobic region containing mainly hydrocarbon groups or alkylenoxy groups or both. Surfactants are categorized as cationic, anionic, nonionic and zwitterionic and can be monomeric or polymeric. Cationic surfactant enhancers found useful in the practice of the present invention include polyvinyl type polymers with pendant quaternary phosphonium groups which are disclosed in U.S. Pat. No. 5,393,469, the disclosure of which is incorporated herein by reference. Exemplary polymers of this type include polyvinylbenzyltributylphosphonium chloride copolymer with polyvinylbenzyltrioctylphosphonium chloride and (polyvinylbenzyltributylphosphonium chloride). Polyvinyl type polymers with pendant quaternary ammonium groups are also useful as enhancers in the present invention. Examples of such polymers are disclosed in U.S. Pat. No. 5,112,960, the disclosure of which is incorporated herein by reference and include polyvinylbenzylbenzyldimethylammonium chloride and polyvinylbenzyl tributylammonium chloride.

Salts

In one embodiment, substrate formulations for chemiluminescent reaction with alkaline phosphatase can further comprise a magnesium or zinc salt. In some aspects, the salt is present in the formulation at a concentration of 0.01-50 mM, 0.01-10 mM, or 0.1-1.0 mM, for increasing the activity of the enzyme. In some aspects, the magnesium salt is $MgCl_2$ or magnesium acetate. In some aspects, the zinc salt is $ZnCl_2$. In some aspects, NaCl, KCl, sodium acetate, or potassium acetate is present in the formulation. In some aspects, a substrate formulation comprises 10 uM, 0.1 mM, 0.5 mM, 0.88 mM, or 1 mM $MgCl_2$. In some embodiments, a substrate formulation comprises 0.01-10 mM, 0.05-0.5 mM, or 0.1 mM $ZnCl_2$.

Preferred Substrate Formulations

In one aspect, a substrate formulation is provided for use in alkaline phosphatase assays, wherein the formulation comprises an compound I, a cationic aromatic compound, a background reducing agent, an ether-linked non-ionic surfactant or hydrophilic polymer, an anionic surfactant, and an amine buffer at pH 7-12, 8-11, or 8.5-10.

In one aspect, the Imax of the substrate formulation occurs in <5 minutes, <4 minutes, <2 minutes, <1 minute, <45 seconds, <30 seconds, <20 seconds, <10 seconds, <5 seconds, <4 seconds, <3 seconds, or <2 seconds following exposure to a phosphatase enzyme. In another aspect, the substrate formulation is stable under storage conditions at 4° C. and exhibits <10% loss of original RLU after storage at 4° C. for 300 days.

In some aspects, the substrate formulation of the disclosure exhibits >90%, or >95% retained activity, compared to original RLU, when stored at 4° C. for 300 days.

In some aspects, the substrate formulation of the disclosure exhibits >90% retained activity when stored at 4° C. for 400 days or more.

In another aspect, the substrate formulation of the disclosure exhibits a chemiluminescent signal change in intensity (%) per day after 15 days when stored at 30° C. of <−0.60%/day, <−0.50%/day, <−0.40%/day or <−0.30%/day after exposure to an alkaline phosphatase enzyme.

In another aspect, the substrate formulation of the disclosure exhibits a chemiluminescent signal change in intensity (%) per month after 12 months when stored at 4° C. of ≤−1.0% per month; ≤−0.9%/month; or ≤−0.80%/month after exposure to an alkaline phosphatase enzyme.

In one aspect, a substrate formulation comprises 0.01 mM-50 mM compound I, 0.01-200 uM cationic aromatic compound, 1 uM-10 mM background reducing agent, 0.05-20 g/L ether-linked non-ionic surfactant or hydrophilic polymer, 0.01-10 g/L anionic surfactant, and an amine buffer at from 0.025M to 0.65M and at pH 7-12.

In one aspect, a substrate formulation comprises 0.05 mM-10 mM compound I, 0.05-50 μM cationic aromatic compound, 10 uM-1000 uM background reducing agent, 0.1 to 10 g/L ether-linked non-ionic surfactant or hydrophilic polymer, 0.1 to 5 g/L anionic surfactant, and an amine buffer at from 0.05M to 0.5M and at pH 8-11.

In one aspect, a substrate formulation comprises 0.1 mM-5 mM compound I, 0.1-25 μM cationic aromatic compound, 50 to 500 uM background reducing agent, 0.2 to 5 g/L ether-linked non-ionic surfactant or hydrophilic polymer, 0.1 to 5 g/L anionic surfactant, and an amine buffer at from 0.1M-0.4M and at pH 8-11.

In some specific embodiments, the substrate formulation comprises CPA (as compound I), lucigenin (as CAC), sodium sulfite (background reducing agent), an ether-linked nonionic surfactant selected from the group consisting of IGEPAL (CO-990, DM-970), TRITON (X-405, X-405 reduced), and BRIJ (78, 700), a hydrophilic polymer selected from the group consisting of poly(ethylene glycol) (Mw=14,000), poly(ethylene glycol) (Mw=35,000), and poly(ethylene glycol) (Mw=100,000), an anionic surfactant which is SDS or STS, and an amine buffer which is TRIS or AMPD at a concentration from 0.025M to 0.65M at a pH between 8 and 11.

In one aspect, a substrate formulation comprises 0.30 g/L CPA, 3.26 mg/L Lucigenin, 10 mg/L sodium sulfite, 1.0 g/L PEG (Mw 35K), 1.0 g/L SDS, and 0.3 M TRIS buffer at pH 9.2.

In another aspect, a substrate formulation comprises 0.30 g/L CPA, 3.26 mg/L Lucigenin, 5 mg/L sodium sulfite, 2.0 g/L TRITON-X-405, 1.0 g/L SDS, and 0.1 M AMPD buffer pH 9.7.

In another aspect, a substrate formulation comprises 0.30 g/L CPA, 3.26 mg/L Lucigenin, 10 mg/L sodium sulfite, 1.5 g/L BRIJ 78, 1.0 g/L SDS, and 0.3 M TRIS buffer pH 9.35.

In another aspect, a substrate formulation comprises 0.15 g/L CPA, 3.26 mg/L Lucigenin, 10 mg/L sodium sulfite, 2.0 g/L IGEPAL DM-970, 1.0 g/L SDS, and 0.3 M TRIS buffer pH 9.35.

In one aspect, a substrate formulation comprises 0.15 g/L CPA, 3.26 mg/L Lucigenin, 10 mg/L sodium sulfite, 1 g/L PEG (35K), 0.9 g/L SDS, and 0.1 M AMPD buffer pH 9.7.

In another aspect, a substrate formulation comprises 0.15 g/L CPA, 3.26 mg/L Lucigenin, 10 mg/L sodium sulfite, 1 g/L PEG (Mw 35K), 0.5 g/L STS, and 0.1 M AMPD, pH 9.7 buffer.

In another aspect, a substrate formulation comprises CPA (0.15 g/L), $Na_2SO_3$ (10 mg/L), lucigenin (3.26 mg/L), PEG 100K (1.0 g/L) and SDS (0.9 g/L) in TRIS buffer pH 9.2.

In another aspect, a substrate formulation comprises 0.30 g/L CPA, 2.45 mg/L Lucigenin, 10 mg/L sodium sulfite, 0.05 mM 4-tolylboronic acid, 1 g/L PEG (35K), 0.9 g/L SDS, and 0.1 M AMPD buffer at pH 9.7.

In another aspect, a substrate formulation comprises 0.15 g/L CPA (((4-chlorophenyl)thio)(10-methylacridin-9(10H)-ylidene)methyl phosphate, disodium salt), 3.26 mg/L Lucigenin, 10 mg/L sodium sulfite, 1 g/L PEG (35K), 0.9 g/L SDS, and 0.1 M AMPD buffer at pH 9.7.

Method of Using Substrate Formulations

Another aspect of the present invention, therefore, is the use of compounds of any of formula I and a CAC in a method to produce detectable chemiluminescence by reaction with a phosphatase enzyme. Reaction of a compound of formula I with a phosphatase enzyme in the presence of a CAC in an aqueous buffer solution produces easily detected chemiluminescence from the excited state of VI. Light intensity reaches a maximum level within seconds to minutes at room temperature when the reaction is conducted at alkaline pH.

In some embodiments, substrate formulations are provided for use in alkaline phosphatase assays, appropriate for use with native or recombinant alkaline phosphatases. The phosphatase enzyme which can undergo the chemiluminescent reaction may include alkaline phosphatase isolated from a bacterial source such as *E. coli*, or a mammalian alkaline phosphatase or acid phosphatase from plant or mammalian sources. In one aspect, the alkaline phosphatase may be a native alkaline phosphatase, for example, native calf intestine alkaline phosphatase. In another aspect, the phosphatase enzyme may be a recombinant phosphatase enzyme, e.g., recombinant alkaline phosphatase. In some embodiments, the alkaline phosphatase is purchased from a commercial vendor such as Roche Diagnostics Corp. Indianapolis, Ind., or Sigma-Aldrich Corporation, St. Louis, Mo. The alkaline phosphatase may be recombinant alkaline phosphatase expressed in *Pichia pastoris*, e.g., recombinant bovine alkaline phosphatase expressed in *Pichia pastoris*, e.g., available from Roche, or Sigma-Aldrich. The alkaline phosphatase may be recombinant shrimp alkaline phosphatase, for example produced in *Pichia pastoris*, available from, e.g., ArcticZymes, Tromso, Norway.

Conjugates of a phosphatase enzyme and a biological molecule can also be used in the method for producing chemiluminescence, the only provision being that the conjugate display phosphatase activity, i.e., the ability to hydrolyze phosphate monoesters. Biological molecules which can be conjugated to one or more molecules of a phosphatase enzyme include DNA, RNA, oligonucleotides, antibodies, antibody fragments, antibody-DNA chimeras, antigens, haptens, proteins, lectins, avidin, streptavidin and biotin. Complexes including or incorporating phosphatase enzymes such as liposomes, micelles, vesicles and polymers which are functionalized for attachment to biological molecules can also be used in the methods of the present invention.

The reaction of a composition of the present invention with a phosphatase enzyme to produce chemiluminescence constitutes a rapid and highly sensitive method for detecting the presence or amount of the phosphatase enzyme. Use of the present method can therefore be made for the purpose of determining the presence or quantity of a phosphatase enzyme in a sample by measuring the amount or intensity of light produced by reaction of the sample with a compound of formula I.

Techniques for performing enzyme assays are well known. With the guidance provided by the examples as taught herein, variations of procedures for preparing samples, determining appropriate quantities and ratios of reagents, reaction times, constructing calibration curves and the like will be within the ability of one of ordinary skill in the art to devise as a matter of routine experimentation.

The methods and compositions of the invention can be used in conjunction with any suitable assay known in the art, for example any suitable affinity assay or immunoassay known in the art where alkaline phosphatase and substrate formulations therefore can be advantageously used, including, but not limited to, protein-protein affinity assays, protein-ligand affinity assays, nucleic acid affinity assays, indirect fluorescent antibody assays (IFAs), enzyme-linked immunosorbant assays (ELISAs), radioimmunoassays (RIAs), and enzyme immunoassays (EIAs), chemilluminescent enzyme immunoassays based on magnetic microparticles, direct or indirect assays, competitive assays, sandwich assays, etc. Suitable assay formats include, but are not limited to, assays and formats employed in the Examples herein.

The substrate formulations of the present invention are amenable for use with automated Immunoassay Systems, including Access 2 Immunoassay System; UniCel DxI 600 Access Immunoassay System; UniCel DxI 800 Access Immunoassay System; UniCel DxC 600i Synchron Access Clinical System; UniCel DxC 660i Synchron Access Clinical System; UniCel DxC 680i Synchron Access Clinical System; UniCel® DxC 860i Synchron® Access® Clinical Systems; UniCel® DxC 880i Synchron® Access® Clinical Systems (all available from Beckman Coulter, Brea, Calif.); Cobas Systems (available from Roche Diagnostics, Switzerland); Architect Systems (available from Abbott, Ill.); and Centaur Systems (available from Siemens, Germany).

In a preferred method of producing light from the reaction of compound I with a phosphatase enzyme, the reaction is performed at a temperature between 5° C. and 50° C., preferably between 20° C. and 40° C. in an aqueous buffer solution at a pH between 7 and 12, 8 and 11, or preferably between 8.5 and 10. The enzyme is preferably an alkaline phosphatase or an alkaline phosphatase conjugate.

Light emitted by the present method can be detected by any suitable known means such as a luminometer, x-ray film, high speed photographic film, a CCD camera, a scintillation counter, a chemical actinometer or visually. Each detection means has a different spectral sensitivity. The human eye is optimally sensitive to green light, CCD cameras display maximum sensitivity to red light, x-ray films with maximum response to either UV to blue light or green light are available. Choice of the detection device will be governed by the application and considerations of cost, convenience, and whether creation of a permanent record is required.

It is contemplated that fluorescent energy acceptors can be employed to shift the maximum emission to longer wavelengths (red-shifting). Various techniques for red-shifting emission are known in the art of chemiluminescent reactions and assays.

Covalently linked fluorophores as described above are one example. Fluorescers can be added to the reaction solution as separate species. Fluorescers can be linked to an enhancer substance such as a cationic polymer or associated with an enhancer substance such as a micelle or polymer in order to bring the fluorescer in close contact to the compound. Alternately, the fluorescer can be provided in a non-fluorescent form which is convertible to the fluorescent form by removal of a phosphate group during the enzyme reaction period. Examples of the latter type of compound include fluorescein diphosphate, coumarin phosphates such as 4-methylumbelliferone phosphate, benzothiazole phosphates such as ATTOPHOS® (JBL Scientific, San Luis Obispo, Calif.).

EXAMPLES

Stability Test A

An aliquot (100 µL) of AP substrate formulation was added to a micro-titer plate well (8 replicates for each formulation). The plate was placed in a luminescence plate reader (Luminoskan, Labtech) and to each well was injected 20 µL of AP solution (2 ng/mL). Luminescence signal was read after 30 seconds and intergraded for 2 seconds.

Performance Test B

An aliquot (5 µL) of AP enzyme solution (2 ng/mL) was place in a polyethylene tube. The tube was placed in a luminometer (20/20e, Turner Designs) and 100 µL of the substrate was injected to each well. Immediately after the injection, luminescence signal was read for 60 seconds.

APS-5 Formulations

Lumigen APS-5 AP chemiluminescent substrate reagent ("APS-5", Product No. APS-5-101, Lumigen, Southfield, Mich.) comprises CPA as the compound I in 0.3 M TRIS buffer, pH 9.35 containing 0.1% (w/v) TWEEN® 20, lucigenin, SDS, and $Na_2SO_3$.

Example 1. APS-5 Formulation Stability

Various lots of APS-5 were evaluated for performance stability over time using Stability Test A. The relative stability of these representative lots is shown in FIG. 1. A significant reduction in performance was seen after 100 days at 4° C.

To identify the formulation component that was predominantly responsible for the limited stability, additional quantities (50% more) of each component were added to a single lot of APS-5 and these modified formulations were tested using Stability Test A. The results are shown in Table 1.

TABLE 1

| APS-5 Performance with additional components | |
|---|---|
| Material | Performance |
| APS-5 Solid | 94.2% |
| Lucigenin | 91.9% |
| SDS | 70.5% |
| TWEEN® 20 | 131.9% |
| Sodium Sulfite | 100.1% |

Figure 2:
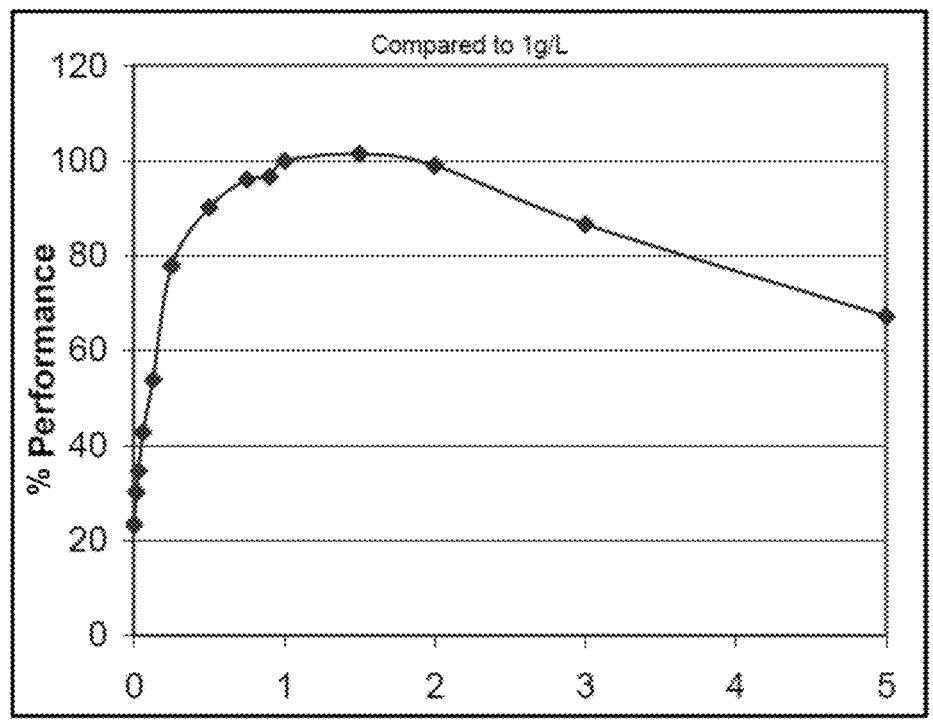
FIG. 2 shows effect on assay performance (% performance) following addition of various amounts of TWEEN® 20 (0 to 5 g/L) to an APS-5 formulation compared to an APS-5 formulation with 1 g/L TWEEN® 20.

TWEEN® 20 exhibited the greatest impact on assay performance. The same experiment was again repeated with various amounts of TWEEN® 20. Assay performance was compared to a standard APS-5 formulation with 1 g/L TWEEN® 20 (0.1% w/v). As shown in FIG. 2, each of 0.5, 0.75, 0.9, 1, 1.5, and 2 g/L TWEEN® 20 exhibited at least 90% performance compared to 1 g/L TWEEN® 20.

To confirm the role of TWEEN® 20 in the performance of APS-5, an additional 0.5 g/L TWEEN® 20 was added to several lots of Lumigen APS-5 that had been stored at 4° C. for various numbers of days and had exhibited various degrees of signal degradation. Following addition of TWEEN® 20, the modified APS-5 was again tested with Stability Test A. Results are shown in Table 2.

TABLE 2

| APS-5 Performance of Retained Lots with Added TWEEN® 20 | | |
|---|---|---|
| Lot | Performance before added TWEEN 20 | Performance with added TWEEN® 20 |
| A | 17.6 | 43.1 |
| B | 25.5 | 49.6 |
| C | 51.6 | 84 |
| D | 48.8 | 67.5 |
| E | 59.5 | 71.7 |
| F | 63.8 | 72.9 |
| G | 88.9 | 95.1 |
| H | 92.1 | 100.5 |

In each case, performance was improved by addition of TWEEN® 20. Although suspected causes of instability included the APS-5 solid and TWEEN® 20; it was determined that the APS-5 solid contributed <5% performance loss/year, while the TWEEN® 20 caused >20% performance loss/year.

The APS-5 formulation was then modified as shown in Table 3 and tested using Stability Test A. Table 3 shows initial % performance of modified APS-5 compared to freshly prepared standard APS-5.

TABLE 3

| APS-5 Modified Formulations to modify or replace TWEEN® 20 | |
|---|---|
| Modification | Initial Performance compared to original APS-5 |
| Increase amount of TWEEN® 20 to 2 g/L | 99.0% |
| Increase amount of TWEEN® 20 to 3 g/L | 86.6% |
| Lower pH to 9.2 | 93.6% |
| Lower pH to 9.1 | 86.4% |
| Lower pH to 9.0 | 78.8% |
| Add 0.1M TRIS | 92.5% |
| Replace TWEEN® 20 with 1 g/L TWEEN® 80 | 111.3% |

TABLE 3-continued

APS-5 Modified Formulations to modify or replace TWEEN ® 20

| Modification | Initial Performance compared to original APS-5 |
|---|---|
| Replace TWEEN ® 20 with 1 g/L TWEEN ® 40 | 109.2% |
| Replace TWEEN ® 20 with 0.5 g/L Pluronic F87 | 86.5% |
| Replace TWEEN ® 20 with 2.5 g/L PEG Mn = 14000 | 94% |
| Replace TWEEN ® 20 with 2.0 g/L TRITON X 100 | 80% |

Other modifications were made and are not shown, including the evaluation of PEGs of various lower Mn. The best performance was exhibited by PEG Mn 14,000. Modified APS-5 formulations with TWEEN® 40, TWEEN® 80, TRITON X, 0.1 M TRIS each exhibited less or equal performance stability than original APS-5 formulation with original concentration of TWEEN® 20. Modified APS-5 formulations with PEG, Pluronic, additional TWEEN® 20, or lower pH exhibited superior performance stability to unmodified APS-5.

Customer samples were tested using modified APS-5 formulations using Performance Test B. APS-5 formulations with TWEEN® 20 2 g/L at three different pH levels (pH 9.0, pH 9.1 and pH 8.9 pH) all exhibited performance speed of <30 sec. time frame. A modified APS-5 formulation with PEG Mn=14,000 at 2.5 g/L at pH 9.2, with no TWEEN® 20, was found to exhibit a desirable signal intensity plateau (TAT) of <10 sec, and good real time stability, exhibiting 99.7% of original performance after 13 months at 4° C. In sum, the stability issue of current APS-5 formulation was found to be mainly caused by degradation of TWEEN® 20 under APS-5 buffer conditions.

Example 2. Alternative Non-Ionic Surfactants

Experiments were performed in order to determine the effect on stability of ether-linked nonionic surfactants. The following surfactants were investigated: Pluronic F68, Pluronic F108, Pluronic P103, and Pluronic P105 and ether-linked non-ionic surfactants, including Igepal CO-990, Igepal DM-970, TRITON X-405, TRITON X-405 reduced, BRIJ 78, and BRIJ 700.

Figure 3:
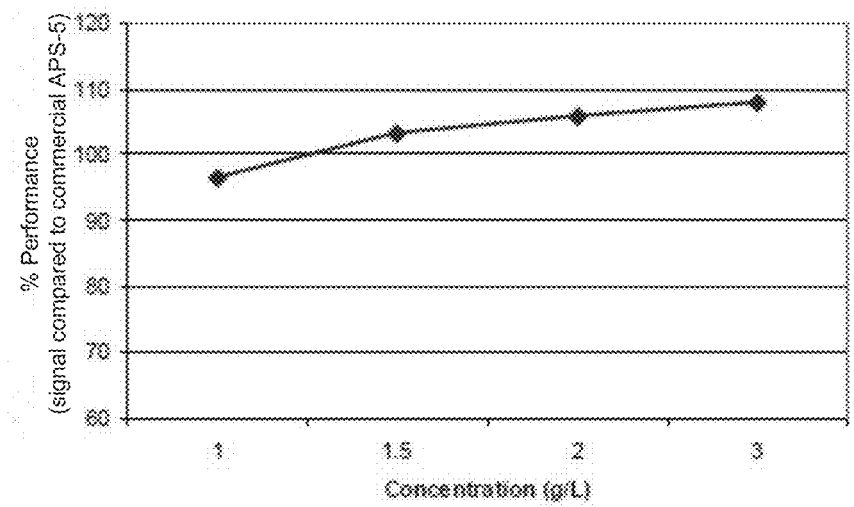
FIG. 3 shows signal as percentage (% performance) of commercial standard APS-5 formulation of modified APS-5 formulations with BRIJ 700 as nonionic surfactant at various concentration levels.

The composition used for the testing consisted of the following: CPA (0.30 g/L), 0.3 M TRIS buffer pH 9.35, lucigenin (3.26 mg/L), Na₂SO₃ (10 mg/L), SDS (1 g/L) and the nonionic surfactant at indicated concentration. The compositions were stored at 4° C. and tested from time to time during storage. Relative signal intensity as percentage of a reference standard composition (commercial APS-5), signal profiles, and background for test compositions was determined. Each alternative nonionic surfactant was tested at 0.25 g/L, 0.5 g/L, 1.0 g/L, 1.5 g/L, 2.0 g/L, and 3.0 g/L non-ionic surfactant in the test compositions. As shown in FIG. 3, representative BRIJ 700 test compositions showed similar signal profiles (i.e., time to maximum signal intensity, Imax; background) as compared to APS-5.

Surprisingly, formulations prepared with IGEPAL (CO-990, DM-970), TRITON (X-405, X-405 reduced), and BRIJ (78, 700) produced similar or higher signal intensity than standard APS-5; however, those prepared with Pluronic (F68, F108, P103 and P105) were observed to give lower signals than standard APS-5, as shown in Table 4.

Stability studies were performed for each formulation employing alternative nonionic surfactants in APS-5 over 106 or 124 days at 4° C. Data is shown as signal percentage of standard APS-5 in Table 4.

TABLE 4

Stability of Modified APS-5 Formulations

| (g/L) | Day 0 (%) | Day 38 (%) | Day 70 (%) | Day 124 (%) |
|---|---|---|---|---|
| A. APS-5 with IGEPAL CO-990 (g/L) | | | | |
| 0.25 | 92.1 | 79.9 | 80.6 | 79 |
| 0.5 | 101.4 | 90.9 | 90.4 | 88.2 |
| 1.0 | 108.1 | 93.3 | 92.7 | 91.9 |
| 1.5 | 107.5 | 94.7 | 94.9 | 94 |
| 2.0 | 107.7 | 94.2 | 94.3 | 91.6 |
| 3.0 | 102.6 | 91.9 | 91.3 | 89.5 |
| B. APS-5 with IGEPAL DM-970 (g/L) | | | | |
| 0.25 | 94.7 | 85.6 | 81.5 | 81.8 |
| 0.5 | 102.6 | 93.6 | 89.8 | 89.6 |
| 1.0 | 112.0 | 94.6 | 91.4 | 94.3 |
| 1.5 | 112.7 | 99.6 | 96.6 | 99.1 |
| 2.0 | 115.6 | 104.4 | 96.9 | 98.6 |
| 3.0 | 114.1 | 103.2 | 97.8 | 99 |
| C. APS-5 with TRITON X-405 (g/L) | | | | |
| 0.25 | 86.9 | 71.2 | 71.7 | 70.4 |
| 0.5 | 101.3 | 89.7 | 88.1 | 84.7 |
| 1.0 | 108.0 | 95.1 | 96.6 | 93.2 |
| 1.5 | 110.8 | 101.5 | 101.9 | 97.7 |
| 2.0 | 112.9 | 100.3 | 100.1 | 98.2 |
| 3.0 | 106.9 | 98.6 | 96.9 | 94.6 |
| D. APS-5 with TRITON X-405-reduced (g/L) | | | | |
| 0.25 | 87.3 | 75.8 | 75.9 | 73.9 |
| 0.5 | 97.6 | 87.4 | 86.3 | 84.8 |
| 1.0 | 105.0 | 95.2 | 91.9 | 90.7 |
| 1.5 | 105.9 | 99.3 | 94.9 | 93.2 |
| 2.0 | 104.7 | 90.8 | 94.4 | 91 |
| 3.0 | 95.3 | 78.1 | 85.4 | 82.1 |

| (g/L) | Day 0 (%) | Day 29 (%) | Day 62 (%) | Day 106 (%) |
|---|---|---|---|---|
| E. APS-5 with BRIJ 78 (g/L) | | | | |
| 1.0 | 108.77 | 108.7 | 124.5 | 116.7 |
| 1.5 | 111.28 | 117 | 125.9 | 118.8 |
| 2.0 | 107.53 | 114.5 | 117.7 | 114 |
| 3.0 | 88.8 | 99.6 | 100.2 | 97.2 |
| F. APS-5 with BRIJ 700 (g/L) | | | | |
| 1.0 | 96.57 | 103.2 | 108 | 101 |
| 1.5 | 103.09 | 109.8 | 113.3 | 106.2 |
| 2.0 | 105.82 | 109.9 | 113.2 | 108.6 |
| 3.0 | 107.81 | 112.8 | 115.3 | 110.9 |
| G. APS-5 with PLURONIC F68 (g/L) | | | | |
| 1.0 | 81.11 | 84 | 86.5 | 84.3 |
| 1.5 | 74.79 | 78.4 | 80.1 | NT |
| 2.0 | 69.1 | 74.5 | 74.1 | NT |
| 3.0 | 58.15 | 62.3 | 62 | NT |
| H. APS-5 with PLURONIC 108 (g/L) | | | | |
| 1.0 | 77.33 | 82.2 | 87.7 | 84.1 |
| 1.5 | 70.48 | 76.7 | 81.1 | NT |
| 2.0 | 67.76 | 72.1 | 72 | NT |
| 3.0 | 54.11 | 58.3 | 57.5 | NT |
| I. APS-5 with PLURONIC P103 (g/L) | | | | |
| 1.0 | 46.32 | 50.4 | 50.9 | 49.3 |
| 1.5 | 29.45 | 32.1 | 32.9 | NT |
| 2.0 | 28.8 | 29.4 | 30.1 | NT |
| 3.0 | 18.2 | 18.5 | 19.1 | NT |
| J. APS-5 with PLURONIC 105 (g/L) | | | | |
| 1.0 | 51.62 | 59.3 | 57.4 | 54.7 |
| 1.5 | 40.93 | 46.5 | 44.8 | NT |
| 2.0 | 31.12 | 33 | 33.8 | NT |
| 3.0 | 17.54 | 18 | 18.4 | NT |

NT = not tested

Each of the modified formulations prepared with ether-linked nonionic surfactants displayed better stability than commercial reference substrate APS-5 containing TWEEN® 20. Even though signal intensity varied, all these formulations showed significantly improved stability after 3 months of storage at 4° C., compared to substrate formulations with TWEEN® 20. The modified formulations comprising alternative nonionic surfactants displayed similar background and signal profiles compared to the current formulation. Of the formulations tested, those with IGEPAL, TRITON and BRIJ-type surfactants gave similar or higher signal intensity compared to TWEEN® 20. Formulations with IGEPAL, TRITON and BRIJ-type surfactants at optimal concentrations as identified during initial experiments were further monitored for signal stability over the time at 4° C. by comparing each with the corresponding freshly prepared formulation. Five out of the six formulations tested showed less than 10% signal loss after 15 months.

Other nonionic surfactants were tested in substrate formulations, but they failed to provide compositions that maintain both signal intensity and storage stability features. These nonionic surfactants include poloxomer type Pluronic surfactants F68, F108, P103, P105, polysorbate type surfactants TWEEN® 20, TWEEN® 40 and TWEEN® 80. APS-5 formulation contains 0.1% w/v TWEEN® 20. Compositions made of TWEEN® 40 or TWEEN® 80 gave similar or worse profile as compared to TWEEN® 20. In some embodiments, substrate formulations are provided that do not contain poloxomer type Pluronic surfactants F68, F108, P103, P105, or polysorbate type surfactants TWEEN® 20, TWEEN® 40 and TWEEN® 80.

Example 3. Further Evaluation of Selected Nonionic Surfactants in APS-5 Formulations The ether-linked nonionic surfactant compositions shown in italics in Table 4 were selected for further study. A comparison of activity to commercial standard APS-5 is shown in Table 5.

TABLE 5

Activity of Freshly Prepared Formulations compared to Commercial standard APS-5

| Surfactant concentration in Test substrate formulation | Activity compared to Standard APS-5 |
| --- | --- |
| IGEPAL CO-900, 1.5 g/L | 97.6% |
| IGEPAL DM-970, 2.0 g/L | 101.3% |
| TRITON X-405, 2.0 g/L | 97.3% |
| TRITON X-405 reduced, 1.5 g/L | 95.9% |
| BRIJ 78, 1.5 g/L | 122.1% |
| BRIJ 700, 3.0 g/L | 115.2% |

The six formulations of Table 5 were stored at 4° C. and subjected to Stability Test A. Results are shown in Table 6A.

TABLE 6A

Extended Stability Studies at 4° C. for substrate formulations comprising Ether-based Nonionic Surfactants

| Surfactant | Retained Activity Compared to Freshly Made (%) | | | |
| --- | --- | --- | --- | --- |
| | Day 70 | Day 197 | Day 317 | Day 471 |
| IGEPAL CO-900, 1.5 g/L | 99.3 | 96.7 | 95.7 | 91.1 |
| IGEPAL DM-970, 2.0 g/L | 99.1 | 97.5 | 97.0 | 92.8 |
| TRITON X-405, 2.0 g/L | 99.6 | 97.4 | 96.0 | 95.0 |
| TRITON X-405 reduced, 1.5 g/L | 98.7 | 97.8 | 97.1 | 92.3 |
| BRIJ 78, 1.5 g/L | 98.5 | 97.7 | 96.7 | 88.0 |
| BRIJ 700, 3.0 g/L | 99.2 | 96.9 | 96.1 | 92.0 |

A similar composition containing poly(ethylene glycol) (Mw=14,000) at 2.5 g/L showed a signal of 94% relative to the reference, and very little signal change after 13 months at 4° C. Similar compositions containing poly(ethylene glycol) with a molecular weight of 35,000 and 100,000 at 1.0 g/L showed similar behaviors.

As shown in Table 6A, test compositions comprising ether-linked non-ionic surfactants exhibited >90%, and >95% retained activity after 300 days when stored at 4° C., or >90% retained activity when stored at 4° C. for 400 days or more. In contrast, as shown in FIG. 1, commercial standard composition APS-5 retained only about 65% performance after 300 days at 4° C., and <65% retained activity after about 400 days at 4° C.

Replacing TWEEN® 20 with non-ionic surfactants where the hydrophilic portion and the hydrophobic portion are linked via an ether bond led to significantly increased stability. Specifically, substrate compositions comprising ether-linked nonionic surfactants exhibited improved storage stability as shown in Table 6A compared to commercial standard APS-5 as shown in FIG. 1. Six of the 48 new formulations showed comparable signal intensity of current APS-5 formulation, and were continuously monitored showing less than 10% signal-loss over 15 months.

Example 4. Stability Studies with Alternative Nonionic Surfactant or Hydrophilic Polymer at Two Compound I Concentrations In this example, four newly made formulations were prepared for stability testing. One lot (20 L) of TRIS 0.3M pH 8.8 buffer was prepared. SDS, Sodium Sulfite, and Lucigenin were added, then the formulation was split into two parts. Two concentrations of CPA were added (0.15 g/l and 0.33 g/L). These two formulations were divided and PEG 100K was added to two of the formulations and TRITON X-405, 1.5 g/L was added to the other two formulations.

These 4 lots were measured with AP on a Spectramax-6L instrument (30 sec after injection). Only PMT (C) was employed. ALP was from BBI Solutions (Code ALP1125, lot 1698ADR); flat bottom 96 well white plates (Microlitre 1, Thermo Scientific Part 7416) were employed. Testing was performed by injecting 20 microliter of an ALP solution (1.5 ng/mL) into 200 microliter of the substrate formulation in a microtiter well on the instrument and read for 1 second under photon counting mode. Each formulation was tested in 48 replicates on a 96-well plate.

The formulations were stored at 4° C. (2-8° C.) and activity was assessed at monthly intervals. The 0.15 CPA formulation with PEG 100 exhibited a −0.7% loss of intensity per month with a p value of 0.002.

Figure 4:
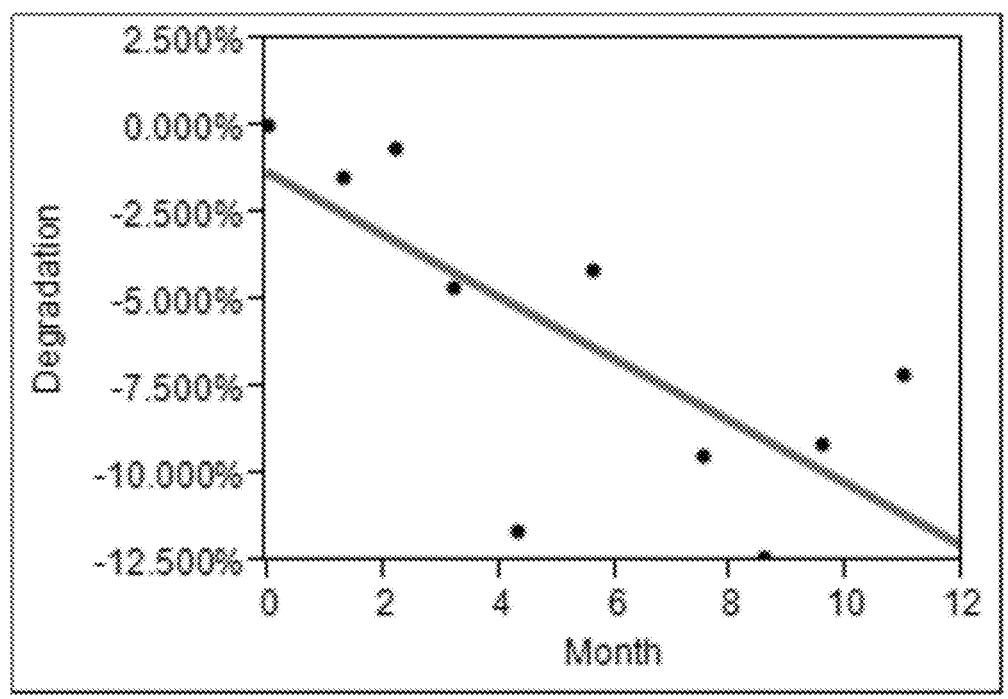
FIG. 4 shows stability over 12 months at 4° C. of a substrate formulation with 0.15 CPA g/L and TRITON X-405, according to Example 4.

FIG. 4 shows stability of the 0.15 CPA formulation with TRITON X-405. A slope of −0.9% loss of intensity per month (p value of 0.016) was determined when the formulation was stored at 2-8° C. As shown in representative FIG. 4, both formulations with either hydrophilic polymer PEG 100K (data not shown) or ether-based nonionic surfactant TRITON X-405 exhibited improved stability compared to standard APS-5 formulation with TWEEN® 20, shown in FIG. 1.

TABLES 6B-6E

Stability of four Fast Substrate Formulations comprising PEG 100K or TRITON X-405 at 4° C.

| Label | Mean RLU | Std Dev | C.V. | % of Fresh |
|---|---|---|---|---|
| 6B. PEG 100K with 0.15 g/L CPA | | | | |
| Fresh | 31874813 | 1689920 | 5.3% | 100% |
| 10-Month Old | 28991341 | 1777184 | 6.1% | 91.0% |
| 6C. TRITON X-405 with 0.15 g/L CPA | | | | |
| Fresh | 26539825 | 1559693 | 5.9% | 100% |
| 10-Month Old | 24761594 | 1478681 | 6.0% | 93.3% |
| 6D. PEG 100K with 0.33 g/L CPA | | | | |
| 7-Month Old | 6524830 | 4638140 | 7.1% | 86.1% |
| Fresh | 7576108 | 5932189 | 7.8% | 100% |
| 6E. TRITON X-405 with 0.33 g/L CPA | | | | |
| 7-Month Old | 4944601 | 2528690 | 5.1% | 91.8% |
| Fresh | 5387265 | 3132305 | 5.8% | 100% |

The substrate compositions of this example exhibited a fluorescence signal change in intensity (%) per month after 12 months when stored at 4° C. of ≤−1.0% per month; ≤−0.9%/month; or ≤−0.80%/month after exposure to an alkaline phosphatase enzyme.

As shown in FIG. 4, and Tables 6B to 6E, formulations comprising ether-linked nonionic surfactant TRITONX-405 and hydrophilic polymer PEG 100K exhibited >90% retained activity after 300 days when stored at 4° C. In contrast, as shown in FIG. 1, APS-5 retained only about 65% performance after 300 days at 4° C.

Example 5. Exemplary Substrate Formulations

Various substrate formulations were prepared from the materials as follows.

Formulation A: 0.30 g/L CPA, 3.26 mg/L Lucigenin, 10 mg/L sodium sulfite, 1.0 g/L PEG (35K), 1.0 g/L SDS, and 0.3 M TRIS, pH 9.2 buffer.

Formulation B: 0.30 g/L CPA, 3.26 mg/L Lucigenin, 5 mg/L sodium sulfite, 2.0 g/L TRITON-X-405, 1.0 g/L SDS, and 0.1 M AMPD, pH 9.7 buffer.

Formulation C: 0.30 g/L CPA, 3.26 mg/L Lucigenin, 10 mg/L sodium sulfite, 1.5 g/L BRIJ 78, 1.0 g/L SDS, and 0.3 M TRIS, pH 9.35 buffer.

Formulation D: 0.15 g/L CPA, 3.26 mg/L Lucigenin, 10 mg/L IGEPAL DM-970, 2.0 g/L IGEPAL DM-970, 1.0 g/L SDS, and 0.3 M TRIS, pH 9.35 buffer.

Formulation E (AMPD-10): 0.15 g/L CPA, 3.26 mg/L Lucigenin, 10 mg/L sodium sulfite, 1 g/L PEG (35K), 0.9 g/L SDS, and 0.1 M AMPD, pH 9.7 buffer.

Formulation F: 0.15 g/L CPA, 3.26 mg/L Lucigenin, 10 mg/L sodium sulfite, 1 g/L PEG (35K), 0.5 g/L STS, and 0.1 M AMPD, pH 9.7 buffer.

Formulation G (SMS-PEG-TRIS): 0.15 g/L CPA, 10 mg/L $Na_2SO_3$ (10 mg/L), 3.26 mg/L lucigenin, 1 g/L PEG 100K and 0.9 g/L SDS in 0.3 M TRIS buffer pH 9.2.

Formulation H: 0.30 g/L CPA, 2.45 mg/L Lucigenin, 10 mg/L sodium sulfite, 0.05 mM 4-tolylboronic acid, 1 g/L PEG (35K), 0.9 g/L SDS, and 0.1 M AMPD, pH 9.7 buffer.

Formulation I (SMS-PEG-AMPD): 0.15 g/L CPA, 3.26 mg/L Lucigenin, 10 mg/L sodium sulfite, 1 g/L PEG (35K), 0.9 g/L SDS, and 0.1 M AMPD, pH 9.7 buffer.

Formulation J (SMS-PEG): 0.15 g/L CPA, 3.26 mg/L Lucigenin, 10 mg/L sodium sulfite, 1.0 g/L PEG (35K), 1.0 g/L SDS, and 0.3 M TRIS, pH 9.2 buffer.

Formulation K (SMS-TRITON): 0.15 g/L CPA, 3.26 mg/L Lucigenin, 10 mg/L sodium sulfite, 2.0 g/L TRITON-X-405, 1.0 g/L SDS, and 0.3 M TRIS, pH 9.2 buffer.

Example 6. Substrate Assay Screening

Substrate formulations were evaluated to demonstrate feasibility for existing immunoassays while maintaining sensitivity and precision. Screening was done with SMS-PEG and SMS-TRITON, each containing 0.15 g/L CPA. LUMI-PHOS® 530 was also used as a control. Substrate formulation screening was performed on DxI 600019 with 3 luminometers, which read luminescence signal at L1=9 sec, L2=27 sec, L5=6.3 min respectively after addition of the substrate. Existing assay protocols are listed in FIG. 5. Old BHCG, New BHCG, AccuTnI+3, Myoglobin, CK-MB, BNP, Digoxin, TSH, TSH2 and PTH(1O) commercial assays were employed per manufacturers protocol, except the two substrate formulations were substituted for LUMI-PHOS® 530 substrate in the commercial immunoassays, and in addition to L5=6.3 min, the signals were also read at L1=9 sec and L2=27 sec. "PMP" in FIG. 5 refers to paramagnetic particles. Standard commercial assays employing LUMI-PHOS® 530 were used as controls for comparison.

For each substrate formulation 10 replicates of the S0 calibrator, 4 replicates of all other calibrator levels, 5 replicates of Bio-Rad controls, and 6 replicates of each low and high patient pooled serum samples were performed.

For each of the assay results shown in Tables 7-15, calibrator signal to noise ratios (S/N) were calculated by chemiluminescent assay signal ratio Sx/S0, where x is selected from 1, 2, 3, 4, or 5. Thus each S/N ratio for "S1" refers to S1/S0; "S2" refers to S2/S0; "S3" refers to S3/S0; "S4" refers to S4/S0; and "S5" refers to S5/S0, where S0 is the calibrator without analyte, and S1, S2, S3, S4, S5 are calibrators with increasing amounts of analyte.

Example 6A

Digoxin Screening comparison of calibrators S0, S1, S2, S3, S4 and S5; BioRad Liquichek control samples 1, 2, and 3, as well as Serum Pool 1 and Serum Pool 2 samples was performed with the SMS-PEG and SMS-TRITON substrate formulations compared to LUMI-PHOS® 530 commercial substrate formulation. As shown in FIG. 6A, RLUs at L2 and L5 for both SMS-PEG and SMS-TRITON substrate formulations was decreased compared to RLU for LUMI-PHOS® 530 at L5, with SMS-TRITON showing lowest RLU. However, similar B/B0 signals were observed compared to LUMI-PHOS® 530. Quality control analysis showed all samples were within stated range for both substrate formulations (data not shown).

Example 6B

Parathyroid hormone PTH (IO) screening comparison of calibrators S0, S1, S2, S3, S4 and S5; controls BioRad Specialty LTA, BioRad Liquichek samples 1, 2, and 3; and Serum Pool 1 and Serum Pool 2 samples was performed with the SMS-PEG and SMS-TRITON substrate formulations compared to LUMI-PHOS® 530 commercial substrate formulation, as shown in FIG. 6B. Controls showed somewhat different response in RLU signals with SMS-PEG compared to SMS-TRITON substrate formulations. Improved calibrator Signal to Noise ratios, calculated as S/S0, was seen with both substrate formulations compared to LUMI-PHOS® 530, as shown in Table 7. With respect to Quality assessment, all controls stayed within stated range for both substrate formulations. However, LUMI-PHOS® 530 was out of range for LTA and Level 1 samples.

TABLE 7

Signal to Noise (S/N) for substrate formulations of the present invention compared to LUMI-PHOS ® 530 in PTH(IO) Screening Assay.

| Level | LP-530 | SMS-PEG | SMS-TRITON |
|---|---|---|---|
| S1 | 2 | 3 | 3 |
| S2 | 7 | 13 | 10 |
| S3 | 30 | 60 | 46 |
| S4 | 142 | 273 | 218 |
| S5 | 325 | 609 | 496 |

Example 6C

Thyrotropin (thyroid-stimulating hormone) TSH screening comparison was performed with calibrators S0, S1, S2, S3, S4 and S5; controls BioRad QC 1, 2, and 3, as well as Serum Pool 1 and Serum Pool 2 samples with the SMS-PEG and SMS-TRITON substrate formulations compared to LUMI-PHOS® 530 commercial substrate formulation. As shown in FIG. 6C, higher signals were exhibited by the SMS-PEG substrate, and lower signals were seen with SMS-TRITON compared to LUMI-PHOS® 530. Better signal to noise ratios were exhibited by both substrates as compared to LUMI-PHOS® 530 as shown in Table 8. With respect to Quality assessment, all BioRad QC controls stayed within stated range for both substrate formulations of the present invention.

TABLE 8

Signal to Noise (S/N) values for substrate formulations of the present invention compared to LUMI-PHOS ® 530 in TSH Screening Assay.

| Level | LP-530 | SMS-PEG | SMS-TRITON |
|---|---|---|---|
| S1 | 5 | 12 | 10 |
| S2 | 20 | 61 | 43 |
| S3 | 145 | 470 | 323 |
| S4 | 348 | 1075 | 763 |
| S5 | 2065 | 5949 | 4970 |

Example 6D

Thyrotropin (thyroid-stimulating hormone) TSH2 screening was performed with comparison was performed with calibrators S0, S1, S2, S3, S4 and S5; controls BioRad QC 1, 2, and 3, as well as Serum Pool 1 and Serum Pool 2 samples with the SMS-PEG and SMS-TRITON substrate formulations compared to LUMI-PHOS® 530 commercial substrate formulation. As shown in FIG. 6D, similar RLU was exhibited with SMS-PEG, while lower signals were exhibited by SMS-TRITON substrates compared to LUMI-PHOS® 530. L2 (27 sec) shows higher signal than L5 (6.3 min) for both substrates. Better signal to noise ratio was exhibited with both substrate formulations, with SMS being better than SMS-TRITON, as shown in Table 9. All controls stayed within ranges except QC2 for SMS-TRITON.

TABLE 9

Signal to Noise (S/N) values for substrate formulations of the present invention compared to LUMI-PHOS ® 530 in TSH2 Screening Assay.

| Level | LP-530 | SMS-PEG | SMS-TRITON |
|---|---|---|---|
| S1 | 10 | 23 | 14 |
| S2 | 53 | 123 | 80 |
| S3 | 474 | 1165 | 759 |
| S4 | 1908 | 5036 | 3330 |
| S5 | 3967 | 10627 | 8259 |

Example 6E

AccuTnI+3 screening was performed with calibrators S0, S1, S2, S3, S4 and S5; controls BioRadCard-01, -02 and -03; as well as Serum Pool—Low, Serum Pool—High and Negative Serum—ALL samples with the SMS-PEG and SMS-TRITON substrate formulations compared to LUMI-PHOS® 530 commercial substrate formulation. As shown in FIG. 6E, serum may be showing a different response than calibrators, compared to LUMI-PHOS® 530 for both substrate formulations. Higher S0 was seen with SMS-PEG at L5 compared to L2. S0 variability was higher for both substrate formulations of the present invention. Better signal to noise was exhibited by both substrate formulations compared to LUMI-PHOS® 530 as shown in Table 10.

TABLE 10

Signal to Noise (S/N) values for substrate formulations of the present invention compared to LUMI-PHOS ® 530 in AccuTnI + 3 Screening Assay.

| Level | LP-530 | SMS-PEG | SMS-TRITON |
|---|---|---|---|
| S1 | 7 | 10 | 8 |
| S2 | 26 | 37 | 32 |
| S3 | 104 | 153 | 131 |
| S4 | 513 | 741 | 672 |
| S5 | 1541 | 2547 | 2266 |

Example 6F

BNP (B-type natriuretic peptide) screening was performed with calibrators S0, S1, S2, S3, S4 and S5; controls BNP-QC 1, BNP-QC 2, BNP-QC 3; and Serum Pool 1 and Serum Pool 2 with the SMS-PEG and SMS-TRITON substrate formulations compared to LUMI-PHOS® 530 commercial substrate formulation, as shown in FIG. 6F. An improved signal to noise ratio was seen with both substrate formulations of the present invention compared to LUMI-PHOS® 530, as shown in Table 11. Serum samples showed lower RLU compared to calibrators for both substrate formulations of the present invention, and it was noted that EDTA plasma is the only approved sample type.

TABLE 11

Signal to Noise (S/N) values for substrate formulations of the present invention compared to LUMI-PHOS ® 530 in BNP Screening Assay.

| Level | LP-530 (L5) | SMS-PEG (L2) | SMS-TRITON (L2) |
|---|---|---|---|
| S0 | 1 | 1 | 1 |
| S1 | 8 | 17 | 16 |
| S2 | 27 | 64 | 61 |
| S3 | 143 | 353 | 313 |
| S4 | 869 | 2292 | 1990 |
| S5 | 1645 | 4630 | 4110 |

Example 6G

CK-MB (Creatine Kinase-MB) screening was performed with calibrators S0, S1, S2, S3, S4 and S5; controls BioRad Cardiac 1, BioRad Cardiac 2 and BioRad Cardiac 3; and Serum Pool 1 and Serum Pool 2 with the SMS-PEG and SMS-TRITON substrate formulations compared to LUMI-PHOS® 530 commercial substrate formulation, as shown in FIG. 6G. As shown in FIG. 6G, similar S0 RLUs were seen with both substrate formulations. Much lower RLU values were seen for all calibrator levels with SMS-TRITON. A better signal to noise ratio was seen with both substrate formulations compared to LUMI-PHOS® 530, as shown in Table 12.

TABLE 12

Signal to Noise (S/N) values for substrate formulations of the present invention compared to LUMI-PHOS ® 530 in CK-MB Screening Assay.

| Level | LP-530 | SMS-PEG | SMS-TRITON |
|---|---|---|---|
| S1 | 11 | 28 | 20 |
| S2 | 36 | 95 | 65 |
| S3 | 107 | 279 | 192 |
| S4 | 371 | 959 | 670 |
| S5 | 1151 | 2841 | 2052 |

Example 6H

Myoglobin screening was performed with calibrators S0, S1, S2, S3, S4 and S5; controls BioRad Cardiac 1, BioRad Cardiac 2 and BioRad Cardiac 3; and Serum Pool 1 and Serum Pool 2 with the SMS-PEG and SMS-TRITON substrate formulations compared to LUMI-PHOS® 530 commercial substrate formulation, as shown in FIG. 6H. An increased RLU signal was seen at all calibrator levels, QC and serum samples with SMS-PEG compared to LUMI-PHOS® 530. An improved signal to noise ratio was seen with both substrate formulations of the present invention compared to SP-530, as shown in Table 13. This screening assay exhibited the highest S0 values observed so far of the various screening assays. All controls stayed within stated ranges for both substrate formulations of the present invention.

TABLE 13

Signal to Noise (S/N) values for Substrate formulations of the present invention compared to LUMI-PHOS ® 530 in Myoglobin Screening Assay.

| Level | LP-530 | SMS-PEG | SMS-TRITON |
|---|---|---|---|
| S1 | 12 | 38 | 32 |
| S2 | 46 | 157 | 134 |
| S3 | 209 | 689 | 577 |
| S4 | 507 | 1668 | 1341 |
| S5 | 833 | 2659 | 2281 |

Example 6I

Total BHCG (old) (beta-human Chorionic Gonadotropin) screening was performed with calibrators S0, S1, S2, S3, S4 and S5; controls BioRad-01, -02, -03; and Negative Patient serum with the SMS-PEG and SMS-TRITON substrate formulations compared to LUMI-PHOS® 530 commercial substrate formulation, as shown in FIG. 6I. RLUs were lower for both substrate formulations of the present invention compared to LUMI-PHOS® 530. Signal to noise ratios were better for both substrate formulations of the present invention compared to LUMI-PHOS® 530, as shown in Table 14. All controls stayed within stated ranges for both substrate formulations of the present invention.

TABLE 14

Signal to Noise (S/N) values for Substrate formulations of the present invention compared to LUMI-PHOS ® 530 in Total BHCG (old) Screening Assay.

| Level | LP-530 | SMS-PEG | SMS-TRITON |
|---|---|---|---|
| S1 | 2 | 4 | 3 |
| S2 | 7 | 15 | 12 |
| S3 | 38 | 92 | 63 |
| S4 | 121 | 273 | 205 |
| S5 | 248 | 602 | 406 |

Example 6J

Total BHCG (New) screening was performed with calibrators S0, S1, S2, S3, S4 and S5; controls BioRad-01, -02, -03; and Negative Patient serum with the SMS-PEG and SMS-TRITON substrate formulations compared to LUMI-PHOS® 530 commercial substrate formulation, as shown in FIG. 6J. RLUs for both substrate formulations of the present invention were lower compared to LUMI-PHOS® 530. Signal to Noise ratios were better for both substrate formulations of the present invention compared to LUMI-PHOS® 530 as shown in Table 15. All controls stayed within stated ranges for both substrate formulations of the present invention.

TABLE 15

Signal to Noise (S/N) values for Substrate formulations of the present invention compared to LUMI-PHOS ® 530 in Total BHCG (New) Screening Assay.

| Level | LP-530 | SMS-PEG | SMS-TRITON |
|---|---|---|---|
| S1 | 5 | 6 | 6 |
| S2 | 24 | 32 | 31 |
| S3 | 125 | 176 | 166 |

TABLE 15-continued

Signal to Noise (S/N) values for Substrate formulations of
the present invention compared to LUMI-PHOS ® 530
in Total BHCG (New) Screening Assay.

| Level | LP-530 | SMS-PEG | SMS-TRITON |
|---|---|---|---|
| S4 | 395 | 551 | 501 |
| S5 | 725 | 1091 | 1004 |

In each of examples 6A-6J, Tables 7-15, substrate formulations with SMS-PEG and SMS-TRITON exhibited higher calibrator signal to noise ratios than LP-530 substrate.

Example 6K

All assays show S0 values higher than Lumblank ratios, as shown in Tables 16 and 17. Comparing results across each of the assays, TSH2 shows the lowest S0 RLU with LUMI-PHOS® 530, as shown in Table 17.

TABLE 16

Selected Average Lumblank values.

| Average LumBlank | LP-530 | SMS-PEG | SMS-TRITON |
|---|---|---|---|
| Blank 1-BhCG runs | 7,509 | 2,050 | 2,366 |
| Blank 2-TnI runs | 7,309 | 2,009 | 2,215 |
| Blank 3-Remaining Assays | 7,560 | 2,070 | 2,290 |

TABLE 17

Average S0 RLUs in Screening Assays

| Analyte | LP-530 | SMS-PEG | SMS-TRITON |
|---|---|---|---|
| TSH | 10,365 | 4,445 | 3,981 |
| TSH2 | 8,578 | 3,249 | 3,584 |
| BNP | 10,480 | 3,704 | 3,248 |
| PTH-IO | 10,584 | 4,518 | 3,948 |
| Myoglobin | 16,717 | 5,846 | 5,022 |
| CKMB | 12,043 | 3,341 | 3,228 |
| AccuTnI + 3 | 10,460 | 2,643 | 2,274 |
| New BHCG | 11,004 | 2,544 | 2,392 |
| Old BHCG | 13,476 | 4,586 | 5,428 |

The SMS-PEG and SMS-TRITON test formulations were compared to LUMI-PHOS® 530 in terms of RLU S0/blank ratios in AccuTnI+3, NextGenTnI+3, BNP, CKMB, Myoglobin, Old BHCG, New BHCG, PTH-IO, TSH, and TSH2 assays (data not shown). In all cases the S0 RLUs were higher than the blank RLUs. The S0/blank ratios with substrate formulations of the present invention SMS-PEG and SMS-TRITON test formulations were all higher than those with LUMI-PHOS® 530 except in the CKM assay (where the ratios from substrate formulations of the present invention were equal to that from LUMI-PHOS® 530) and in New BHCG assay (where the ratios from substrate formulations of the present invention were slightly lower, 1.25 vs 1.5). Myoglobin showed the highest S0/blank ratio with substrate formulations of the present invention. Higher S0/blank ratios are desirable for development of sensitive assays.

Signal to Noise ratios with sandwich assays were similar or better than the current LUMI-PHOS® 530 for both substrate formulations of the present invention. Fast substrate RLU S0 variability was higher than LUMI-PHOS® 530 in most assays except for Digoxin and Old BHCG.

Variability in dose with high and low serum pools compared to LUMI-PHOS® 530 for both substrate formulations of the present invention SMS-PEG and SMS-TRITON is shown in FIG. 10, providing a variability chart for % difference of dose compared to LUMI-PHOS® 530. Lower % difference of dose compared to LUMI-PHOS® 530 is seen with BNP, Digoxin, Myoglobin in both lower and high serum pools with both substrate formulations of the present invention. Higher % difference of dose compared to LUMI-PHOS® 530 is seen in Accu TnI+3, CKMB, PTH(IO), TSH and TSH2 in low and high serum pools with both substrate formulations of the present invention.

In summary, RLU signals are lower than LUMI-PHOS® 530 with most assays for both substrate formulations of the present invention except for Myoglobin and TSH with SMS-PEG. In general, SMS-PEG shows higher RLU's than SMS-TRITON for all assays. In addition, L1 (9 sec) is not the peak for signal generation for any of the assays tested.

With respect to background, lower lumblanks were exhibited for both substrate formulations of the present invention compared to LUMI-PHOS® 530, and the S0 values were never lower than Lumblanks. The S0 RLU's were lower than LUMI-PHOS® 530 for both substrate formulations of the present invention. The Signal to Noise was better than LUMI-PHOS® 530 for all assays.

With respect to imprecision, higher Lumblank variability was seen for both substrate formulations of the present invention. Sandwich assays show more S0 imprecision with both substrate formulations of the present invention except for Old BHCG with SMS-PEG. The curve fit was found to be acceptable for all assays for all assays. However, a dose bias was seen with controls and patient samples for some assays.

Example 7. Alternative Buffer Systems

An alkaline phosphatase enzyme normally requires non-phosphate basic buffers. The preferred buffers in present invention are amine-based buffers that have pH values greater than 8.0. Alternative buffers were investigated to improve stability, and maintain signal. FIG. 7 shows buffer parameters investigated as alternative amine buffers including TRIS, AMPD, DEA, AMPSO, 221-Amine, CHES, or TAPS. Multiple buffer systems were investigated to gauge the impact of molarity and pH on signal. In this experiment, signal was measured on a SpectraMax plate reading luminometer and compared to a standard Fast Substrate formulation comprising TRIS 0.3 M pH 8.8 as follows.

Formulations employing various buffer systems were prepared with CPA-0.15 g/L, Lucigenin-3.26 mg/L, Sodium Sulfite-10 mg/L, PEG Mw=35K-1 g/L, SDS-0.9 g/L in various buffers shown in Table 18A. Table 18A shows Signals relative (%) to a reference formulation in 0.3 M TRIS pH 8.8.

TABLE 18A

Buffer Systems - Signals relative (%) to 0.3M TRIS pH 8.8

| Buffer | Chemiluminescence Signal (%)* |
|---|---|
| TAPS 0.025M pH 9.2 | 70 |
| TAPS 0.1M pH 9.2 | 95 |
| CBES 0.025M pH 10 | 115 |

TABLE 18A-continued

Buffer Systems - Signals relative (%) to 0.3M TRIS pH 8.8

| Buffer | Chemiluminescence Signal (%)* |
|---|---|
| CBES 0.025M pH 9.8 | 110 |
| CBES 0.1M pH 9.8 | 60 |
| 221-Amine 0.025M pH 10.1 | 130 |
| 221-Amine 0.1M pH 10.1 | 40 |
| AMPD 0.025M pH 9.7 | 95 |
| AMPD 0.05M pH 9.7 | 132 |
| AMPD 0.1M pH 9.7 | 142 |
| AMPD 0.2M pH 9.7 | 117 |
| AMPD 0.1M pH 9.4 | 131 |
| AMPD 0.1M pH 9.2 | 130 |
| AMPSO 0.1M pH 9.2 | 110 |
| AMPSO 0.2M pH 9.2 | 85 |
| AMPSO 0.1M pH 9.0 | 86 |
| DEA 0.1M pH 9.2 | 88 |
| DEA 0.2M pH 9.2 | 57 |
| TRIS 0.1M pH 9.2 | 91 |
| TRIS 0.2M pH 9.2 | 120 |
| TRIS 0.3M pH 9.2 | 132 |
| TRIS 0.4M pH 9.2 | 130 |
| TRIS 0.5M pH 9.2 | 128 |
| TRIS 0.6M pH 9.2 | 119 |

*Signals are relative (%) to a reference formulation in 0.3M TRIS pH 8.8)

Due to the narrow pH and Molarity usable range, one formulation was chosen for each of these buffer systems as shown in Table 18B.

TABLE 18B

Alternative Amine Buffer Systems

| Buffer | Molarity | pH | Background | Signal % | S %/BG |
|---|---|---|---|---|---|
| *Tris* | *0.3* | *8.8* | *2.6* | *100* | *38.5* |
| TAPS | 0.1 | 9.2 | 4.1 | 95 | 23.2 |
| CHES | 0.025 | 10.0 | 3.9 | 116 | 29.7 |
| 221 | 0.025 | 10.1 | 3.0 | 120 | 40.0 |
| DEA | 0.1 | 9.2 | 4.6 | 88 | 19.1 |
| AMPSO | 0.1 | 9.2 | 4.2 | 110 | 26.2 |

The 221-amine intensity varied significantly from prep to prep, most likely due to the greatest dependence of performance on molarity. The TAPS buffer caused precipitation after refrigeration. The AMPSO buffer exhibited the highest C.V.s in testing. Therefore, none of these 5 TAPS, CHES, 221-amine, DEA or AMPSO buffers was further investigated.

The AMPD buffer showed comparable performance to TRIS buffer in terms of signal intensity and background over a wide range of pH and molarity as shown in Table 19.

TABLE 19

AMPD Buffer Performance

| Buffer | Molarity | pH | Background | Signal % | S %/BG |
|---|---|---|---|---|---|
| Tris | 0.3 | 8.8 | 2.6 | 100 | 38.5 |
| AMPD | 0.05 | 9.2 | 3.5 | 103 | 29.4 |
| AMPD | 0.1 | 9.2 | 3.2 | 120 | 37.5 |
| AMPD | 0.2 | 9.2 | 4.0 | 102 | 25.5 |
| AMPD | 0.05 | 9.4 | 3.4 | 126 | 37.1 |
| AMPD | 0.1 | 9.4 | 3.3 | 131 | 39.7 |
| AMPD | 0.2 | 9.4 | 3.4 | 118 | 34.7 |
| AMPD | 0.05 | 9.7 | 3.4 | 132 | 38.8 |
| AMPD | 0.1 | 9.7 | 3.4 | 142 | 41.8 |
| AMPD | 0.2 | 9.7 | 3.1 | 117 | 37.7 |

Figure 8:
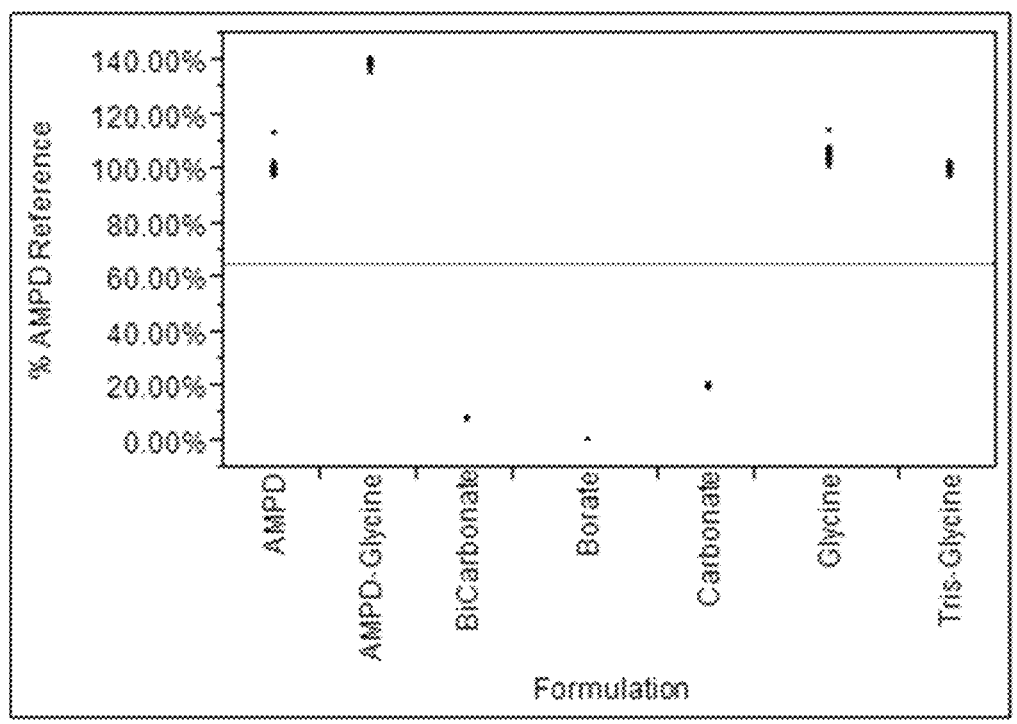
FIG. 8 shows comparative signal with AP of substrate formulations comprising various buffer systems as % of a reference substrate formulation comprising an AMPD buffer system. Test substrate formulations comprising bicarbonate, borate, and carbonate buffer systems each exhibited diminished signal with AP compared to AMPD reference. Test formulations comprising glycine and TRIS-glycine buffers exhibited similar signal with AP compared to AMPD reference. Test substrate formulation comprising AMPD-Glycine exhibited increased signal compared to AMPD reference.

AMPD buffer system alone with CPA (0.15 g/L), $Na_2SO_3$ (10 mg/L), lucigenin (3.26 mg/L), PEG (1.0 g/L) and SDS (0.9 g/L) was compared to different buffers AMPD-Glycine, bicarbonate, borate, carbonate, glycine and Tris-glycine was investigated. The signal with AP as % of AMPD reference is shown in FIG. 8. Bicarbonate, Borate, Carbonate each exhibited significantly diminished signal with AP compared to AMPD. Glycine and Tris-Glycine buffers exhibited similar signal to AMPD. AMPD-Glycine exhibited increased signal compared to AMPD reference.

AMPD formulations were prepared using CPA (0.15 g/L), $Na_2SO_3$ (10 mg/L), lucigenin (3.26 mg/L), PEG (1.0 g/L) and SDS (0.9 g/L) in AMPD buffer at nine different pH and molarity combinations and tested for stability at 30° C. as shown in Table 20.

TABLE 20

AMPD Stability Summary Data - % loss of Performance after storage

| | Day 5 | Day 8 | Day 12 | Day 15 | % per day 15 | Slope % per day |
|---|---|---|---|---|---|---|
| Control | 3.2 | 5.8 | 6.4 | 8.2 | 0.55 | −0.53 |
| 0.05M AMPD pH 9.7 | 5.8 | 4 | 6.2 | 8 | 0.53 | −0.46 |
| 0.1M AMPD pH 9.7 | 2.4 | 2.4 | 3.3 | 3.5 | 0.23 | −0.19 |
| 0.2M AMPD pH 9.7 | 3.9 | 2.9 | 5.5 | 4.2 | 0.28 | −0.28 |
| 0.05M AMPD pH 9.4 | 1.5 | 4.6 | 4.8 | 5.5 | 0.37 | −0.39 |
| 0.1M AMPD pH 9.4 | 3.7 | 3.9 | 4.7 | 5.1 | 0.34 | −0.32 |
| 0.2M AMPD pH 9.4 | 3.3 | 3.2 | 6.3 | 1.8 | 0.12 | −0.20 |
| 0.05M AMPD pH 9.2 | 3.7 | 5 | 4.5 | 6.2 | 0.41 | −0.36 |
| 0.1M AMPD pH 9.2 | 1 | 3.9 | 3.5 | 6.5 | 0.43 | −0.41 |
| 0.2M AMPD pH 9.2 | 2.7 | 5.5 | 5.5 | 5.9 | 0.39 | −0.40 |

The p-value for all slopes indicated statistical significance.

TRIS buffer was further investigated relative to molarity and pH. Compositions were prepared comprising CPA (0.15 g/L), $Na_2SO_3$ (10 mg/L), lucigenin (3.26 mg/L), PEG (1.0 g/L) and SDS (0.9 g/L) in TRIS buffer pH 9.2 at indicated molarity shown in Table 21. Performance is shown in Table 21 relative to control TRIS buffer, italicized in line 1.

TABLE 21

TRIS Performance Summary

| Buffer | Molarity | pH | Background | Signal % | S %/BG |
|---|---|---|---|---|---|
| *Tris* | *0.3* | *8.8* | *2.6* | *100* | *38.5* |
| Tris | 0.3 | 9.2 | 3.0 | 132 | 44.0 |
| Tris | 0.4 | 9.2 | 3.0 | 130 | 43.3 |
| Tris | 0.5 | 9.2 | 3.4 | 128 | 37.6 |
| Tris | 0.75 | 9.2 | 3.3 | 104 | 31.5 |

As shown in Table 21, TRIS showed comparable performance over a wide range of pH and molarity. The pH was limited to 9.2, because higher pH are outside of TRIS buffering capacity. Four formulation combinations were tested for stability at 30° C. Results are shown in Table 22.

TABLE 22

TRIS Stability Summary Data

| TRIS Molarity | % Loss Tris | | | | Slope % |
|---|---|---|---|---|---|
| | Day 5 | Day 11 | Day 14 | Day 17 | % per day 17 | per day |
| Control | 5.4 | 7.2 | 6.4 | 9.5 | 0.56 | −0.51 |
| 0.75 | 5.3 | 7.3 | 8.1 | 11.9 | 0.70 | −0.60 |
| 0.5 | 2.7 | 7.2 | 5 | 7.3 | 0.43 | −0.43 |
| 0.4 | 6.6 | 6.1 | 7 | 7 | 0.50 | −0.41 |
| 0.3 | 5.2 | 5.3 | 7.7 | 5.8 | 0.41 | −0.361 |

Four Buffer systems were further investigated: AMPD buffer with 10 mg·L sodium sulfite; AMPD buffer with 25 mg/L sodium sulfite; Tris 10 mg/L sodium sulfite; and Tris 25 mg/L sodium sulfite. In general, replacing TRIS buffer with 2-amino-2-methyl-1,3-propanediol (AMPD) buffer resulted in improvement in stability of the substrate formulations of the present invention.

Example 8. Comparison of Alkaline Phosphatases

A comparison of Alkaline Phosphatases was performed using Biozyme ALP, Recombinant ALP and Native ALP. Performance of Fast substrate test formulations containing SMF-PEG-AMPD (AMPD-10), or SMF-PEG-TRIS were compared to LUMI-PHOS® 530. The SMF-PEG-AMPD (AMPD-10) formulation contained CPA (0.15 g/L), $Na_2SO_3$ (10 mg/L), lucigenin (3.26 mg/L), PEG 35K (1.0 g/L) and SDS (0.9 g/L) in 0.1 M AMPD pH 9.7. The SMF-PEG-TRIS formulation contained CPA (0.15 g/L), $Na_2SO_3$ (10 mg/L), lucigenin (3.26 mg/L), PEG 35K (1.0 g/L) and SDS (0.9 g/L) in 0.3 M TRIS buffer pH 9.2

Each formulation (200 uL) was tested with 20 uL ALP on a SpectraMax using 24 replicates. Biozyme ALP was used at 1.8 ng/mL, Recombinant and Native ALP were used at 2 ng/mL. Results are shown in Tables 22A-D.

TABLE 22A

Biozyme ALP

| | SMF-PEG-AMPD | SMF-PEG Tris | LUMI-PHOS® 530 |
|---|---|---|---|
| Replicates | 24 | 24 | 24 |
| Average | 46520787 | 44070031 | 1774925 |
| STDEV | 2270222 | 3167308 | 204434 |
| % CV | 4.9 | 7.2 | 11.5 |

TABLE 22B

Recombinant ALP

| | SMF-PEG-AMPD | SMF-PEG Tris | LUMI-PHOS® 530 |
|---|---|---|---|
| Replicates | 24 | 24 | 24 |
| Average | 45882022 | 41260028 | 2096930 |
| STDEV | 2300294 | 2012509 | 226116 |
| % CV | 5.0 | 4.9 | 10.8 |

TABLE 22C

Native ALP

| | SMF-PEG-AMPD | SMF-PEG Tris | LUMI-PHOS® 530 |
|---|---|---|---|
| Replicates | 24 | 24 | 24 |
| Average | 25106620 | 23810036 | 1007152 |
| STDEV | 1421989 | 1213361 | 134862 |
| % CV | 5.7 | 5.1 | 13.4 |

TABLE 22D

Ratio of RLU compared to Native ALP

| Ratio | Biozyme ALP | Recomb. ALP | Native ALP |
|---|---|---|---|
| SMF-PEG AMPD-10 | 1.9 | 1.8 | 1 |
| SMF-PEG Tris | 1.9 | 1.7 | 1 |
| LUMI-PHOS® 530 | 1.8 | 2.1 | 1 |

Each substrate formulation of the present invention was amenable for use with Biozyme ALP, recombinant ALP, or native ALP. Two substrate formulations with SMF-PEG-AMPD (AMPD-10) and SMF-PEG-TRIS exhibited lower % CV than LUMI-PHOS® 530, as shown in Tables 22A-22C.

Example 9. Alternative Anionic Surfactant

The original APS-5 formulation comprises sodium dodecyl sulfate (SDS) anionic surfactant. Comparative stability of alternative formulations employing AMPD buffers and SDS or STS anionic surfactants was investigated. Table 23 shows three alternative substrate formulations of the present invention for use with CPA.

TABLE 23

Alternative Formulations for Stability Study

| | Formulation Name | | |
|---|---|---|---|
| Component | "AMPD-10" Concentration | "C13" Concentration | "Glycine" Concentration |
| AMPD | 0.1M/10.5 g/L | 0.1M/10.5 g/L | 0.05M/5.25 g/L |
| HCl | 14 mM/1.2 g/L | 14 mM/1.2 g/L | — |
| Glycine | — | — | 16 mM/1.05 g/L |
| Sodium sulfite | 10 mg/L | 10 mg/L | 5 mg/L |
| Lucigenin | 3.26 mg/L | 3.26 mg/L | 2.0 mg/L |
| SDS | 0.9 g/L | — | — |
| STS | — | 0.5 g/L | 0.5 g/L |
| CPA | 0.15 g/L | 0.15 g/L | 0.15 g/L |
| PEG Mn = 35,000 | 1.0 g/L | 1.0 g/L | 1.0 g/L |

Mechanistic study has shown that N-methyl acridone is a product from degradation of compound I CPA, as illustrated in Scheme 1. The fluorescence intensity of N-methyl acridone degradant in the formulation was used as another indicator for formulation stability in this investigation. Three test formulations were prepared and compared to APS-5 formulation as follows.

Formulation APS-5: CPA, 0.3 M TRIS buffer pH 9.35, lucigenin, $Na_2SO_3$ (10 mg/L), SDS (1 g/L), TWEEN® 20 (w/v, 2 g/L);

Formulation AMPD-10: CPA (0.15 g/L), 0.1 M AMPD buffer pH 9.7, lucigenin (3.26 mg/L), $Na_2SO_3$ (10 mg/L), SDS (0.9 g/L), PEG (Mw 35K, 1.0 g/L);

Formulation STS: CPA (0.15 g/L), 0.1 M AMPD buffer pH 9.7, lucigenin (3.26 mg/L), $Na_2SO_3$ (10 mg/L), STS (0.5 g/L), PEG (Mw 35K, 1.0 g/L);

Formulation Glycine: CPA (0.15 g/L), 0.05 M AMPD-Glycine buffer pH 9.7, lucigenin (2.0 mg/L), $Na_2SO_3$ (5 mg/L), STS (0.5 g/L), PEG (Mw 35K, 1.0 g/L).

AMPD-10, C13, and Glycine formulations were compared to APS-5 when stored at 5° C., 18° C., or 30° C. over a period of 15 days. Fluorescence at each time point was compared to day 0. Results are shown in FIG. 9 A-9C as graphs of fluorescence compared to day 0 at 5° C., 18° C. and 30° C. for 15 days for each of the 4 formulations: A=APS-5; B=AMPD-10; C=C13; and D=Glycine.

Figure 9A:
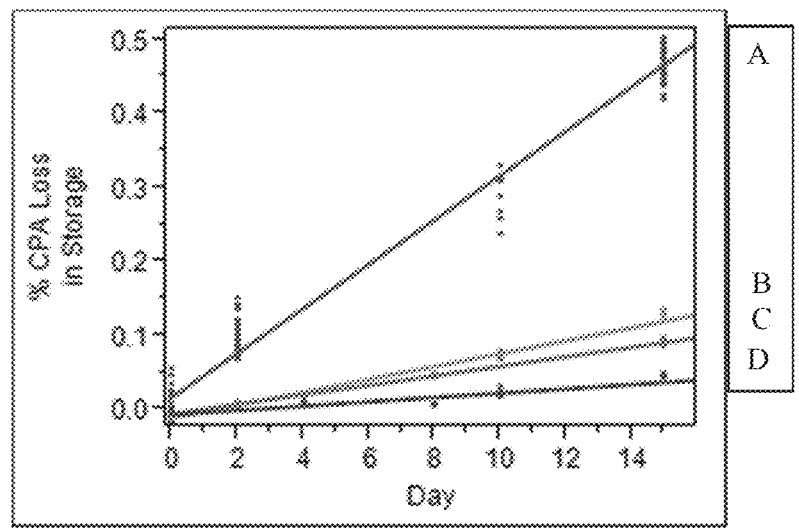
FIG. 9A shows percent CPA loss in storage at 5° C. for 15 days for APS-5 (A); AMPD-10 (B); C13 (C); and Glycine (D) substrate formulations.

FIG. 9A shows percent CPA loss in storage at 5° C. for 15 days. At 5° C., the glycine formulation (slope=0.0029% CPA loss/day, R2 0.85, P<0.001) exhibited the best stability in terms of least % loss of CPA, followed by C13 (slope=0.0054, R2 0.97, P<0.001), AMPD-10 (Slope=0.0067, R2 0.96, P<0.001), and APS-5 (slope 0.030, R2 0.99, P<0.001).

Figure 9B:
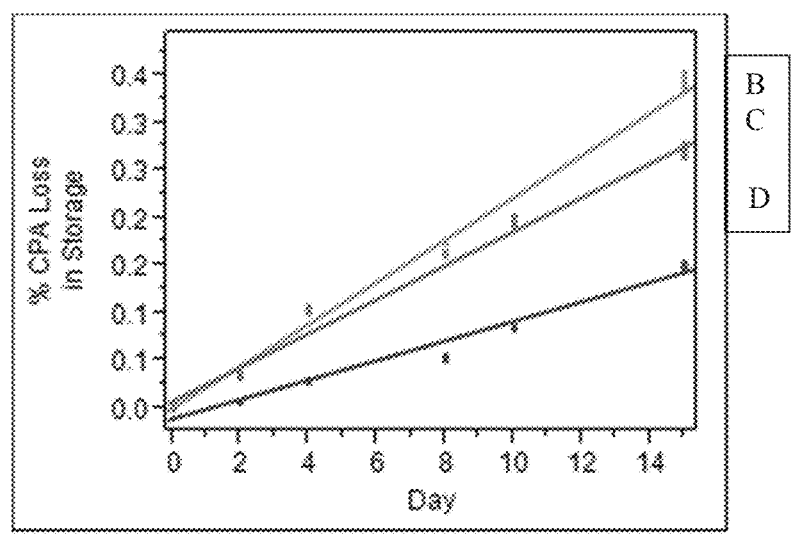
FIG. 9B shows percent CPA loss in storage at 18° C. for 15 days for AMPD-10 (B); C13 (C); and Glycine (D) substrate formulations.

FIG. 9B shows percent CPA loss in storage at 18° C. for 15 days. At 18° C., the glycine formulation (slope=0.010% CPA loss/day, R2 0.65, P<0.001) exhibited the best stability in terms of least % loss of CPA, followed by C13 (slope=0.018, R2 0.98, P<0.001), and AMPD-10 (Slope=0.022, R2 0.99, P<0.001).

Figure 9C:
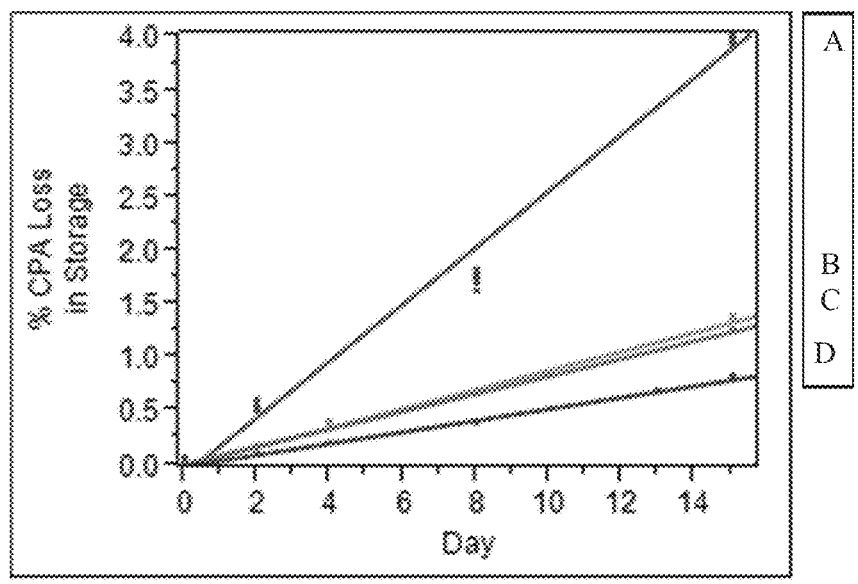
FIG. 9C shows percent CPA loss in storage at 30° C. for 15 days for APS-5 (A); AMPD-10 (B); C13 (C); and Glycine (D) substrate formulations.

FIG. 9C shows percent CPA loss in storage at 30° C. for 15 days. At 30° C., the glycine formulation (slope=0.054% CPA loss/day, R2 0.99, P<0.001) exhibited the best stability in terms of least % loss of CPA, followed by C13 (slope=0.082, R2 0.99, P<0.001), AMPD-10 (Slope=0.089, R2 0.99, P<0.001), and APS-5 (slope 0.265, R2 0.99, P<0.001).

Fluorescence change per day after 15 days at 30° C. is shown in Table 24.

TABLE 24

| Formulation | Fluorescence Change % per Day after 15 Days at 30° C., |
|---|---|
| APS-5 | 0.265 |
| AMPD-10 | 0.089 |
| C13 | 0.082 |
| Glycine | 0.054 |

Each of the alternative AMPD-10, C13, and Glycine formulations without TWEEN® 20 exhibited substantially increased CPA stability over 15 days at 5° C., 18° C. and 30° C., as indicated by decreased fluorescence change from day 0 compared to the APS-5 formulation, as shown in FIGS. 9A-C and summarized in Table 24.

Example 10. Boronic Acid Background Reducing Agents in AMPD-10

A stability study of the AMPD-10 formulation containing added background reducing agents selected from aryl boronic acids was performed. Aryl boronic acids including phenyl boronic acid, 4-tolyl boronic acid, 4-chloroboronic acid, 4-iodoboronic acid and 3-methoxycarbonylphenyl boronic acid were investigated.

AMPD-10 formulations were prepared and boronic acids were added as follows: 0.15 g CPA, 1.0 g/L PEG 35K, 0.9 g/L SDS, 10 mg/L $Na_2SO_3$, 3.26 mg/L lucigenin, 0.1 M 2-amino-2-methyl-1,3-propanediol (AMPD) pH 9.7 buffer. Boronic acids were employed at 0.25 mM (from stocks in DMF). The effect of added boronic acids is shown in Table 25.

TABLE 25

Effect of Boronic Acids in AMPD-10

| Boronic Acid (at 0.25 mM) | Background | | Signal | | S/N | |
|---|---|---|---|---|---|---|
| | Mean RLU | Change (%) | Mean RLU | Change (%) | S/N | Change (%) |
| AMPD-ctrl | 396 | | 82157 | | 207 | |
| Ph | 142 | −64 | 46980 | −43 | 331 | 60 |
| 4-Cl—Ph | 154 | −61 | 50751 | −38 | 330 | 59 |
| 4-Me—Ph | 138 | −65 | 43629 | −47 | 316 | 53 |
| 4-I—Ph | 156 | −61 | 49073 | −40 | 315 | 52 |
| MeOCOPh | 166 | −58 | 54063 | −34 | 326 | 57 |

When added to AMPD-10, the aryl boronic acids reduced both background and CL (RLU). The background reduction is more significant, therefore giving improved S/N ratios.

Example 11. Polymer Bound Boronic Acid

Polymeric beads were loaded at 2.6-3.2 mmol/g phenyl boronic acid. Four formulations were prepared by adding polymer-bound phenyl boronic acid (at 0.05, 0.20, 1.0 and 5.0 mg/mL respectively, to AMPD-10. These four formulations along with AMPD-10 as a control were placed at 30° C. On test days 2, 6, 7, 8, 10 and 12, the formulations at 30° C. and AMPD at 4° C. were taken out and allowed to equilibrate to room temperature. After testing, the bottles were returned to storage temperatures. Although the addition of polymer-bound boronic acid at up to 5.0 mg·mL reduced the background RLU without significantly affecting the signal RLU, no improvement was observed in stability, even at 5 mg/mL (data not shown).

Example 12. Stability Study of 4-Tolyl Boronic Acid in AMPD-10

Three formulations were prepared by adding 4-tolylboronic acid (4-TBA) at 0.05, 0.25, 1.0 mM respectively to AMPD-10 Formulation A: CPA (0.15 g/L), PEG (Mw=35K, 1.0 g/L), SDS (0.9 g/L), $Na_2SO_3$ (10 mg/L) and lucigenin (3.26 mg/L) in 2-amino-2-methyl-1,3-propanediol (AMPD) buffer (0.1 M, pH 9.7).

These formulations along with AMPD-10 as control bottled in 8 mL amber-colored HDPE bottles placed at 30 and 4° C. and tested on different days comparing 30° C. to 4° C. Table 26 shows stability as percent change in signal RLU from 30° C. vs. 4° C.

TABLE 26

Change in at 30° C. vs. 4° C. with 4-TBA in AMPD-10

| | Signal RLU Stability, Change 30° C. vs 4° C. | | | |
|---|---|---|---|---|
| Day | AMPD-10-ctrl | 0.05 mM 4-TBA | 0.25 mM 4-TBA | 1.00 mM 4-TBA |
| 2 | −2.5% | −3.1% | −0.7% | −0.6% |
| 6 | −3.0% | −2.0% | −2.4% | −2.0% |
| 7 | −3.3% | −1.7% | −2.1% | −3.0% |
| 8 | −2.8% | −1.9% | −0.9% | −1.6% |
| 12 | −4.8% | −2.3% | −2.8% | −3.9% |
| 14 | −5.9% | −2.4% | −4.8% | −4.9% |

The AMPD-10 with dissolved 4-TBA exhibited some improvement over AMPD-10 control.

Example 13. Stability Study of AMPD-10 with Added 4-Tolyl Boronic Acid, and p-Cresol An isochronous study was performed with AMPD-10 containing additional candidate background reducing agents. Three substrate formulations of the present invention were tested: AMPD-10 (DLS081114), AMPD-10 with p-cresol 0.05 mM, and AMPD-10 with 4-tolyl boronic acid (4-TBA) 0.05 mM. These formulations were bottled in 8 mL amber-colored HDPE bottles. Bottles were removed from 4° C. and placed at 30° C. at different days to give formulations with different storage time at 30° C. These formulations were tested on the same plate by reading RLUs in the presence of AP on BMG at 37° C. (30 min. equilibration). Stability at Days 0, 1, 2, 3, 6 and 9 was determined. Mean signal and background RLUs for each formulation are shown in Tables 27A-27C.

TABLE 27A

Stability of AMPD-10 Fast Substrate for 9 days

| | AMPD-10-ctrl | | | |
|---|---|---|---|---|
| | Signal | | Background | |
| DAY | Mean RLU | Change | Mean RLU | Change |
| 0 | 85087 | | 418 | |
| 1 | 84355 | −0.9% | 397 | −5.0% |
| 2 | 83561 | −1.8% | 367 | −12% |
| 3 | 84454 | −0.7% | 358 | −14% |
| 6 | 83135 | −2.3% | 334 | −20% |
| 9 | 82302 | −3.3% | 359 | −14% |

TABLE 27B

Stability of AMPD-10-p-Cresol 0.05 mM for 9 days

| | AMPD-10-p-Cresol 0.05 mM | | | |
|---|---|---|---|---|
| | Signal | | Background | |
| DAY | Mean RLU | Change | Mean RLU | Change |
| 0 | 84952 | | 552 | |
| 1 | 83357 | −1.9% | 637 | 15% |
| 2 | 82888 | −2.4% | 717 | 30% |
| 3 | 83378 | −1.9% | 638 | 16% |
| 6 | 79981 | −5.9% | 732 | 33% |
| 9 | 78257 | −7.9% | 732 | 33% |

TABLE 27C

Stability of AMPD-10-p-TBA 0.05 mM for 9 days

| | AMPD-10-p-TBA 0.05 mM | | | |
|---|---|---|---|---|
| | Signal | | Background | |
| DAY | Mean RLU | Change | Mean RLU | Change |
| 0 | 60826 | | 200 | |
| 1 | 60247 | −1.0% | 179 | −10% |
| 2 | 59971 | −1.4% | 178 | −11% |
| 3 | 61095 | 0.4% | 175 | −13% |
| 6 | 60127 | −1.1% | 177 | −11% |
| 9 | 60414 | −0.7% | 194 | −3.2% |

Figure 10A:
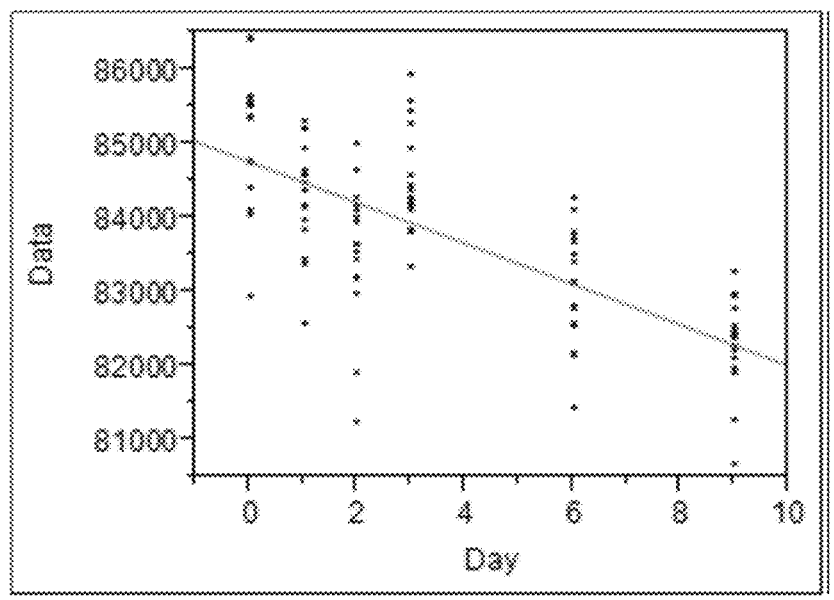
FIG. 10A shows signal relative luminescence units (RLU) over 9 days for AMPD-10-control exhibiting a slope of intensity of original signal lost per day of 0.32%/day.

FIG. 10A shows AMPD-10-control signal RLU monitored for 9 days. A slope of original signal intensity loss per day of −0.32%/day was exhibited.

Figure 10B:
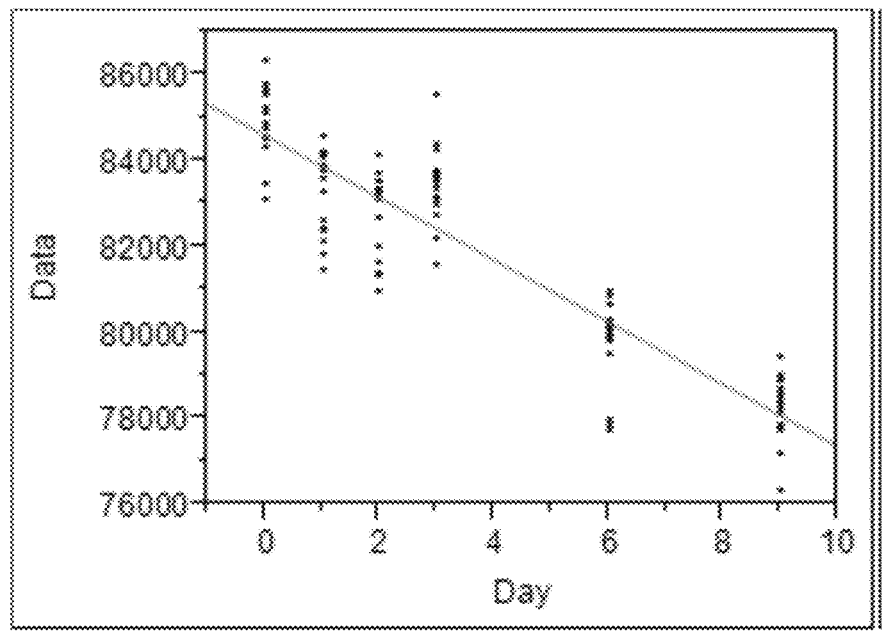
FIG. 10B shows signal RLU over 9 days for AMPD-10-p-cresol exhibiting a slope of intensity of original signal lost per day of 0.87%/day.

FIG. 10B shows AMPD-10-p-cresol exhibited a slope of original signal intensity loss of −0.87%/day.

Figure 10C:
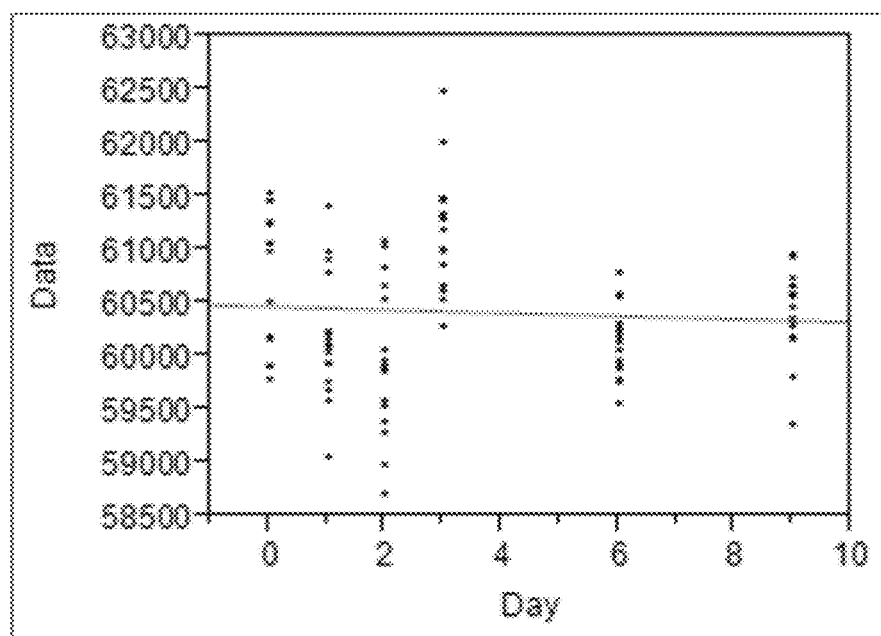
FIG. 10C shows signal RLU over 9 days for AMPD-10-4-TBA exhibiting a slope of intensity of original signal lost per day of 0.02%/day.

FIG. 10C shows AMPD-10-4-TBA exhibited a slope of intensity of original signal lost per day of −0.02%/day.

Improved stability and S/N was exhibited with 4-tolyl boronic acid (4-TBA), but not seen with 4-cresol. The AMPD-10 with 0.05 mM 4-TBA substrate formulation exhibited a signal RLU about 25-30% lower, and a background RLU of about 45-50% lower than AMPD-10-control. Significantly improved stability was observed with AMPD-10-4-TBA 0.05 mM substrate formulation under this test method compared to the AMPD-10 control formulation.

Example 14. Alternative Background Reducing Agents

Testing of different additional background reducing agents (BRAs) was performed using the following composition: CPA (0.15 g/L), 0.1 M 2-amino-2-methyl-1,3-propanediol (AMPD) buffer pH 9.7, lucigenin (3.26 mg/L), PEG (Mw=35,000, 1. 0 g/L), SDS (0.9 g/L) and BRA at indicated concentration shown in Table 28.

TABLE 28

| Background Reducing Agents | | |
|---|---|---|
| BRA | Background RLU | Signal RLU |
| SS (10 mg/L) | 910 | 86273 |
| SS + BHT | 1014 | 85007 |
| SBS (5 mg/L) | 1139 | 83110 |
| SBS (10 mg/L) | 807 | 81979 |
| SBS (25 mg/L) | 587 | 80673 |
| SMBS (5 mg/L) | 1188 | 85915 |
| SMBS(10 mg/L) | 759 | 84050 |
| SMBS (25 mg/L) | 568 | 82403 |

SS: Sodium Sulfite;
SBS: Sodium Bisulfite;
SMBS: Sodium Metabisulfite;
BHT: dibutylhydroxytoluene Background RLU and signal RLU were compared to control 10 mg/L sodium sulfite in Table 28. Use of increasing concentrations of SBS or SMBS resulted in lower background but also somewhat diminished signal.

Stability of a typical composition containing various BRAs was performed using CPA (0.15 g/L), 0.1 M A2-amino-2-methyl-1,3-propanediol (AMPD) buffer pH 9.7, lucigenin (3.26 mg/L), PEG (Mw=35,000, 1. 0 g/L), SDS (0.9 g/L) and BRA at indicated concentration. Signal Change (%) during storage at 30° C. is shown in Table 29.

TABLE 29

Stability at 30° C. using Background Reducing Agents

| | day 1 | day 4 | day 6 | day 11 | day 14 |
|---|---|---|---|---|---|
| SS (control-10 mg/L) | −2.2 | −3.9 | −4.6 | −6.2 | −7.4 |
| SS -10 mg/L + BHT-80 uM | −2.3 | −4.5 | −6.0 | −7.4 | −8.8 |
| SBS(5 mg/L) | −1.7 | −3.5 | −4.9 | −5.4 | −6.3 |
| SBS(10 mg/L) | −2.5 | −4.2 | −4.7 | −7.2 | −7.3 |
| SBS(25 mg/L) | −2.0 | −4.5 | −5.7 | −7.7 | −8.9 |
| SMBS(5 mg/L) | −1.1 | −3.3 | −2.4 | −5.4 | −6.3 |
| SMBS(10 mg/L) | −3.0 | −3.7 | −4.5 | −6.0 | −7.3 |
| SMBS(25 mg/L) | −2.4 | −4.2 | −5.4 | −7.4 | −8.5 |

BRAs also include aryl boronic acids selected from that have a general chemical structure of Ar—B(OH)$_2$, wherein Ar is a phenyl, substituted phenyl, a fused aromatic ring system that may or may or include heteroatom(s), or a substituted fused aromatic ring system that may or may include heteroatom(s). When used in combination with sulfite, bisulfite and metabisulfite salts, these aryl boronic acids provide additional benefits include improved S/N ratios and stability, as shown in Example 10.

Example 15. Stability with Varied Amounts of CPA in AMPD Buffer

A formulation stability study at 30° C. with Varied Amount of CPA in AMPD buffer was performed. Formulations were prepared as follows: CPA (varied concentration), $Na_2SO_3$ (10 mg/L), lucigenin (3.26 mg/L), PEG (1.0 g/L) and SDS (0.9 g/L) in AMPD buffer (0.1 M, pH 9.7). Results after 15 days as % signal change per day after 15 days at 30° C. are shown in Table 30.

TABLE 30

Stability at 30° C. with varied amounts of CPA in AMPD Buffer

| CPA (g/L) | Signal change per day after 15 days at 30° C. (%) |
|---|---|
| 0.113 | −0.26 |
| 0.15 | −0.29 |
| 0.188 | −0.27 |
| 0.225 | −0.28 |
| 0.263 | −0.23 |

TABLE 31

Stability at 30° C. with varied amounts of CPA in TRIS buffer

| CPA (g/L) | Signal change per day after 15 days at 30° C. (%) |
|---|---|
| 0.113 | −0.37 |
| 0.15 | −0.33 |
| 0.188 | −0.30 |
| 0.225 | −0.40 |

At each concentration of CPA, the AMPD formulations of Table 30 were more stable than TRIS formulations of Table 31.

Example 17. Formulation Stability with Different PEGs in TRIS Buffer

A formulation stability study for 14 days at 30° C. was performed with different Poly(ethylene glycol) in TRIS Buffer: CPA (0.15 g/L), $Na_2SO_3$ (10 mg/L), lucigenin (3.26 mg/L), PEG and SDS as indicated above in TRIS buffer (0.3 M, pH 8.8). Results are shown in Table 32.

TABLE 32

Stability Study with PEGs in TRIS Buffer

| PEG Mw | PEG (g/L) | SDS (g/L) | Signal Change(%) per Day Over 14 days at 30° C. |
|---|---|---|---|
| 100K | 1.0 | 0.9 | −0.49 |
| 100K | 2.5 | 1.0 | −0.58 |
| 35K | 1.0 | 0.9 | −0.47 |
| 35K | 2.0 | 0.9 | −0.53 |

Example 18. Formulation Stability at 30° C. with Different Anionic Surfactants Formulations comprising SDS or STS were prepared as follows. Formulation-SDS: CPA (0.15 g/L), $Na_2SO_3$ (10 mg/L), lucigenin (3.26 mg/L), PEG (1.0 g/L) and SDS (0.9 g/L) in AMPD buffer (0.1 M, pH 9.7). Formulation-STS: CPA (0.15 g/L), $Na_2SO_3$ (10 mg/L), lucigenin (3.26 mg/L), PEG (1.0 g/L) and STS (0.5 g/L) in AMPD buffer 0.1 M, pH 9.7). Results after 29 days of evaluation are shown in Table 33.

TABLE 33

Stability at 30° C. with Different Anionic Surfactants

| | Signal Change (%) at 30° C. | | | | | Change (%) per Day Over 29 days |
|---|---|---|---|---|---|---|
| | Day 3 | Day 6 | Day 10 | Day 14 | Day 29 | |
| Formulation-SDS | 2 | 3.2 | 4.7 | 6 | 10.7 | −0.33 |
| Formulation-STS | 1.7 | 1.3 | 2.5 | 4.4 | 7 | −0.23 |

The STS substrate formulation exhibited greater stability than the corresponding SDS substrate formulation.

Example 19. Formulation Stability at 30° C. with STS in AMPD Buffers

A substrate formulation stability study at 30° C. was performed in AMPD Buffers with CPA (0.15 g/L), $Na_2SO_3$ (10 mg/L), lucigenin (3.26 mg/L), PEG (1.0 g/L) and STS (0.5 g/L) in AMPD buffer pH 9.7 of different molarities as shown in Table 34.

TABLE 34

Stability at 30° C. with STS in AMPD Buffers

| AMPD Molarity | Signal RLU Day 0 | Signal RLU Day 12 | Signal Change (%) |
|---|---|---|---|
| 25 mM | 102251 | 106560 | −4.0 |
| 50 mM | 113023 | 116707 | −3.2 |
| 66 mM | 109517 | 114002 | −3.9 |
| 80 mM | 105413 | 109888 | −4.1 |
| 90 mM | 102434 | 107209 | −4.5 |
| 100 mM | 101750 | 105470 | −3.5 |
| 110 mM | 97949 | 101527 | −3.5 |
| 120 mM | 95238 | 98639 | −3.4 |
| 133 mM | 90378 | 94025 | −3.9 |
| 200 mM | 75432 | 78124 | −3.4 |

Signal change as % RLU at day 12 was fairly consistent over 25 mM to 200 mM AMPD buffer molarity.

Example 20. Stability with STS in AMPD at Different pH

A formulation stability study was performed at 30° C. in AMPD Buffers at various pH was performed. CPA (0.15 g/L), $Na_2SO_3$ (10 mg/L), lucigenin (3.26 mg/L), PEG (1.0 g/L) and STS (0.5 g/L) in AMPD buffer 0.1 M of different pH as shown in Table 35.

TABLE 35

Stability with STS in AMPD at Different pH

| 0.1M AMPD Buffer pH | Signal Change (%) Per Day after 18 Days at 30° C. |
|---|---|
| 9.25 | −0.37 |
| 9.5 | −0.32 |
| 9.58 | −0.31 |
| 9.63 | −0.28 |
| 9.68 | −0.24 |
| 9.73 | −0.24 |
| 9.78 | −0.23 |
| 9.85 | −0.23 |

A trend to greater stability at higher pH between from 9.63-9.85 was exhibited.

Example 21. Alternative Cationic Aromatic Compounds (CAC)

Acridinium compounds bearing either one cationic charge or two cationic charge like N,N'-dimethylbiacridinium dinitrate (commonly known as lucigenin) are among the preferred CACs. Various alternative CACs were tested in the formulation as shown in Table 36.

TABLE 36

Cationic Aromatic Compounds Imax RLU

| CAC | I max RLU (Turner 20/20e luminometer with filter) |
|---|---|
| [structure: lucigenin, 2 NO$_3^-$] | 2500 |
| [structure: dichloro-biacridinium, 2 NO$_3^-$] | 454 |
| [structure: chloro-biacridinium, 2 NO$_3^-$] | 1600 |
| [structure: anthracene-acridinium, Cl, Br$^-$] | 1037 |
| [structure: bis-isoquinolinium, 2 I$^-$] | 41 |
| [structure: ethylene-bridged bis-isoquinolinium, 2 Br$^-$] | 500 |

As shown in Table 36, lucigenin exhibited greatest Imax of the CACs tested.

Example 22. Formulations with Varied Amount of Lucigenin

To determine the effect of varying amounts of lucigenin on stability, background and signal intensity, test compositions comprising CPA (0.15 g/L), 35K PEG (1.0 g/L), SDS (0.9 g/L), Na$_2$SO$_3$ (10 mg/L) and in 0.3 M Tris Buffer, pH 9.2 were prepared with various amounts of CAC lucigenin as shown in Table 37. The background and signal RLUs were assesses as shown in Table 37. A trend to higher background and somewhat decreased S/N was seen at highest CAC concentration.

TABLE 37

Effect of Lucigenin Concentration on Background and Signal RLU

| Lucigenin Conc. (mg/L) | Background RLU | Signal RLU |
|---|---|---|
| 0.815 | 112 | 41511256 |
| 1.63 | 125 | 47793807 |
| 2.445 | 137 | 47353394 |
| 3.26 | 137 | 45461394 |
| 4.075 | 151 | 42428524 |
| 4.89 | 155 | 39634594 |

Figure 11:
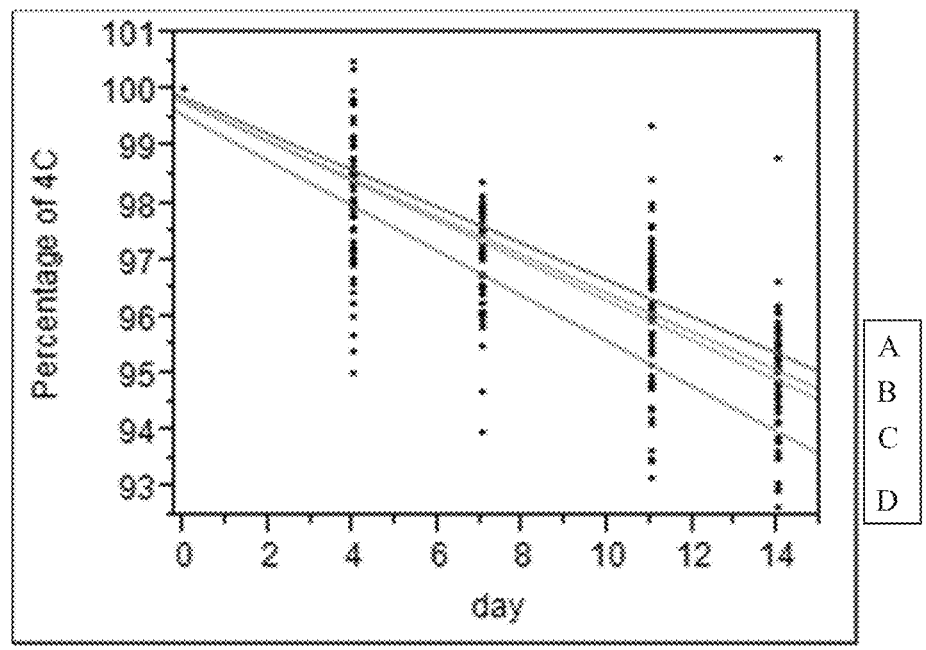
FIG. 11 shows stability of substrate formulations comprising (A) 0.6×, (B) 0.7×, (C) 1× and (D) 1.3× Lucigenin at 30° C. as percentage performance relative to corresponding 4° C. sample. A trend to decreased stability was seen at higher CAC concentrations.

*Background RLUs and signal RLUs obtained respectively from Turner 20/20 and a SpectraMax-L Test compositions containing 0.6×, 0.7×, 1× and 1.3× Lucigenin were prepared and compared to a composition comprising 1× lucigenin=3.26 mg/L. Other components were CPA (0.15 g/L), 35K PEG (1.0 g/L), SDS (0.9 g/L), $Na_2SO_3$ (10 mg/L) and in 0.1 M AMPD Buffer, pH 9.7. Formulations comprising 0.6× (1.96 mg/L), 0.7× (2.28 mg/L), 1× (3.26 mg/L), and 1.3× (4.24 mg/L) lucigenin were evaluated stability studies. Each formulation was stored at 4° C. and 30° C. and tested at four time points. Stability of substrate formulations comprising 0.6×, 0.7×, 1× and 1.3× Lucigenin at 30° C. is shown as percentage performance relative to the corresponding 4° C. sample in FIG. 11, wherein A is slope (0.6×)=0.32%/day; B is slope (0.7×)=0.35%/day; C is slope (1×)=0.34%/day and D is slope (1.3×)=0.40%/day. A trend to decreased stability was seen at higher CAC concentrations.

Example 23. Fast Substrate Formulation Reduces Time to First Result

A test substrate formulation was prepared comprising 0.15 g/L CPA, 3.26 mg/L Lucigenin, 10 mg/L sodium sulfite; 1 g/L PEG (35K), 0.9 g/L SDS; and 0.1 M AMPD pH 9.7 buffer system.

The test substrate formulation was employed in 23 automated assays as a replacement to Lumi-Phos 530® (Access Substrate Cat. No. 81906, Beckman Coulter, Fullerton, Calif., USA) in modified automated UniCel DxI Access Immunoassay System according to manufacturer's protocol for quantitative determination of various analytes: TSH-fast, TSH-Hypersensitive (thyrotropin, hTSH Reagent, Beckman Coulter Ref. 33820), FT4 (Access Total Thyroxine (T4) Reagent, Beckman Coulter 33800), Ferritin (Access Ferritin Reagent, Beckman Coulter Ref. 33020), AccuTnI (Cardiac Troponin I (cTbI) Reagent, 33340, Beckman Coulter), VitB12 (Access Vitamin B12 Reagent, Beckman Coulter 33020), PSA (Access Hybritech PSA Reagent, Beckman Coulter 37200), FOL (Access Folate Reagent, Beckman Coulter A98032), FT3 (Access Total T3 Reagent, Beckman Coulter 33830), TBhCG2 (Access total beta human Chorionic Gonadotropin, hCG Reagent, Beckman Coulter A85264), CK-MB (Access Creatine Kinase-MB Reagent, 386371, Beckman Coulter, Inc.), BNP2 (Access B-type natriuretic peptide reagent, 98200; Beckman Coulter, Inc.); AFP (Access alpha-fetoprotein reagent, 33211, Beckman Coulter, Inc.), CEA2 (Access Carcinoembryonic Antigen Reagent, 33200, Beckman Coulter, Inc.); Dil-hCG2 (Access total beta human Chorionic Gonadotropin Reagent, 33500, Beckman Coulter, Inc.); hFSH (Access human Follicle Stimulating Hormone Reagent, 33520, Beckman Coulter, Inc.), PTH (IO) (Access Parathyroid Hormone, intact-Intra-operative mode, insert A38412B, Beckman Coulter, Inc.), PTH routine (Access intact Parathyroid Hormone Reagent, A16972, Beckman Coulter, Inc.), hLH (Access human Luteinizing Hormone Reagent, 33510, Beckman Coulter, Inc.); Testo (Access Testosterone Reagent, 33560, Beckman Coulter, Inc.), Cortisol (Access Cortisol Reagent, 33600, Beckman Coulter, Inc.); E2 (Access Estradiol Reagent, 33540, Beckman Coulter, Inc.), and InhibinA (Access Inhibin A Reagent, A36097, Beckman Coulter, Inc.).

The time to result in each automated assay was determined using the test substrate formulation compared to the standard LUMI-PHOS 530 assay substrate. Results are shown in FIG. 13.

The substrate formulations of the present invention decreased time to result from 10%-41% in the automated assays compared to LUMI-PHOS® 530 substrate formulation, as shown in FIG. 13. As shown in FIG. 13, use of the substrate formulations of the present invention in 8 of the top 23 assays saved at least 30% time to first result compared to LUMI-PHOS 530 assay substrate system. The % time saved in the top 23 assays is shown graphically in FIG. 13.

Example 24. Representative Automated Immunoassay

The following protocol is representative of automated immunoassays suitable for substitution of the present substrate formulations for LUMI-PHOS 530 for detection of an alkaline phosphatase (ALP) enzyme.

In some embodiments, a detectable label that is either inherently detectable or covalently bound to a signal generating system such as a conjugated detectable phosphatase enzyme (e.g., T4-ALP or T3-ALP in a competitive immunoassay for Free T4), competes with analyte (e.g., Free T4 in a fluid sample) for binding to a capture ligand (e.g., T4-specific monoclonal antibody).

In this example, the Access Free T4 assay (BCI) is a two-step enzyme immunoassay. BCI's Access FT4 assay system (BCI, Fullerton, Calif.) is used to measure the concentration of free non-protein bound thyroxine in the serum or plasma of subjects. Monoclonal anti-Thyroxine (T4) antibody (BCI) coupled to biotin, a biological sample containing T4, buffered protein solution containing stabilizing agent, and streptavidin-coated solid phase are added to a reaction vessel. During this first incubation the anti-T4 antibody coupled to biotin binds to the solid phase and the free T4 in the sample. After incubation in a reaction vessel, materials bound to the solid phase are held in a magnetic field while unbound materials are washed away.

Next, buffered protein solution and triiodothyronine (T3)-alkaline phosphatase conjugate are added to the reaction vessel. The T3-alkaline phosphatase conjugate binds to the vacant anti-T4 antibody binding sites. After incubation in a reaction vessel, materials bound to the solid phase are held in a magnetic field while unbound materials are washed away.

Then, the chemiluminescent substrate Lumi-Phos®530 (Lumigen Inc., Southfield, Mich.), or inventive substrate formulation, is added to the vessel and light generated by the reaction is measured with a luminometer. The light production is inversely proportional to the concentration of free T4 in the sample. The amount of analyte in the sample is determined from a stored, multi-point calibration curve. Serum and plasma (heparin) are the recommended samples.

BCI's Access Free T4 A33070A assay kit includes an Access Free T4 Reagent Pack Cat. No. 33880: 100 determinations, 2 packs, 50 tests/pack. It is provided ready to use. The reagent pack contains the following Reagents A through E:

Reagent A: Dynabeads® paramagnetic particles coated with streptavidin in a TRIS buffer with protein (aves), surfactant, 0.125% NaN₃, and 0.125% ProClin® 300 (available from Rohm and Haas, Philadelphia, Pa.).

Reagent B: TRIS buffered saline with protein (aves), surfactant, <0.1% NaN₃, and 0.1% ProClin 300.

Reagent C: TRIS buffered saline with protein (aves), surfactant, 0.125% NaN₃, and 0.125% ProClin 300.

Reagent D: Triiodothyronine-alkaline phosphatase (bovine) conjugate in a TRIS buffer with protein (aves), surfactant, <0.1% NaN₃, and 0.1% ProClin 300.

Reagent E: Mouse monoclonal anti-Thyroxine (T4) coupled to biotin in a TRIS buffer with protein (aves and murine), surfactant and stabilizing agent, 0.125% NaN₃, and 0.125% ProClin® 300.

The first reaction comprises the following sequential additions to the reaction vessel:
1) 50 uL of Reagent E;
2) 30 uL of analyte-containing sample;
3) 30 uL of system Wash Buffer;
4) 30 uL of Reagent B;
5) 50 uL of Reagent A.

Following incubation period and washes of the reaction vessel, the second reaction comprises the following sequential additions to the reaction vessel:
6) 220 uL of Reagent C;
7) 50 uL of Reagent D;
8) 80 uL of system wash buffer;
9) incubation;
10) LumiPhos-530 or inventive substrate formulation addition;
11) 6.3 min incubation;
12) detection.

Following incubation and washes of the reaction vessel, the concentration of the free analyte in the sample is measured using the detection system.

Example 25. Stability of Formulation with PEG 35K at 30° C.

Figure 12:
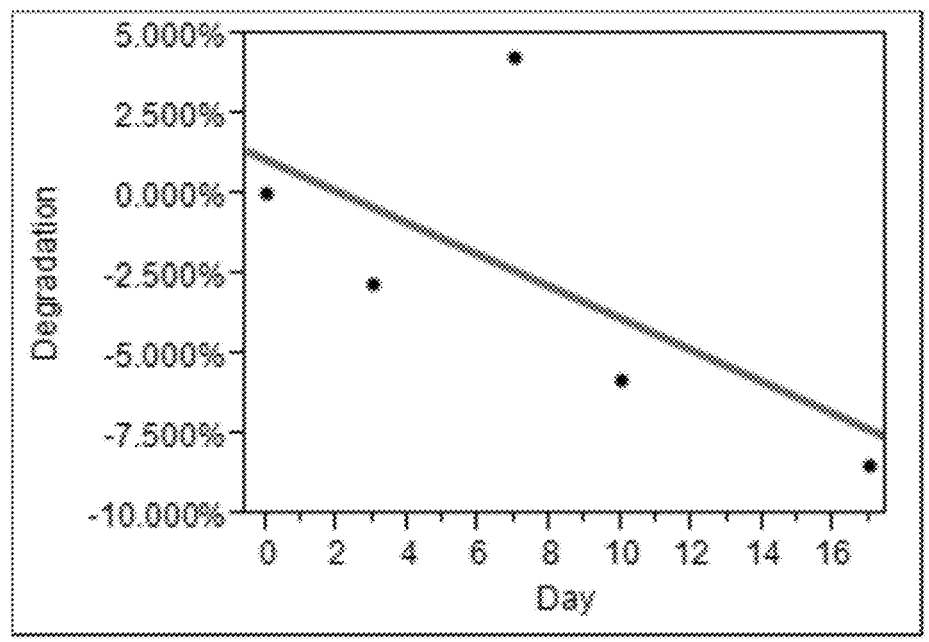
FIG. 12 shows stability of a substrate formulation comprising 0.3 M TRIS pH 8.8, 3.26 mg/L Lucigenin, 10 mg/L Sodium Sulfite, 1 g/L PEG (35K), 0.9 g/L SDS, and 0.15 g/L CPA when stored at 30° C.

A substrate formulation comprising 0.3 M Tris pH 8.8, 3.26 mg/L Lucigenin, 10 mg/L Sodium Sulfite, 1 g/L PEG (35K), 0.9 g/L SDS, and 0.15 g/L CPA was prepared. Stability of the substrate formulation at 30° C. was determined. Degradation profile is shown in FIG. 12. The slope was determined to be −0.5% per day at 30° C., p-value<0.001 for the composition comprising PEG 35K with SDS 0.9 g/L.

Example 26. Additional Formulations with Various Chemiluminescent Compounds I

Two substrate formulations were prepared with a various compounds of formula I. The first was based on the prior art system used with APS-5 and contained Tris 0.3 M pH 9.35 containing 1 g/L SDS, 1 g/L Tween®-20. 3.25 mg/L Lucigenin, 10 mg/L Sodium Sulfite. The second was based on the present invention and included AMPD 0.1 M pH 9.70 containing 0.5 g/L STS, 1 g/L PEG (Mw=35,000), 3.25 mg/L Lucigenin, 10 mg/L Sodium Sulfite. Various chemiluminescent compounds I shown below were added to 200 mL aliquots of each buffer at 0.15 g/L.

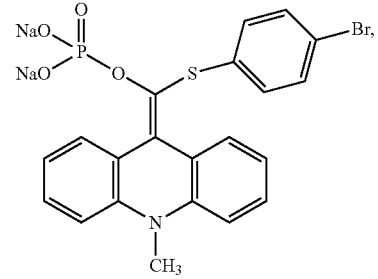

1

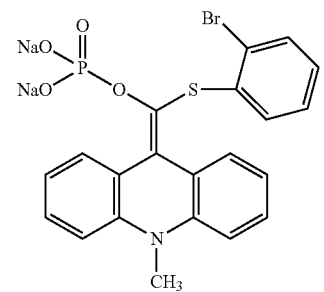

2

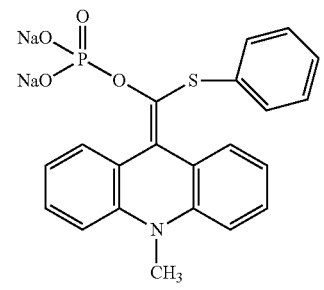

3

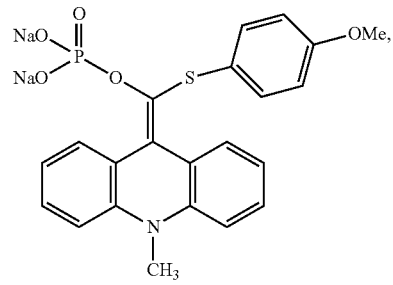

4

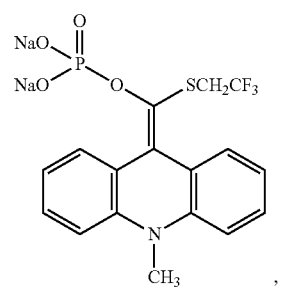

5

-continued

6

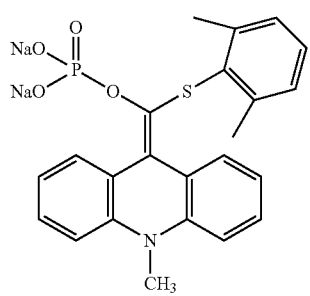

7

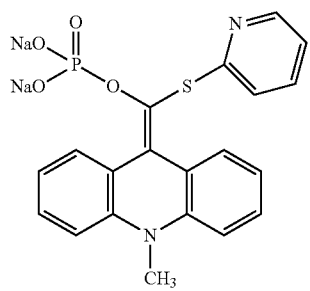

8

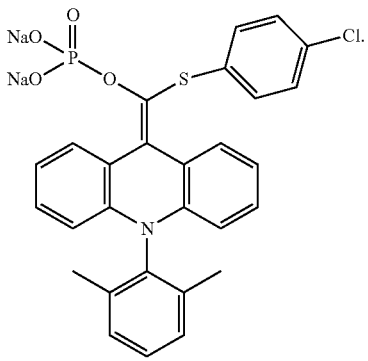

Each formulation was split into ~100 mL halves with one kept at ~5° C. and the other kept at −30° C.

Material was tested periodically over two weeks measuring the relative change in signal RLU between the two storage conditions. Formulations were tested in 96-well plates by comparing samples at stored at two temperatures to reduce the variability associated with enzymes/temperature/day to day. The samples were incubated at 37° C. for 30 minutes on the instrument 20 uL of enzyme (prepared by mixing 1 mL of Beckman Coulter System Check ALP with 640 mL of the Sample Diluent Buffer) were injected into 200 uL of formulation. Kinetic signal was measured at ~29 seconds after injection of ALP solution. 15-16 data points (wells) were measured for each Buffer/Temperature/Time point (Well A1 is excluded due to variation in injection volume). Data was plotted with a linear regression and with the slope reported as % lost per day, as shown in Table 38 at 30° C.

TABLE 38

Stability of Chemiluminescent Compounds I in two buffer systems

| Compound | Buffer | Signal Loss at 30° C. (slope, % loss/Day) |
|---|---|---|
| 1 | AMPD | 0.38% |
|  | TRIS-Tween | 0.50% |

TABLE 38-continued

Stability of Chemiluminescent Compounds I in two buffer systems

| Compound | Buffer | Signal Loss at 30° C. (slope, % loss/Day) |
|---|---|---|
| 2 | AMPD | 0.13% |
|  | TRIS-Tween | 0.29% |
| 3 | AMPD | 0.53% |
|  | TRIS-Tween | 0.61% |
| 4 | AMPD | 0.76% |
|  | TRIS-Tween | 1.04% |
| 5 | AMPD | 1.13% |
|  | TRIS-Tween | 1.28% |
| 6 | AMPD | 1.21% |
|  | TRIS-Tween | 1.61% |
| 7 | AMPD | 0.26% |
|  | TRIS-Tween | 0.84% |
| 8 | AMPD | 2.59% |
|  | TRIS-Tween | 3.38% |

The formulations prepared in the AMPD buffer system showed less signal loss than the corresponding formulations in the TRIS-Tween buffer system.

We claim:

1. A substrate formulation which produces chemiluminescence in the presence of a phosphatase enzyme and which comprises in an aqueous solution:
   a) 0.01 mM-50 mM of a chemiluminescent compound of formula I or a salt thereof:

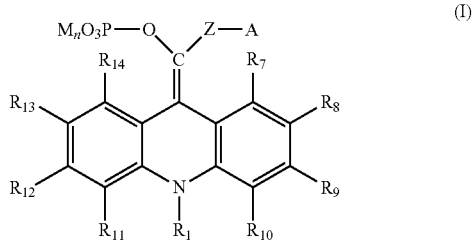

wherein
   A is $C_{1-6}$haloalkyl, naphthyl, phenyl, substituted phenyl, or heteroaryl, wherein substituted phenyl comprises from 1 to 3 halo, $C_{1-6}$ alkyl, $C_{1-6}$ alkoxy, $C_{1-6}$ haloalkyl, $C(O)R_{15}$, CN or $NO_2$ substituents;
   $R_1$ is selected from the group consisting of $C_{5-14}$aryl, $C_{1-6}$ alkyl, $C_{1-6}$ haloalkyl, and $C_{5-14}$ aralkyl groups;
   $R_7$-$R_{14}$ are independently H, $C_{1-6}$ alkoxy, halo, $C_{1-4}$alkyl, or $R_7$ or $R_8$-$R_9$ or $R_9$-$R_{10}$ or $R_{11}$-$R_{12}$ or $R_{12}$-$R_{13}$ or $R_{13}$-$R_{14}$, can be joined together as a carbocyclic or heterocyclic ring system comprising at least one 5 or 6-membered ring;
   $R_{15}$ is $C_{1-6}$ alkyl;
   each M is independently selected from the group consisting of H, an alkali metal, alkaline earth metal, transition metal, ammonium, phosphonium, organic amine salt, and an amino acid salt;
   Z is O or S; and
   n is 0, 1, or 2;
   b) 0.01-200 µM of a cationic aromatic compound (CAC);
   c) 1 µM-10 mM of a background reducing agent; and
   d) 0.05-20 g/L of an ether-linked nonionic surfactant that does not contain a carboxylate ester group; or a hydrophilic polymer.

2. The substrate formulation according to claim 1, wherein

Z is S;

A is selected from the group consisting of phenyl and substituted phenyl, wherein substituted phenyl comprises from 1 to 3 halo, $C_{1-6}$ alkyl, $C_{1-6}$alkoxy, and $C_{1-6}$haloalkyl substituents;

$R_1$ is methyl, ethyl, propyl, isopropyl, n-butyl, sec-butyl or t-butyl;

$R_7$-$R_{14}$ are independently H, $C_{1-6}$alkoxy, or halo;

each M is independently H, Na, K, or Li; and n is 0, 1, or 2.

3. The substrate formulation according to claim 1, wherein the compound of formula I is selected from the group consisting of

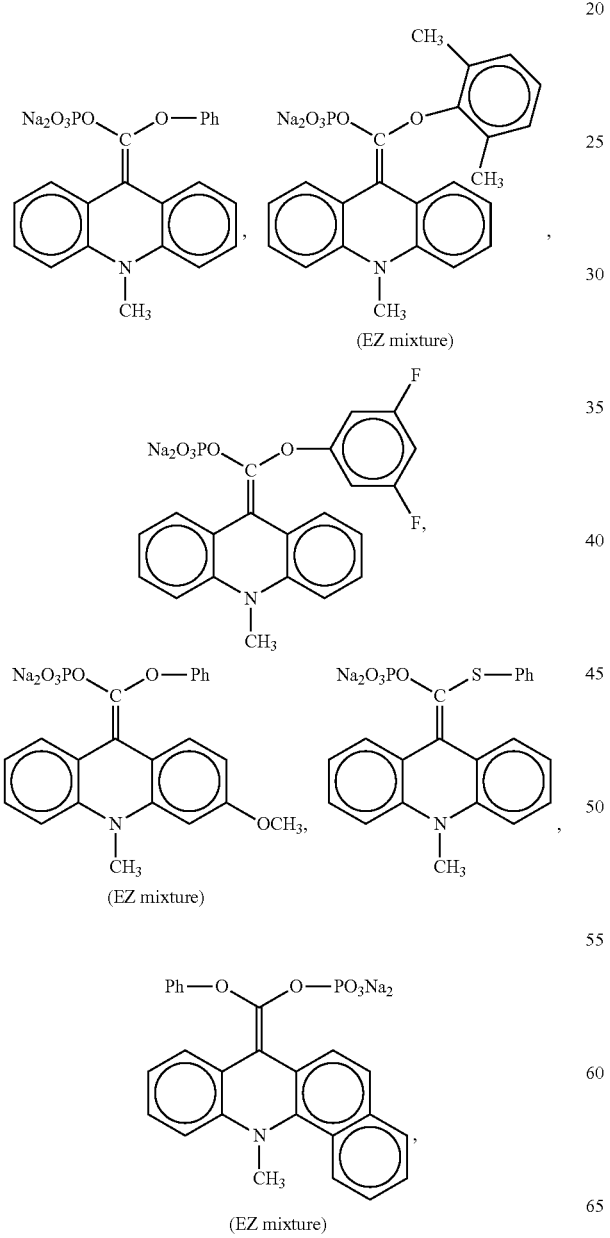

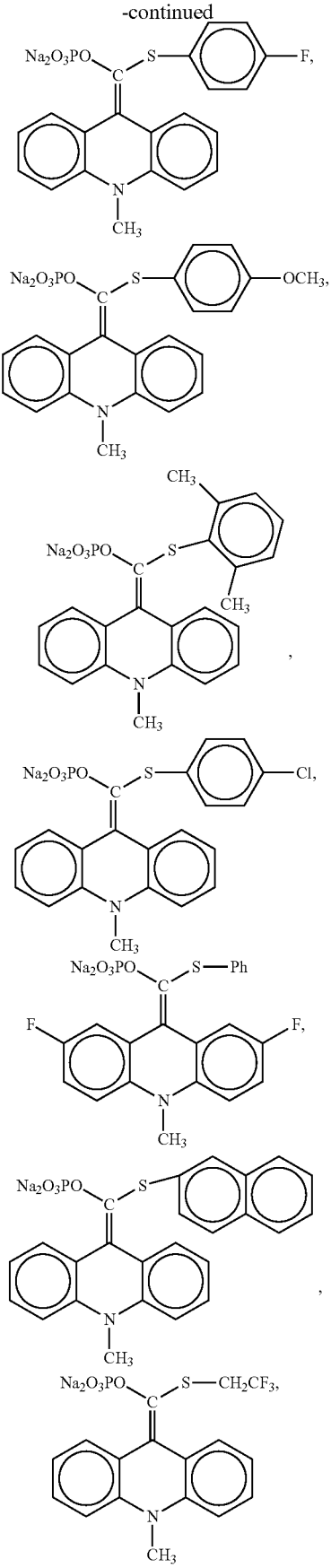

-continued

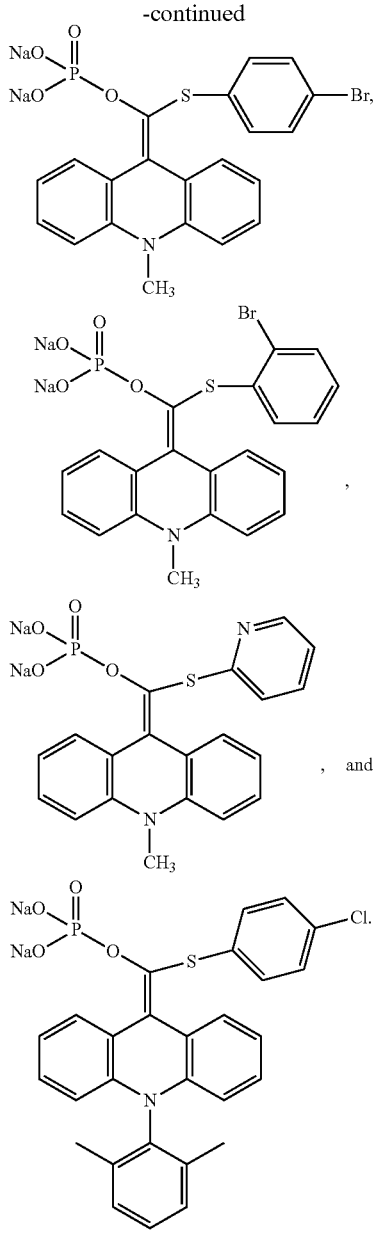

4. The substrate formulation according to claim 1, wherein the cationic aromatic compound (CAC) is selected from a compound according to formula IL

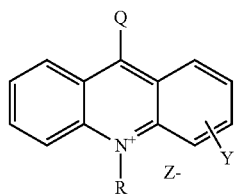
(II)

wherein
Q is selected from the group consisting of halo, cyano, —COOR', —COSR', —CONR¹R², —CON(R)SO₂R", naphthyl, anthryl, N—C₁₋₄ alkyl acridinyl, and halo substituted N—C₁₋₄ alkyl acridinyl;

R is C₁₋₄ alkyl;
R', R" are independently selected from the group consisting of C₁₋₆ alkyl, aryl, and alkyl substituted aryl;
R¹, R² are independently selected from the group consisting of H, C₁₋₆ alkyl, aryl, and alkylaryl; and
Z⁻ is a halide or nitrate; and
Y is selected from the group consisting of H, halo, and C₁₋₄ alkyl.

5. The substrate formulation according to claim 4, wherein Q is N-methyl acridinyl, halo substituted N-methyl acridinyl, naphthyl, or anthryl; R is C₁₋₄ alkyl; Z— is selected from the group consisting of Cl⁻, Br⁻, I⁻, and NO₃⁻, and Y is H or halo.

6. The substrate formulation according to claim 5, wherein the CAC is selected from the group consisting of

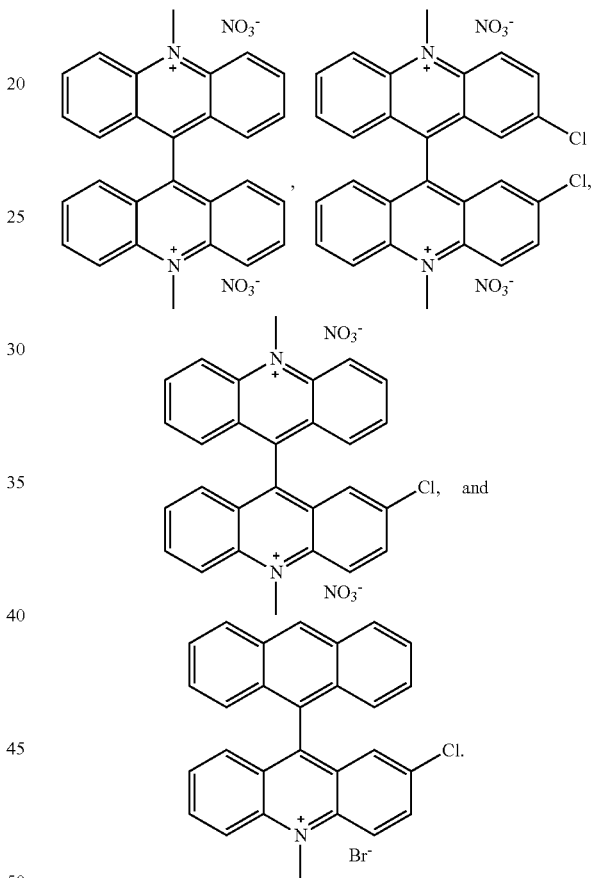

7. The substrate formulation of claim 1, wherein the background reducing agent is selected from the group consisting of lithium sulfite, sodium sulfite, potassium sulfite, lithium bisulfite, sodium bisulfite, potassium bisulfite, lithium metabisulfite, sodium metabisulfite, potassium metabisulfite, dibutylhydroxytoluene (BHT; 2,6-bis(1,10dimethylethyl)-4-methylphenol), butylated hydroxyl anisole (BHA), 3-t-butyl-4-hydroxyanisole, 3-tert-butyl-4-hydroxyanisole, and an aromatic boronic acid of formula Ar—B(OH)₂, wherein Ar is phenyl, substituted phenyl, a fused aromatic ring system that may or may or include heteroatom(s), a substituted fused aromatic ring system that may or may include heteroatom(s), wherein the substituted aryl group may have from 1-3 substituents independently selected from C₁₋₆ alkyl, halo, alkoxycarbonyl, or hydroxyl groups.

8. The substrate formulation of claim 7, wherein the background reducing agent is selected from the group consisting of phenyl boronic acid, 4-tolyl boronic acid, 4-chloroboronic acid, 4-iodoboronic acid and 3-methoxycarbonylphenyl boronic acid, and sodium sulfite.

9. The substrate formulation of claim 1, wherein the ether-linked nonionic surfactant is of formula (III):

(III)

wherein R is selected from $C_{6-22}$alkyl, cycloalkyl, $C_{6-22}$alkyl-substituted cycloalkyl, and mono- or di-$C_{6-22}$alkyl-substituted phenyl; n is a number from 2-200; X is selected from O or S; and Y is selected from H or $C_{1-4}$ alkyl.

10. The substrate formulation of claim 9, wherein the ether-linked nonionic surfactant is selected from the group consisting of a polyoxyethylene glycol alkyl ether (BRIJ), a polyoxyethylene glycol octylphenol ether (TRITON), or a polyoxyethylene nonylphenyl ether (IGEPAL).

11. The substrate formulation of claim 1, wherein the hydrophilic polymer is according to formula (IV):

(IV)

wherein $X_1$ and $X_2$ are independently selected from O, S, N or NH, or are absent; $Y_1$ and $Y_2$ are independently selected from H, $H_2$ or $C_{1-4}$ alkyl; and n is a number from 20 to 12,000.

12. The substrate formulation of claim 11, wherein the hydrophilic polymer is a poly(ethylene glycol) having an average Mw within the range of 1,000 to 511,000.

13. The substrate formulation of claim 1, further comprising an anionic surfactant selected from the group consisting of $C_{10-22}$alkyl sulfate and $C_{10-22}$alkyl sulfonate.

14. The substrate formulation of claim 13, wherein the anionic surfactant is selected from the group consisting of sodium tetradecyl sulfate, sodium dodecyl sulfate (SDS), and sodium tridecyl sulfate (STS).

15. The substrate formulation of claim 1, further comprising an amine buffer selected from the group consisting of iris (tromethamine); AMPD(2-amino-2-methyl-1,3-propanediol); DEA (diethanolamine); AMPSO(N-(1,1-Dimethyl-2-hydroxyethyl)-3-amino-2-hydroxypropanesulfonic acid); 221-Amine (2-amino-2-methylpropan-1-ol); CHES (2-(N-cyclohexylamino)ethanesulfonic acid); glycine; and TAPS (N-Tris(hydroxymethyl)m arinopropanesulfonic acid) buffer at pH 7-12.

16. The substrate formulation of claim 1, comprising 0.05 mM-10 mM compound 0.05-50 µM cationic aromatic compound, 10-1000 µM background reducing agent that does not contain a carboxylate ester group, 0.1 to 10 g/L ether-linked non-ionic surfactant or hydrophilic polymer, 0.1 to 5 g/L anionic surfactant, and an amine buffer at pH 8-11.

17. The substrate formulation of claim 16, wherein the compound I is CPA; the CAC is lucigenin; the background reducing agent is sodium sulfite; the non-ionic surfactant is selected from IGEPAL (CO-990, DM-970), TRITON (X-405, X-405 reduced), and BRIJ (78, 700); the hydrophilic polymer is selected from poly(ethylene glycol) (Mw=14,000), poly(ethylene glycol) (Mw=35,000), and poly(ethylene glycol) (Mw=100,000); the anionic surfactant is selected from SDS and STS; and the amine buffer is selected from TRIS and AMPD.

18. The substrate formulation of claim 1, wherein the substrate formulation exhibits one or more of:
a) achieves maximum intensity (Imax) in ≤5 minutes, ≤4 minutes, ≤2 minutes, ≤1 minute, ≤45 seconds, ≤30 seconds, ≤20 seconds, ≤10 seconds, ≤5 seconds, ≤4 seconds, ≤3 seconds, or ≤2 seconds after exposure to an alkaline phosphatase enzyme;
b) exhibits ≤10% loss of original RLU after exposure to a alkaline phosphatase enzyme after storage at 4° C. for 300 days;
c) exhibits ≥90%, or ≥95% retained activity (RLU), compared to original RLU, when stored at 4° C. for 300 days or more;
d) exhibits ≥90% retained activity when stored at 4° C. for 400 days or more; and/or
e) exhibits a signal change in (%) per day after 15 days when stored at 30° C. of <–0.50%/day.

19. A substrate formulation which produces chemiluminescence in the presence of a phosphatase enzyme, wherein the composition comprises in an aqueous solution:
a) a chemiluminescent compound of formula (I) or a salt thereof:

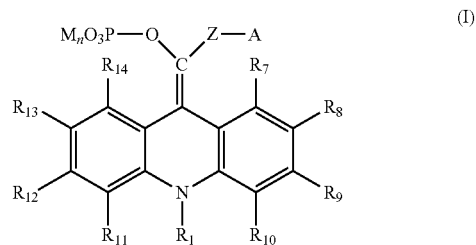

(I)

wherein
A is $C_{1-6}$haloalkyl, naphthyl, phenyl, substituted phenyl, or heteroaryl, wherein substituted phenyl comprises from 1 to 3 halo, $C_{1-6}$ alkyl, $C_{1-6}$ alkoxy, $C_{1-6}$ haloalkyl, $C(O)R_{15}$, CN or $NO_2$ substituents;
$R_1$ is selected from the group consisting of $C_{5-14}$aryl, $C_{1-6}$ alkyl, $C_{1-6}$ haloalkyl, and $C_{5-14}$ aralkyl groups;
$R_7$-$R_{14}$ are independently H, $C_{1-6}$ alkoxy, halo, or $C_{1-4}$alkyl, or $R_7$-$R_8$ or $R_8$-$R_9$ or $R_9$-$R_{10}$ or $R_{11}$-$R_{12}$ or $R_{12}$-$R_{13}$ or $R_{13}$-$R_{14}$, can be joined together as a carbocyclic or heterocyclic ring system comprising at least one 5 or 6-membered ring;
$R_{15}$ is $C_{1-6}$ alkyl;
M is independently selected from H, Li, Na, or K;
Z is O or S; and
n is 0, 1, or 2;
b) a cationic aromatic compound in an amount effective to increase the chemiluminescence compared to that generated in the absence of the cationic aromatic compound; and
c) a background reducing agent,
wherein the improvement comprises
d) an ether-linked non-ionic surfactant that does not contain a carboxylate ester group and/or a hydrophilic polymer in the aqueous solution,
wherein the resultant turnaround time (TAT) is less than 2 minutes following exposure to alkaline phosphatase in an automated immunoassay or Performance Test B.

* * * * *